United States Patent
Ma et al.

(10) Patent No.: US 9,062,071 B2
(45) Date of Patent: Jun. 23, 2015

(54) SUBSTITUTED PIPERIDINES AS HDM2 INHIBITORS

(71) Applicant: Merck Sharp & Dohme Corp, Rahway, NJ (US)

(72) Inventors: Yao Ma, Lexington, MA (US); Manami Shizuka, Lexington, MA (US); Timothy J. Guzi, Sudbury, MA (US); Yuan Liu, Belmont, MA (US); Yuan Tian, Newton, MA (US); Brian R. Lahue, Millbury, MA (US); Craig R. Gibeau, Natick, MA (US); Gerald W. Shipps, Jr., Stoneham, MA (US); Yaolin Wang, Short Hills, NJ (US); Stephane L. Bogen, Somerset, NJ (US); Latha G. Nair, Edison, NJ (US); Weidong Pan, Somerset, NJ (US); Mark A. McCoy, Basking Ridge, NJ (US); Matthew E. Voss, Ville de West (SG); Margarita Kirova-Snover, Troy, NY (US); W. Bent Clayton, Wynantskill, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/366,466

(22) PCT Filed: Dec. 17, 2012

(86) PCT No.: PCT/US2012/069996
§ 371 (c)(1),
(2) Date: Jun. 18, 2014

(87) PCT Pub. No.: WO2013/096150
PCT Pub. Date: Jun. 27, 2013

(65) Prior Publication Data
US 2014/0323482 A1  Oct. 30, 2014

Related U.S. Application Data
(60) Provisional application No. 61/578,589, filed on Dec. 21, 2011.

(51) Int. Cl.
C07D 409/14    (2006.01)
C07D 495/04    (2006.01)
A61K 31/497    (2006.01)

(52) U.S. Cl.
CPC ............ *C07D 495/04* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 6,403,584 B1 | 6/2002 | de Laszlo et al. |
| 6,645,987 B2 | 11/2003 | Chackalamannil et al. |
| 7,807,672 B2 | 10/2010 | Deng et al. |
| 7,851,626 B2 | 12/2010 | Ding et al. |
| 7,884,107 B2 | 2/2011 | Ma et al. |
| 2004/0180887 A1 | 9/2004 | Branch et al. |
| 2004/0259867 A1 | 12/2004 | Fotouhi |
| 2004/0259884 A1 | 12/2004 | Haley et al. |
| 2005/0037383 A1 | 2/2005 | Taremi et al. |
| 2005/0272751 A1 | 12/2005 | McKerracher et al. |
| 2008/0004257 A1 | 1/2008 | Chan et al. |
| 2008/0004286 A1 | 1/2008 | Wang et al. |
| 2008/0004287 A1 | 1/2008 | Ma et al. |

FOREIGN PATENT DOCUMENTS

| WO | WO0015657 | 3/2000 |
|---|---|---|
| WO | WO03051359 | 6/2003 |
| WO | WO2004080460 | 9/2004 |

(Continued)

OTHER PUBLICATIONS

Barak, mdm2 expression is induced by wild type p53 activity, The EMBO Journal, 1993, 461-468, 12-2.

(Continued)

*Primary Examiner* — Zinna Northington Davis
(74) *Attorney, Agent, or Firm* — Yong Zhao; Laura M. Ginkel

(57) ABSTRACT

The present invention provides a compound of Formula I (The formula should be inserted here) as described herein or a pharmaceutically acceptable salt or solvate thereof. The representative compounds are useful as inhibitors of the HDM2 protein. Also disclosed are pharmaceutical compositions comprising the above compounds and potential methods of treating cancer using the same.

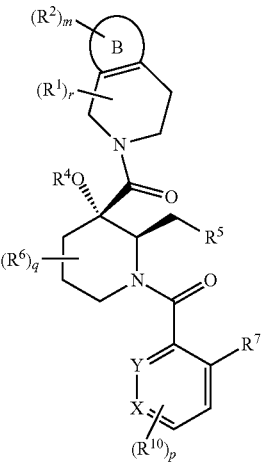

16 Claims, No Drawings

(56) References Cited

FOREIGN PATENT DOCUMENTS

| WO | WO2005110996 | | 11/2005 |
|---|---|---|---|
| WO | WO2007070398 | A1 | 6/2007 |
| WO | WO2011023677 | | 3/2011 |
| WO | WO2011046771 | A1 | 4/2011 |
| WO | WO2011058766 | A1 | 5/2011 |
| WO | WO2011098398 | | 8/2011 |

OTHER PUBLICATIONS

Blaydes, Tolerance of high leels of wild-type p53 in transformed epithelial cells dependent on auto-regulation by mdm-2, Oncogene, 1997, 1859-1868, 14.

Bottger, Identification of novel mdm2 binding peptides by phage display, Oncogene, 1996, 2141-2147, 13.

Cannon, J.G., Analog Design, Burger's Medicinal Chemistry and Drug Discovery, Chapter Nineteen Fifth Ed., 1995, 783-802, 1, Wiley-Interscience.

Chene, Inhibiting the p53-MDM2 interaction: An important target for cancer therapy, Nature Reviews, 2003, 102-109, 3.

Chene, Inhibition of the p53-MDM2 interaction: Targeting a protein-protein Interface, Molecular Cancer Research, 2004, 20-28, 2.

Ding et al., Emerging cancer therapeutic opportunities target DNA-repair systems, Trends in Pharmacological Sciences, 2006, 338-344, 27-6.

Ding, Structure-Based Design of Potent Non-Peptide MDM2 Inhibitors, J. Am. Chem. Soc., 2005, 10130-10131, 127-29.

Ding, Structure-Based Design of Spiro-oxindoles as Potent, Specific Small-Molecule Inhibitors of the MDM2-p53 Interaction, Journal of Medicinal Chemistry, 2006, 3432-3435, 49-12.

Donehower, Mice deficient for p53 are developmentally normal but susceptible to spontaneous tumours, Nature, Mar. 19, 1992, 215-221, 356.

Dorwald, Side reactions in Organic Synthesis: A Guide to Successful Synthesis Design, 2005, Chapter 1.

Duncan, Isolation and Structure Elucidation of chlorofusin, a Novel p53-MDM2 Antagonist from a *Fusarium* sp., J. Am. Chem. Soc., 2001, 554-560, 123-4.

Fotouhi, Small Molecule Inhibitors of p53/MDM2 Interaction, Current Topics in Medicinal Chemistry, 2005, 159-165, 5-2.

Freedman, Nuclear Export Is Required for Degradation of Endogenous p53 by MDM2 and Human Papillomavirus E6, Molecular and Cellular Biology, 1988, 7288-7293, 18-12.

Galatin, A Nonpeptidic Sulfonamide Inhibits the p53-mdm2 Interaction and Activates p53-Dependent Transcription in mdm2-Overexpressing Cells, J. Med. Chem., 2004, 4163-4165, 47-17.

Grasberger, Discovery and Cocrystal Structure of Benzodiazepinedione HDM2 Antagonists that Activate p53 in Cells, J. Med. Chem., 2005, 909-912, 48-4.

Hainaut, Database of p53 gene somatic mutations in human tumors and cell lines: updated compilation and future prospects, Nucleic Acids Research, 1997, 151-157, 25-1.

Hall, Genetic Alterations of Cyclins, Cyclin-Dependent Kinases, and Cdk Inhibitors in Human Cancer, Advances in Cancer Research, 1996, 67-108, 68.

Honda, Activity of MDM2, a ubiquitin ligase, toward p53 or itself is dependent on the Ring finger domain of the ligase, Oncogene, 2000, 1473-1476, 19.

Honda, Oncoprotein MDM2 is a ubiquitin ligase E3 for tumor suppressor p53, FEBS Letters, 1997, 25-27, 420.

Horig et al., From bench to clinic and back: Perspective on the 1st IQPC Translational Research Conference, Journal of Translational Medicine, 2004, 1-8, 2-44, BioMed Central.

Jordan, VC, Tamoxifen: A Most Unlikely Pioneering Medicine, Nature Reviews: Drug Discovery, 2003, 205-213, 2.

Ko, p53: puzzle and paradigm, Genes & Development, 1996, 1054-1072, 10.

Kojima, MDM2 antagonists induce p53-dependent apoptosis in AML: implications for leukemia therapy, Blood, Nov. 1, 2005, 3150-3159, 106-9.

Kussie, Paul H., Structure of the MDM2 Oncoprotein Bound to the p53 Tumor Suppressor Transactivation Domain, Science, 1996, 948-953, 274, WO.

Levine, p53, the Cellular Gatekeeper for Growth and Division, Cell, Feb. 7, 1997, 323-331, 88.

Lu, Discovery of a Nanomolar Inhibitor of the Human Murine Double Minute 2 (MDM2)-p53 Interaction through an Integrated, Virtual Database Screening Strategy, Journal of Medicinal Chemistry, 2006, 3759-3762, 49-13.

May, Twenty years of p53 research: structural and functional aspects of the p53 protein, Oncogene, 1999, 7621-7636, 18.

Momand, MDM2—master regulator of the p53 tumor suppressor protein, Gene, 2000, 15-29, 242.

Momand, The mdm-2 Oncogene Product Forms a Complex with the p53 Protein and Inhibits p53—Mediated Transactivation, Cell, Jun. 26, 1992, 1237-1245, 69.

Oliner, Oncoprotein MDM2 conceals the activation domain of tumour suppressor p53, Letters to Nature, Apr. 29, 1993, 857-860, 362.

Oren, Decision making by p53: life, death and cancer, Cell Death and Differentiation, 2003, 431-442, 10.

Roth, Nucleo-cytoplasmic shuttling of the hdm2 oncoprotein regulates the levels of the p53 protein via a pathway used by the human immunodeficiency virus rev protein, The EMBO Journal, 1998, 554-564, 17-2.

Schafer, S. et al., Failure is an option: learning from unsuccessful proof-of-concept trial, Drug Discovery Today, 2008, 913-916, 13-21.

Sherr, The Pezcoller Lecture: Cancer Cell Cycles Revisited, Cancer Research, Jul. 15, 2000, 3689-3695, 60.

Stoll, Chalcone Derivatives Antagonize Interactions between the Human Oncoprotein MDM2 and p53, Biochemistry, 2001, 336-344, 40-2.

Tao, Nucleocytoplasmic shuttling of oncoprotein Hdm2 is required for Hdm2-mediated degradation of p53, Proc. Natl. Acad. Sci., USA, Mar. 1999, 3077-3080, 96.

Vassilev, In Vivo Activation of the p53 Pathway by Small-Molecule antagonists of MDM2, Science, Feb. 6, 2004, 844-848, 303.

Vassilev, p53 Activation by Small Molecules: Application in Oncology, Journal of Medicinal Chemistry, Jul. 14, 2005, 4491-4499, 48-14.

Vippagunta, S.R. et al., Crystalline Solids, Advanced Drug Delivery Reviews, 2001, 3-26, 48.

Wolff, M.E., Burger's Medicinal Chemistry and drug Discovery, vol. 1: Principle and Practice, 1995, 975-977, 1, John Wiley & Sons, New York.

Wu, The p53-mdm-2 autoregulatory feedback loop, Genes & Development, 1993, 1126-1132, 7.

Yang, Small molecule inhibitors of HDM2 ubiquitin ligase activity stabilize and activate p53 in cells, Cancer Cell, Jun. 2005, 547-559, 7.

Zheleva, The p53-Mdm2 Pathway: Targets for the Development of New Anticancer Therapeutics, Mini Reviews in Medicinal Chem, 2003, 257-270, 3-3.

SUBSTITUTED PIPERIDINES AS HDM2 INHIBITORS

This application is a 371 of PCT/US12/69996 filed Dec. 17, 2012 which claims benefit of 61/578,589 filed Dec. 21,2011.

FIELD OF THE INVENTION

The present invention relates to novel compounds useful as Human Double Minute 2 ("HDM2") protein inhibitors, regulators or modulators, pharmaceutical compositions containing the compounds and potential methods of treatment using the compounds and compositions to potentially treat diseases such as, for example, cancer, diseases involving abnormal cell proliferation, and diseases caused by inadequate p53 levels.

BACKGROUND OF THE INVENTION

The tumor suppressor protein p53 plays a central role in maintaining the integrity of the genome in a cell by regulating the expression of a diverse array of genes responsible for DNA repair, cell cycle and growth arrest, and apoptosis [May et al., *Oncogene* 18 (53) (1999) p. 7621-7636; Oren, *Cell Death Differ.* 10 (4) (2003) p. 431-442, Hall and Peters, *Adv. Cancer Res.*, 68: (1996) p. 67-108; Hainaut et al., *Nucleic Acid Res.*, 25: (1997) p. 151-157; Sherr, *Cancer Res.*, 60: (2000) p. 3689-95]. In response to oncogenic stress signals, the cell triggers the p53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., *Genes & Devel.* 10: (1996) p. 1054-1072; Levine, *Cell* 88: (1997) p. 323-331]. The loss of the safeguard functions of p53 predisposes damaged cells to progress to a cancerous state. Inactivating p53 in mice consistently leads to an unusually high rate of tumors [Donehower et al., *Nature,* 356: (1992) p. 215-221].

The p53 transcription factor promotes the expression of a number of cell cycle regulatory genes, including its own negative regulator, the gene encoding the Mouse Double Minute 2 (MDM2) protein [Chene, *Nature Reviews Cancer* 3: (2003) p. 102-109; Momand, *Gene* 242 (1-2): (2000) p. 15-29; Zheleva et al. *Mini. Rev. Med. Chem.* 3 (3): (2003) p. 257-270]. The MDM2 protein (designated HDM2 in humans) acts to down-regulate p53 activity in an auto-regulatory manner [Wu et al, *Genes Dev.,* 7: (1993) p. 1126-1132; Bairak et al., *EMBO J,* 12: (1993) p. 461-468]. In the absence of oncogenic stress signals, i.e., under normal cellular conditions, the MDM2 protein serves to maintain p53 activity at low levels [Wu et al, *Genes Dev.,* 7: (1993) p. 1126-1132; Barak et al., *EMBO J,* 12: (1993) p. 461-468]. However, in response to cellular DNA damage or under cellular stress, p53 activity increases helping to prevent the propagation of permanently damaged clones of cells by induction of cell cycle and growth arrest or apoptosis.

The regulation of p53 function relies on an appropriate balance between the two components of this p53-MDM2 auto-regulatory system. Indeed, this balance appears to be essential for cell survival. There are at least three ways that MDM2 acts to down-regulate p53 activity. First, MDM2 can bind to the N-terminal transcriptional activation domain of p53 to block expression of p53-responsive genes [Kussie et al., *Science,* 274: (1996) p. 948-953; Oliner et al., *Nature,* 362: (1993) p. 857-860; Momand et al, *Cell,* 69: (1992) p. 1237-1245]. Second, MDM2 shuttles p53 from the nucleus to the cytoplasm to facilitate the proteolytic degradation of p53 [Roth et al, *EMBO J,* 17: (1998) p. 554-564; Freedman et al., *Mol Cell Biol,* 18: (1998) p. 7288-7293; Tao and Levine, *Proc. Natl. Acad. Sci.* 96: (1999) p. 3077-3080]. Finally, MDM2 possesses an intrinsic E3 ligase activity for conjugating ubiquitin to p53 for degradation within the ubiquitin-dependent 26S proteosome pathway [Honda et al., *FEBS Lett,* 420: (1997) p. 25-27; Yasuda, *Oncogene* 19: (2000) p. 1473-1476]. Thus, MDM2 impedes the ability of the p53 transcription factor to promote the expression of its target genes by binding p53 in the nucleus. Attenuating the p53-MDM2 auto-regulatory system can have a critical effect on cell homeostasis. Consistently, a correlation between the overexpression of MDM2 and tumor formation has been reported [Chene, *Nature* 3: (2003) p. 102-109]. Functional inactivation of wild type p53 is found in many types of human tumors. Restoring the function of p53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with p53 [Chene, *Nature* 3: (2003) p. 102-109]. Antibodies, peptides, and antisense oligonucleotides have been demonstrated to destroy the p53-MDM2 interaction, which would release p53 from the negative control of MDM2, leading to activation of the p53 pathway allowing the normal signals of growth arrest and/or apoptosis to function, which offers a potential therapeutic approach to treating cancer and other diseases characterized by abnormal cell proliferation. [See, e.g., Blaydes et al., *Oncogene* 14: (1997) p. 1859-1868; Bottger et al., *Oncogene* 13 (10): (1996) p. 2141-2147].

Small molecules, said to antagonize the p53-MDM2 interaction, have been described. WO 00/15657 (Zeneca Limited) describes piperizine-4-phenyl derivatives as inhibitors of the interaction between MDM2 and p53. Grasberger et al. (*J. Med. Chem.,* 48 (2005) p. 909-912) (Johnson & Johnson Pharmaceutical Research & Development L.L.C.) describes discovery and co-crystal structure of benzodiazepinedione as HDM2 antagonists that activate p53 in cells. Galatin et al. (*J. Med. Chem.* 47 (2004) p. 4163-4165) describes a nonpeptidic sulfonamide inhibitor of the p53-MDM2 interaction and activator of p53 dependent transcription in MDM2-overexpressing cells.

U.S. Pub. No. 2004/0259867 A1 and 2004/0250884 A1 describes Cis-imidazoles (Hoffmann La Roche Inc.) and WO2005/110996A1 and WO 03/051359 describes Cis-Imidazolines (Hoffmann La Roche Inc.) as compounds that inhibit the interaction of MDM2 with p53-like peptides resulting in antiproliferation. WO 2004/080460 A1 describes substituted piperidine compounds as MDM2-p53 inhibitors for treating cancer (Hoffmann La Roche Inc.). EP 0947494 A1 describes phenoxy acetic acid derivatives and phenoxy methyltetrazole that act as antagonists of MDM2 and interfere with the protein-protein interaction between MDM2 and p53, which results in anti-tumor properties (Hoffmann La Roche Inc.). Duncan et al., *J. Am. Chem. Soc.* 123 (4): (2001) p. 554-560 describes a p-53-MDM2 antagonist, chlorofusin, from a *Fusarium* Sp. Stoll et al., *Biochemistry* 40 (2) (2001) p. 336-344 describes chalcone derivatives that antagonize interactions between the human oncoprotein MDM2 and p53.

There is a need for effective inhibitors of the HDM2 or MDM2 protein in order to treat or prevent cancer, other disease states associated with cell proliferation, diseases associated with HDM2, or diseases caused by inadequate p53 activity. The present application discloses compounds that have potency in inhibiting or antagonizing the HDM2-p53 and MDM2-p53 interaction and/or activating p53 proteins in cells.

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, methods of treatment or prevention of one or more diseases associated with HDM2, MDM2, p53, or p53 peptides by administering such compounds or pharmaceutical compositions.

SUMMARY OF THE INVENTION

In its many embodiments, the present invention provides a novel class of substituted piperidine compounds, pharmaceutical compositions comprising one or more said compounds, and methods for using said compounds for treating or preventing a disease associated with the HDM2 protein.

Accordingly, in one aspect the present invention provides a compound of Formula I:

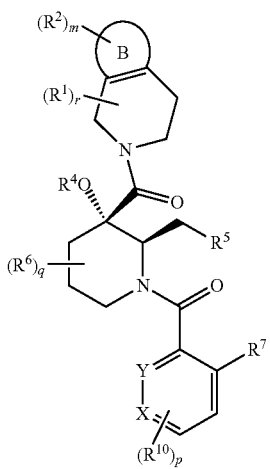

I

DETAILED DESCRIPTION OF THE INVENTION

In one embodiment, the present invention provides compounds illustrated as Formula I, as described above, or pharmaceutically acceptable salts or solvates thereof. Certain compounds of the invention unexpectedly demonstrate reduced CYP450 inhibitory liability (3A4) and/or good inhibition of HDM2 protein.

Accordingly, in one aspect the present invention provides a compound of Formula I:

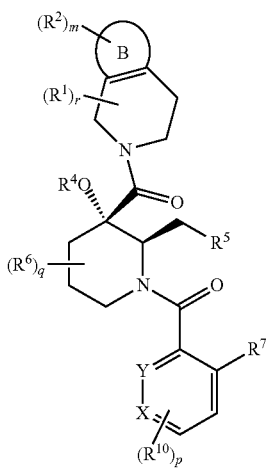

I wherein:
X is $CR^3$ or N;
Y is $CR^3$ or N;
Ring B is a 5 or 6-membered heteroaryl ring or phenyl;

$R^1$ is independently selected from H, halo, CN, $(CR^a_2)_n R^8$, $-N(R^8)_2$, $(C_3-C_6)$cycloalkylCOOR$^8$, $(CR^a_2)_n$COOR$^8$, $(CR^a_2)_n$C(O)NR$^a$R$^8$, $(CR^a_2)_n$C(O)NR$^a$SO$_2$R$^8$, $(CR^a_2)_n$NR$^a$C(O)R$^8$, $(CR^a_2)_n$OR$^8$, $(CR^a_2)_n$C(O)R$^8$ and $(CR^a_2)_n$O$(CR^a_2)_n$COOR$^a$;

$R^2$ is independently selected from H, halo, CN, amide, aryl, heterocyclic, $(CR^a_2)_n$COOR$^8$, $-N(R^a)_2$, $(CR^a_2)_n$OR$^a$, $(CR^a_2)_n$SR$^a$ and $-SO_2R^a$, wherein the aryl or heterocyclic is optionally substituted with one to three substituents selected from cyano, hydroxy, amide, halo and methoxy;

Provided that $R^1$ and $R^2$ are not both H;

$R^3$ is independently selected from the group consisting of: H, cyano, hydroxy, and alkoxy;

$R^4$ is heteroaryl which is optionally substituted with halo, halo-$(C_1-C_6)$alkyl, $(C_1-C_6)$alkyl, or $-(C_1-C_6)$alkoxy;

$R^5$ is H, $(C_1-C_6)$alkyl, $(C_1-C_6)$alkenyl, $(C_1-C_6)$alkynyl, $(CR^b_2)_t$COOH, $(CR^b_2)_t N(R^9)_2$, $(CR^b_2)_t$OR$^9$ or $(CR^b_2)_t R^9$;

$R^6$ is independently $(C_1-C_6)$alkyl;

$R^7$ is haloalkyl, $-NR^a C(O)R^a$, or $C(O)N(R^a)_2$;

$R^8$ is independently selected from H, halo, OH, CN, $(C_1-C_6)$alkyl, $(C_3-C_8)$cycloalkyl, heterocylic, heterocyclenyl, heteroaryl, $(C_1-C_6)$alkylheterocyclic, $(C_1-C_6)$alkylheterocyclenyl and $(C_1-C_6)$alkylheteroaryl, wherein said alkyl, cycloalkyl, heterocyclic, heterocyclenyl and heteroaryl is optionally substituted with $(C_1-C_6)$alkyl, $(CR^a_2)_n$OR$^a$, $-N(R^a)_2$, $(CR^a_2)_n$COOR$^a$, $(CR^a_2)_n$C(O)NR$^a$R$^a$, or $(CR^a_2)_n$NR$^a$C(O)R$^a$.

$R^9$ is independently H, $(C_1-C_6)$alkyl, $(C_3-C_8)$cycloalkyl, heteroaryl, heterocyclenyl or heterocyclic, wherein the alkyl, cycloalkyl, heteroaryl, heterocyclenyl and heterocyclic is optionally substituted with $(C_1-C_6)$alkyl, $(C_3-C_8)$cycloalkyl, $(CR^a_2)_n$COOH, or $(CR^a_2)_n$OR$^b$;

$R^{10}$ is independently $(C_1-C_6)$alkyl;

$R^a$ is independently H or $(C_1-C_6)$alkyl, wherein the alkyl is optionally substituted with $(C_0-C_6)$alkyl-OH or $-(C_0-C_6)$alkylOMe; and $R^b$ is independently H or $(C_1-C_6)$alkyl;

m is 1, 2, or 3;
n is independently 0, 1, 2, 3, 4 or 5;
p is 0, 1, or 2;
q is 0, 1, 2, or 3;
r is 1, 2 or 3;
t is 0, 1, 2 or 3.

or a pharmaceutically acceptable salt thereof.

In one embodiment,
X is $CR^3$ or N;
Y is $CR^3$ or N;
Ring B is a 5 or 6-membered heteroaryl ring or phenyl;

$R^1$ is independently selected from halo, CN, $(CR^a_2)_n R^8$, $-N(R^8)_2$, $(C_3-C_6)$cycloalkylCOOR$^8$, $(CR^a_2)_n$COOR$^8$, $(CR^a_2)_n$C(O)NR$^a$R$^8$, $(CR^a_2)_n$C(O)NR$^a$SO$_2$R$^8$, $(CR^a_2)_n$NR$^a$C(O)R$^8$, $(CR^a_2)_n$OR$^8$, $(CR^a_2)_n$C(O)R$^8$ and $(CR^a_2)_n$O$(CR^a_2)_n$COOR$^a$;

$R^2$ is independently selected from H, halo, CN, amide, aryl, heterocyclic, $(CR^a_2)_n$COOR$^8$, $-N(R^a)_2$, $(CR^a_2)_n$OR$^a$, $(CR^a_2)_n$SR$^a$ and $-SO_2R^a$, wherein the aryl or heterocyclic is optionally substituted with one to three substituents selected from cyano, hydroxy, amide, halo and methoxy;

$R^3$ is independently selected from the group consisting of: H, cyano, hydroxy, and alkoxy;

$R^4$ is heteroaryl which is optionally substituted with halo, halo-$(C_1-C_6)$alkyl, $(C_1-C_6)$alkyl, or $-(C_1-C_6)$alkoxy;

$R^5$ is H, $(C_1-C_6)$alkyl, $(C_1-C_6)$alkenyl, $(C_1-C_6)$alkynyl, $(CR^b_2)_t$COOH, $(CR^b_2)_t N(R^9)_2$, $(CR^b_2)_t$OR$^9$ or $(CR^b_2)_t R^9$;

$R^6$ is independently $(C_1-C_6)$alkyl;

$R^7$ is haloalkyl, $-NR^a C(O)R^a$, or $C(O)N(R^a)_2$;

R[8] is independently selected from H, halo, OH, CN, ($C_1$-$C_6$) alkyl, ($C_3$-$C_8$)cycloalkyl, heterocylic, heterocyclenyl, heteroaryl, ($C_1$-$C_6$)alkylheterocyclic, ($C_1$-$C_6$)alkylheterocyclenyl and ($C_1$-$C_6$)alkylheteroaryl, wherein said alkyl, cycloalkyl, heterocyclic, heterocyclenyl and heteroaryl is optionally substituted with ($C_1$-$C_6$)alkyl, $(CR^a_2)_nOR^a$, $-N(R^a)_2$, $(CR^a_2)_nCOOR^a$, $(CR^a_2)_nC(O)NR^aR^a$, or $(CR^a_2)_nNR^aC(O)R^a$.

R[9] is independently H, ($C_1$-$C_6$)alkyl, ($C_3$-$C_8$)cycloalkyl, heteroaryl, heterocyclenyl or heterocyclic, wherein the alkyl, cycloalkyl, heteroaryl, heterocyclenyl and heterocyclic is optionally substituted with ($C_1$-$C_6$)alkyl, ($C_3$-$C_8$)cycloalkyl, $(CR^a_2)_nCOOH$, or $(CR^a_2)_nOR^b$;

R[10] is independently ($C_1$-$C_6$)alkyl;

$R^a$ is independently H or ($C_1$-$C_6$)alkyl, wherein the alkyl is optionally substituted with ($C_0$-$C_6$)alkyl-OH or —($C_0$-$C_6$)alkylOMe; and $R^b$ is independently H or ($C_1$-$C_6$)alkyl;

m is 1, 2, or 3;
n is independently 0, 1, 2, 3, 4 or 5;
p is 0, 1, or 2;
q is 0, 1, 2, or 3;
r is 1, 2 or 3;
t is 0, 1, 2 or 3.

In another embodiment,
X is CR[3] or N;
Y is CR[3] or N;
Ring B is a 5 or 6-membered heteroaryl ring or phenyl;
R[1] is independently selected from H, halo, CN, $(CR^a_2)_nR^8$, $-N(R^8)_2$, ($C_3$-$C_6$)cycloalkylCOOR[8], $(CR^a_2)_nCOOR^8$, $(CR^a_2)_nC(O)NR^aR^8$, $(CR^a_2)_nC(O)NR^aSO_2R^8$, $(CR^a_2)_nNR^aC(O)R^8$, $(CR^a_2)_nOR^8$, $(CR^a_2)_nC(O)R$ and $(CR^a_2)_nO(CR^a_2)_nCOOR^a$.

R[2] is independently selected from H, halo, CN, amide, aryl, heterocyclic, $(CR^a_2)_nCOOR^8$, $-N(R^a)_2$, $(CR^a_2)_nOR^a$, $(CR^a_2)_nSR^a$ and $-SO_2R^a$, wherein the aryl or heterocyclic is optionally substituted with one to three substituents selected from cyano, hydroxy, amide, halo and methoxy;

R[3] is independently selected from the group consisting of: H, cyano, hydroxy, and alkoxy;

R[4] is thienyl, optionally substituted with $CF_3$, $CBr_3$, $CCl_3$, $CH_3$, Br, Cl, F, or —$OCH_3$.

R[5] is H, ($C_1$-$C_6$)alkyl, ($C_1$-$C_6$)alkenyl, ($C_1$-$C_6$)alkynyl, $(CR^b_2)_tCOOH$, $(CR^b_2)_tN(R^9)_2$, $(CR^b_2)_tOR^9$ or $(CR^b_2)_tR^9$;

R[6] is independently ($C_1$-$C_6$)alkyl;

R[7] is haloalkyl, $-NR^aC(O)R^a$, or $C(O)N(R^a)_2$;

R[8] is independently selected from H, halo, OH, CN, ($C_1$-$C_6$) alkyl, ($C_3$-$C_8$)cycloalkyl, heterocylic, heterocyclenyl, heteroaryl, ($C_1$-$C_6$)alkylheterocyclic, ($C_1$-$C_6$)alkylheterocyclenyl and ($C_1$-$C_6$)alkylheteroaryl, wherein said alkyl, cycloalkyl, heterocyclic, heterocyclenyl and heteroaryl is optionally substituted with ($C_1$-$C_6$)alkyl, $(CR^a_2)_nOR^a$, $-N(R^a)_2$, $(CR^a_2)_nCOOR^a$, $(CR^a_2)_nC(O)NR^aR^a$, or $(CR^a_2)_nNR^aC(O)R^a$.

R[9] is independently H, ($C_1$-$C_6$)alkyl, ($C_3$-$C_8$)cycloalkyl, heteroaryl, heterocyclenyl or heterocyclic, wherein the alkyl, cycloalkyl, heteroaryl, heterocyclenyl and heterocyclic is optionally substituted with ($C_1$-$C_6$)alkyl, ($C_3$-$C_8$)cycloalkyl, $(CR^a_2)_nCOOH$, or $(CR^a_2)_nOR^b$;

R[10] is independently ($C_1$-$C_6$)alkyl;

$R^a$ is independently H or ($C_1$-$C_6$)alkyl, wherein the alkyl is optionally substituted with ($C_0$-$C_6$)alkyl-OH or —($C_0$-$C_6$)alkylOMe; and $R^b$ is independently H or ($C_1$-$C_6$)alkyl;

m is 1, 2, or 3;
n is independently 0, 1, 2, 3, 4 or 5;
p is 0, 1, or 2;
q is 0, 1, 2, or 3;
r is 1, 2 or 3;
t is 0, 1, 2 or 3.

In one embodiment, R[4] is thienyl, optionally substituted with $CF_3$, $CBr_3$, $CCl_3$, $CH_3$, Br, Cl, F, or —$OCH_3$.

In another embodiment, R[4] is

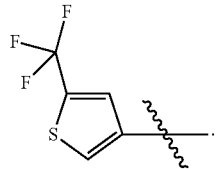 [SMILES: *c1csc(C(F)(F)F)c1]

The present invention also provides compounds under Formula II,

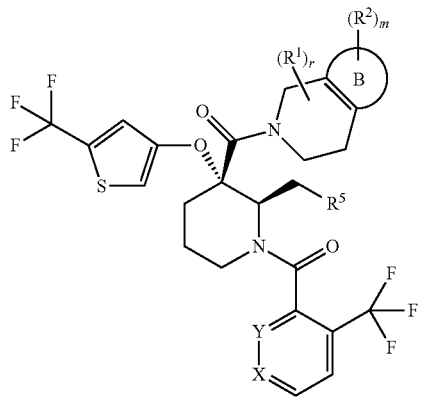

wherein:
X is CH and Y is N, or X is N and Y is CH;
Ring B is a 5 or 6-membered heteroaryl ring or phenyl;
R[1] is independently selected from H, halo, CN, $(CR^a_2)_nR^8$, $-N(R^8)_2$, $C_3$-$C_6$cycloalkylCOOR[8], $(CR^a_2)_nCOOR^8$, $(CR^a_2)_nC(O)NR^aR^8$, $(CR^a_2)_nC(O)NR^aSO_2R^8$, $(CR^a_2)_nNR^aC(O)R^8$, $(CR^a_2)_nOR^8$, $(CR^a_2)_nC(O)R^8$ and $(CR^a_2)_nO(CR^a_2)_nCOOR^a$;

R[2] is independently selected from H, halo, CN, amide, aryl, heterocyclic, $(CR^a_2)_nCOOR^8$, $-N(R^a)_2$, $(CR^a_2)_nOR^a$, $(CR^a_2)_nSR^a$ and $-SO_2R^a$, wherein the aryl or heterocyclic is optionally substituted with one to three substituents selected from cyano, hydroxy, amide, halo and methoxy;

R[5] is H, ($C_1$-$C_6$)alkyl, ($C_1$-$C_6$)alkenyl, ($C_1$-$C_6$)alkynyl, $(CR^b_2)_tCOOH$, $(CR^b_2)_tN(R^9)_2$, $(CR^b_2)_tOR^9$ or $(CR^b_2)_tR^9$;

R[8] is independently selected from H, halo, OH, CN, ($C_1$-$C_6$) alkyl, ($C_3$-$C_8$)cycloalkyl, heterocylic, heterocyclenyl, heteroaryl, ($C_1$-$C_6$)alkylheterocyclic, ($C_1$-$C_6$)alkylheterocyclenyl and ($C_1$-$C_6$)alkylheteroaryl, wherein said alkyl, cycloalkyl, heterocyclic, heterocyclenyl and heteroaryl is optionally substituted with ($C_1$-$C_6$)alkyl, $(CR^a_2)_nOR^a$, $-N(R^a)_2$, $(CR^a_2)_nCOOR^a$, $(CR^a_2)_nC(O)NR^aR^a$, or $(CR^a_2)_nNR^aC(O)R^a$.

R[9] is independently H, ($C_1$-$C_6$)alkyl, ($C_3$-$C_8$)cycloalkyl, heteroaryl, heterocyclenyl or heterocyclic, wherein the alkyl, cycloalkyl, heteroaryl, heterocyclenyl and heterocyclic is optionally substituted with ($C_1$-$C_6$)alkyl, ($C_3$-$C_8$)cycloalkyl, $(CR^a_2)_nCOOH$, or $(CR^a_2)_nOR^b$, $R^a$ is independently H or ($C_1$-$C_6$)alkyl, wherein the alkyl is optionally substituted with ($C_0$-$C_6$)alkyl-OH or ($C_0$-$C_6$)alkylOMe; and $R^b$ is independently H or ($C_1$-$C_6$)alkyl;

m is 1 or 2;
n is independently 0, 1, 2, 3 or 4;
r is 1 or 2;
t is 0, 1 or 2;

or a pharmaceutically acceptable salt thereof.

In one embodiment, R[1] and R[2] are not both H.

The present invention also provides compounds under Formula III:

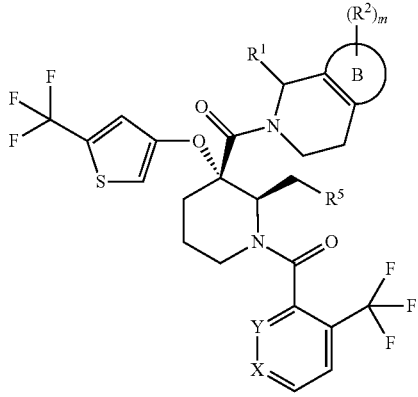

and all other substituents are as defined above.

The present invention also provides compounds under Formula IV:

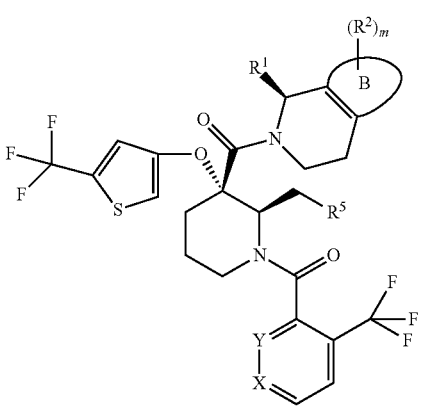

and all other substituents are as defined above.

The present invention also provides compounds under Formula V:

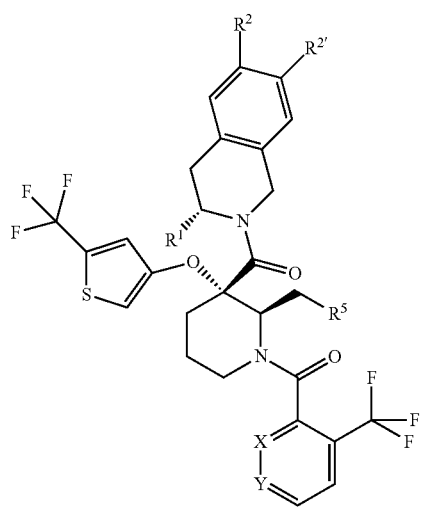

Wherein
R² and R²' are independently H, Br or Cl,
and all other substituents are as defined above.

The present invention also provides compounds under Formula VA:

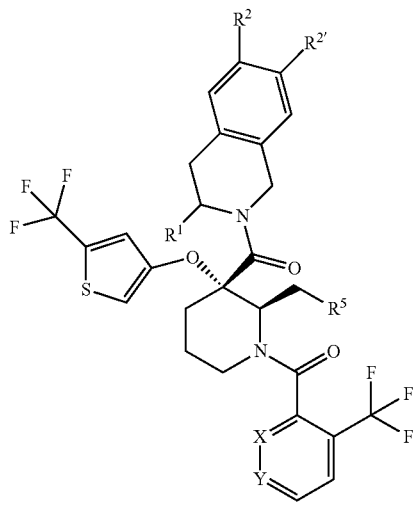

R² and R²' are independently H, Br or Cl,
and all other substituents are as defined above.

The present invention also provides compounds under Formula VI:

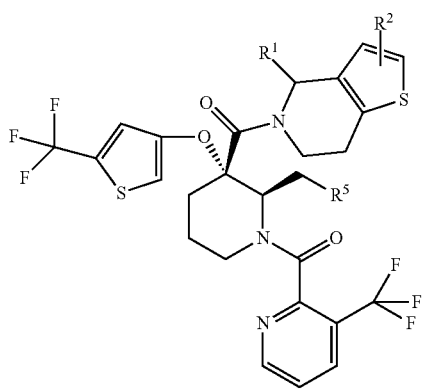

In one aspect of the above invention, $R^1$ is selected from $(C_3-C_6)$cycloalkylCOOR$^a$, $(CR^a_2)_n$COOR$^a$, $(CR^a_2)_n$O $(CR^a_2)_n$COOR$^a$, and $(CR^a_2)_n$C(O)NR$^a$SO$_2$R$^8$. In one embodiment, $R^1$ is $(CR^a_2)_n$COOR$^a$. In another embodiment, $R^1$ is $(CH_2)_n$COOH, and n is 2 or 3. In a further embodiment, $R^1$ is $(CH_2)_n$COOH, and n is 2. In yet another embodiment, $R^1$ is —CH$_2$C(CH$_3$)$_2$COOH, —CH(CH$_3$)CH$_2$COOH, -cyclopentyl-COOH, or CH$_2$OCH$_2$COOH.

In yet another embodiment, $R^1$ is H, —CH$_2$C(CH$_3$)$_2$COOH, CH$_2$CH(CH(CH$_3$)$_2$)COOH, CH$_2$CH(CH$_2$(CH$_3$))COOH, —CH$_2$CH(CH$_3$)COOH, —CH$_2$CH(OH)COOH, —CH(CH$_3$)CH$_2$COOH, -cyclopentyl-COOH, CH$_2$OCH$_2$COOH, COOH, CH$_2$COOH, CH$_2$CH$_2$COOH, CH$_2$CH$_2$CH$_2$COOH, CH$_2$CH$_2$CH$_2$CH$_2$COOH, $(CR^a_2)_n$C(O)NR$^a$SO$_2$R$^a$, methoxymethyl, morpholinylmethyl, or C(O)NH$_2$. In yet another embodiment, $R^1$ is -cyclopentyl-COOH, $(CR^a_2)_n$COOH, $(CR^a_2)_n$O(CR$^a_2$)$_n$COOH, $(CR^a_2)_n$C(O)NR$^a$SO$_2$R$^a$, methoxymethyl, morpholinylmethyl, or C(O)NH$_2$, wherein n is 0, 1, 2, 3 or 4.

In another aspect of the above invention, $R^2$ is halo. In another embodiment, $R^2$ is Cl or Br.

In a further aspect of the above invention, $R^5$ is methyl, $CH(CH_3)COOH$, $CH_2CH_2COOH$ or 5-6 membered heterocyclic, said heterocyclic optionally substituted with $(C_1-C_3)$ alkyl, $(C_3-C_5)$cycloalkyl, $(CR^a_2)_nCOOH$, or $(CR^a_2)_nOR^b$. In one embodiment, the heterocyclic is morpholinyl, pyrrolidinyl, piperdinyl, or piperzinyl. In another embodiment, the heterocylic is

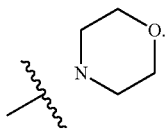

In a further aspect of the above invention, $R^8$ is selected from H, halo, OH, CN, $(C_1-C_6)$alkyl, $(C_3-C_8)$cycloalkyl, heterocylic, heteroaryl, $(C_1-C_6)$alkylheterocyclic, and $(C_1-C_6)$alkylheteroaryl, wherein said alkyl, cycloalkyl, heterocyclic and heteroaryl is optionally substituted with $(C_1-C_6)$alkyl, $(CR^a_2)_nOR^a$, —$N(R^a)_2$, $(CR^a_2)_nCOOR^a$, $(CR^a_2)_nC(O)NR^aR^a$, or $(CR^a_2)_nNR^aC(O)R^a$.

In a further aspect of the above invention, $R^9$ is independently H, $(C_1-C_6)$alkyl or heterocyclic, wherein the alkyl and heterocyclic is optionally substituted with $(C_1-C_6)$alkyl, $(C_3-C_8)$cycloalkyl, $(CR^a_2)_nCOOH$, or $(CR^a_2)_nOR^b$;

In a further aspect of the above invention, X is CH and Y is N.

In a further aspect of the above invention, r is 1.

Specific examples of the compounds of the invention include, but not limited to:

2-[(2R,3S)-3-[(7-chloro-3,4-dihydroisoquinolin-2(1H)-yl) carbonyl]-1-{[4-(trifluoromethyl)pyridin-3-yl]carbonyl}-3-{[5-(trifluoromethyl)thiophen-3-yl]oxy}piperidin-2-yl]-N,N-bis(2-methoxyethyl)ethanamine;

2-[(2R,3S)-3-[(6-chloro-3,4-dihydroisoquinolin-2(1H)-yl) carbonyl]-1-{[4-(trifluoromethyl)pyridin-3-yl]carbonyl}-3-{[5-(trifluoromethyl)thiophen-3-yl]oxy}piperidin-2-yl]-N,N-bis(2-methoxyethyl)ethanamine;

7-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-7-carbonitrile;

2-{[(2R,3S)-2-propyl-1-{[3-(trifluoromethyl)pyridin-2-yl]carbonyl}-5-{[5-(trifluoromethyl)thiophen-3-yl]oxy}piperidin-3-yl]carbonyl}-1,2,3,4-tetrahydroisoquinoline-7-carboxamide;

6-fluoro-2-{[(2R,3S)-2-(2-morpholin-4-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine;

ethyl 5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylate;

5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine;

6-chloro-1-(morpholin-4-ylmethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1-(pyrrolidin-1-ylmethyl)-1,2,3,4-tetrahydroisoquinoline;

6-chloro-1-(methoxymethyl)-2-{[(2R,3S)-2-(2-pyrrolidin-1-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-1-(methoxymethyl)-2-{[(2R,3S)-2-(2-morpholin-4-ylethl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]acetic acid;

2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-7-carboxylic acid;

2-(1-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}piperidin-4-yl)ethanol;

6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1-(methoxymethyl)-1,2,3,4-tetrahydroisoquinoline;

N-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)propanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)propanamide;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-methylpropanamide;

ethyl 2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoate;

2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoic acid;

2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-N-(1H-tetrazol-5-ylmethyl)propanamide 3-(2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-2,2-dimethylpropanoic acid;

2-chloro-4-(3-morpholin-4-ylpropyl)-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(3-pyrrolidin-1-ylpropyl)-4,5,6,7-tetrahydrothieno[3,2-c]pyridine;

2-chloro-N-methyl-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxamide;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(pyrrolidin-1-ylmethyl)-4,5,6,7-tetrahydrothieno[3,2-c]pyridine;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl)propanamide;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl)propanamide;

{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methoxy}acetic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carbonitrile;

6-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,8S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol;

(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;
3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;
3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;
3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide,
3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl)propanamide;
6-phenyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl)propanamide;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;
2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-6-thiophen-3-yl-1,2,3,4-tetrahydroisoquinoline;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethyl-N-(methylsulfonyl)propanamide;
(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanenitrile;
(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-S-yl]carbonyl}-1,2,3,4-tetrahydroisoquinolin-1-yl)acetic acid;
4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid;
4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;
6-chloro-2-{[(2R,3S)-2-propyl-1-{[3-(trifluoromethyl)pyridin-2-yl]carbonyl}-3-{[5-trifluoromethyl)thiophen-3-yl]oxy}piperidin-3-yl]carbonyl}-1,2,3,4-tetrahydroisoquinoline-1-carbonitrile,
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carbonitrile;
3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]-N-cyanopropanamide;
3-[(1S)-6-chloro-2-{[(2R,3S)-2-propyl-1-{[3-(trifluoromethyl)pyridin-2-yl]carbonyl}--{[5-(trifluoromethyl)thiophen-3-yl]oxy}piperidin-3-yl]carbonyl}-1,2,3,4-tetrahydroisoquinolin-1-yl]-N-cyanopropanamide;
4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one;
1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol;
N,N-dimethyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine;
4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one;
1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol;
5,6-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
6,7-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
6-(methylsulfanyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carboxamide;

6-(methylsulfonyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-(4-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperazin-1-yl)ethanol;

2-{4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;

2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;

2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;

[(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)cyclopentanecarboxylic acid;

[(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid;

1-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid;

1-{3-[(1S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-8-yl]carbonyl}-1,2,3,4-tetrahydroisoquinoline-1-carboxylic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol;

6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;

6-chloro-1-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;

6-fluoro-2-[(2-propyl-3-[4-(trifluoromethoxy)phenoxy]-1-{[3-(trifluoromethyl)pyridin-2-yl]carbonyl}piperidin-3-yl)carbonyl]-1,2,3,4-tetrahydroisoquinoline;

3-[(1S)-6-chloro-2-{[(2R,3S)-2-propyl-3-[4-(trifluoromethoxy)phenoxy]-1-{[3-(trifluoromethyl)pyridin-2-yl]carbonyl}piperidin-3-yl]carbonyl}-1,2,3,4-tetrahydroisoquinolin-1-yl]propanoic acid;

N-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine;

6-chloro-2-{[(2R,3S)-2-prop-en-1-yl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

6-chloro-2-{[(2R,3S)-2-[2-(4-ethylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,3S)-2-[2-(4-methylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,3S)-2-{2-[4-(cyclopropylmethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]-N-(2-methoxyethyl)-N-methylethanamine;

6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-(1-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}piperidin-4-yl)-2-methylpropanoic acid;

[(3S)-2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-3-yl]methanol;

2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-8-ol;

(2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

(3R)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

(3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

5-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]pentanoic acid;

3-[(3S)-7-fluoro-2-{[(2R,3S)-2-propyl-1-{[3-(trifluoromethyl)pyridin-2-yl]carbonyl}-3-([5-(trifluoromethyl)thiophen-3-yl]oxy}piperidin-3-yl]carbonyl}-1,2,3,4-tetrahydroisoquinolin-3-yl]propanoic acid;

3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid;

(3R)-6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N,N-dimethylpropanamide;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-methylpropanamide;

(2S)-3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-methylpropanoic acid;

7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

(3S)-6-chloro-3-(3-fluoropropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]acetic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-hydroxypropanamide;

4-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid;

3-[(3R)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-(methylsulfonyl)propanamide;

1-{[(3R)-6-fluoro-2-{[(2R,3S)-2-propyl-1-{[8-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-4-ol;

(3R)-6-fluoro-N-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxamide;

(2R)—N-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-2-methoxy-N-methylpropanamide;

N-{[(3R)-6-chloro-2-{[(2R,3S)-2-propyl-1-{[3-(trifluoromethyl)pyridin-2-yl]carbonyl}-3-{[5-(trifluoromethyl)

thiophen-3-yl]oxy}piperidin-3-yl]carbonyl}-1,2,3,4-tet-
rahydroisoquinolin-3-yl]methyl}-N-methylpropanamide;
(2S)-2-{[(3R)-6-fluoro-2-{[(2R,3S)-2-propyl-1-{[3-(trifluo-
romethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]methyl}-3-methylbutanoic acid;
2-{[(2R,3S)-2-propyl-1-{[3-(trifluoromethyl)pyridin-2-yl]
carbonyl}-3-{[5-(trifluoromethyl)thiophen-3-yl]
oxy}piperidin-3-yl]carbonyl}-1,2,3,4-tetrahydroiso-
quinoline-4-carboxylic acid;
(3S)-6-chloro-3-(3-morpholin-4-ylpropyl)-2-{[(2R,3S)-2-
propyl-1-{[3-(trifluoromethyl)pyridin-2-yl]carbonyl}-3-
{[5-(trifluoromethyl)thiophen-3-yl]oxy}piperidin-3-yl]
carbonyl}-1,2,3,4-tetrahydroisoquinoline;
(3S)-6-chloro-3-{3-[(2S)-2-(methoxymethyl)pyrrolidin-1-
yl]propyl}-2-{[(2R,3S)-2-propyl-1-{[3-(trifluoromethyl)
pyridin-2-yl]carbonyl}-3-{[5-(trifluoromethyl)thiophen-
3-yl]oxy}piperidin-3-yl]carbonyl}-1,2,3,4-
tetrahydroisoquinoline;
3-[(3R)-6,7-difluoro-2-{[(2R,3S)-2-propyl-1-{[3-(trifluo-
romethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]propanoic acid;
(2R)—N-{[(3S)-6-fluoro-2-{[(2R,3S)-2-propyl-1-{[3-(trif-
luoromethyl)pyridin-2-yl]carbonyl}-3-{[5-(trifluorom-
ethyl)thiophen-3-yl]oxy}piperidin-3-yl]carbonyl}-1,2,3,
4-tetrahydroisoquinolin-3-yl]methyl}-2-hydroxy-N-
methylpropanamide;
2,2-difluoro-N-{[(3S)-6-fluoro-2-{[(2R,3S)-2-propyl-1-
{[3-(trifluoromethyl)pyridin-2-yl]carbonyl}-3-{[5-(trif-
luoromethyl)thiophen-3-yl]oxy}piperidin-3-yl]carbo-
nyl}-1,2,3,4-tetrahydroisoquinolin-3-yl]methyl}-N-me-
thylacetamide;
(3S)-6-fluoro-3-[(4-methylpiperazin-1-yl)carbonyl]-2-
{[(2R,3S)-2-propyl-1-{[3-(trifluoromethyl)pyridin-2-yl]
carbonyl}-3-{[5-(trifluoromethyl)thiophen-3-yl]
oxy}piperidin-3-yl]carbonyl}-1,2,3,4-tetrahydroiso-
quinoline;
(2R)-3-[(3S)-6-chloro-2-{[(2R,3S)-2-propyl-1-{[3-(trifluo-
romethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]-2-(methoxymethyl)propanoic
acid;
1-{[(3S)-6-fluoro-2-{[(2R,3S)-2-propyl-1-{[3-(trifluorom-
ethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]methyl}piperidin-4-ol;
(2R)—N-{2-[(3R)-6-fluoro-2-{[(2R,3S)-2-propyl-1-{[3-
(trifluoromethyl)pyridin-2-yl]carbonyl}-3-{[5-(trifluo-
romethyl)thiophen-3-yl]oxy}piperidin-3-yl]carbonyl}-1,
2,3,4-tetrahydroisoquinolin-3-yl]ethyl}-2-hydroxy-N-
methylpropanamide;
(2S)-3-[(3R)-6-chloro-2-{[(2R,3S)-2-propyl-1-{[3-(trifluo-
romethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]-2-hydroxypropanoic acid;
(2S)-2-{[(3S)-6-chloro-2-{[(2R,3S)-2-propyl-1-{[3-(trifluo-
romethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]methyl}butanoic acid;
(3R)-6-chloro-2-{[(2R,3S)-2-propyl-1-{[3-(trifluorom-
ethyl)pyridin-2-yl]carbonyl}-3-{[5-(trifluoromethyl)
thiophen-3-yl]oxy}piperidin-3-yl]carbonyl}-N-(tetrahy-
dro-2H-pyran-4-yl)-1,2,3,4-tetrahydroisoquinoline-3-
carboxamide;
4-[(3R)-6-fluoro-2-{[(2R,3S)-2-propyl-1-{[3-(trifluorom-
ethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]butan-2-ol;
1-{[(3R)-6-chloro-2-{[(2R,3S)-2-propyl-1-{[3-(trifluorom-
ethyl)pyridin-2-yl]carbonyl}-3-{[5-(trifluoromethyl)
thiophen-3-yl]oxy}piperidin-3-yl]carbonyl}-1,2,3,4-tet-
rahydroisoquinolin-3-yl]carbonyl}piperidin-4-ol;
(3R)-6-chloro-3-[(4-methoxypiperidin-1-yl)carbonyl]-2-
{[(2R,3S)-2-propyl-1-{[3-(trifluoromethyl)pyridin-2-yl]
carbonyl}-3-{[5-(trifluoromethyl)thiophen-3-yl]
oxy}piperidin-3-yl]carbonyl}-1,2,3,4-tetrahydroiso-
quinoline;
(3R)-1-{[(3R)-6-chloro-2-{[(2R,3S)-2-propyl-1-{[3-(trif-
luoromethyl)pyridin-2-yl]carbonyl}-3-{[5-(trifluorom-
ethyl)thiophen-3-yl]oxy}piperidin-3-yl]carbonyl}-1,2,3,
4-tetrahydroisoquinolin-3-yl]carbonyl}Piperidin-3-ol,
6-{[(2R,3S)-2-propyl-1-{[3-(trifluoromethyl)pyridin-2-yl]
carbonyl}-3-{[5-(trifluoromethyl)thiophen-3-yl]
oxy}piperidin-3-yl]carbonyl}-4,5,6,7-tetrahydrothieno[2,
3-c]pyridine-5-carboxylic acid;
2-chloro-6-{[(2R,3S)-2-propyl-1-{[3-(trifluoromethyl)pyri-
din-2-yl]carbonyl}-3-{[5-(trifluoromethyl)thiophen-3-yl]
oxy}piperidin-3-yl]carbonyl}-4,5,6,7-tetrahydrothieno[2,
3-c]pyridine-5-carboxylic acid;
6-{[(2R,3S)-2-propyl-1-{[3-(trifluoromethyl)pyridin-2-yl]
carbonyl}-3-{[5-(trifluoromethyl)thiophen-3-yl]
oxy}piperidin-3-yl]carbonyl}-4,5,6,7-tetrahydrothieno[2,
3-c]pyridine-5-carboxylic acid;
2-chloro-6-{[(2R,3S)-2-propyl-1-{[3-(trifluoromethyl)pyri-
din-2-yl]carbonyl}-3-{[5-(trifluoromethyl)thiophen-3-yl]
oxy}piperidin-3-yl]carbonyl}-4,5,6,7-tetrahydrothieno[2,
3-c]pyridine-5-carboxylic acid;
(5S)-2-bromo-N-(methylsulfonyl)-6-{[(2R,3S)-2-propyl-1-
{[3-(trifluoromethyl)pyridin-2-yl]carbonyl}-3-{[5-(trif-
luoromethyl)thiophen-3-yl]oxy}piperidin-3-yl]carbo-
nyl}-4,5,6,7-tetrahydrothieno[2,3-c]pyridine-5-
carboxamide;
6-chloro-1-(2-methylpropyl)-2-{[(2R,3S)-2-propyl-1-{[3-
(trifluoromethyl)pyridin-2-yl]carbonyl}-3-{[5-(trifluo-
romethyl)thiophen-3-yl]oxy}piperidin-3-yl]carbonyl}-1,
2,3,4-tetrahydroisoquinoline;
2-[(6-chloro-2-{[(2R,3S)-2-propyl-1-{[3-(trifluoromethyl)
pyridin-2-yl]carbonyl}-3-{[5-(trifluoromethyl)thiophen-
3-yl]oxy}piperidin-3-yl]carbonyl}-1,2,3,4-tetrahydroiso-
quinolin-1-yl)methyl]-3-methylbutanoic acid;
2-[(6-chloro-2-{[(2R,3S)-2-propyl-1-{[3-(trifluoromethyl)
pyridin-2-yl]carbonyl}-3-{[5-(trifluoromethyl)thiophen-
3-yl]oxy}piperidin-3-yl]carbonyl}-1,2,3,4-tetrahydroiso-
quinolin-1-yl)methyl]-3-methylbutanoic acid;
2-[(6-chloro-2-{[(2R,3S)-2-propyl-1-{[3-(trifluoromethyl)
pyridin-2-yl]carbonyl}-3-{[5-(trifluoromethyl)thiophen-
3-yl]oxy}piperidin-3-yl]carbonyl}-1,2,3,4-tetrahydroiso-
quinolin-1-yl)methyl]-3-methylbutanoic acid;
2-[(6-chloro-2-{[(2R,3S)-2-propyl-1-{[3-(trifluoromethyl)
pyridin-2-yl]carbonyl}-3-{[5-(trifluoromethyl)thiophen-
3-yl]oxy}piperidin-3-yl]carbonyl}-1,2,3,4-tetrahydroiso-
quinolin-1-yl)methyl]-3-methylbutanoic acid; and
[(6-chloro-2-{[(2R,3S)-2-propyl-1-{[3-(trifluoromethyl)py-
ridin-2-yl]carbonyl}-3-{[5-(trifluoromethyl)thiophen-3-
yl]oxy}piperidin-3-yl]carbonyl}-1,2,3,4-tetrahydroiso-
quinolin-1-yl)methoxy]acetic acid;
or a pharmaceutically acceptable salt thereof.

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic saturated or unsaturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

"Alkenylene" means a diradical group of an alkenyl group that is defined above. For example, "alkenylene" includes —$CH_2$—$CH_2$—CH=CH—$CH_2$, —CH=CH—$CH_2$ and the like.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylenearyl. If aryl is taken to be phenyl, this definition would include phenyl itself as well as —$CH_2$Ph, —$CH_2CH_2$Ph, $CH(CH_3)$$CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbon atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Heteroaryl groups within the scope of this definition include but are not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like.

In an embodiment, "heteroaryl" may also include "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyl and the like.

"Heterocyclyl" means a non-aromatic saturated monocyclic, bicyclic, tricyclic or spirocyclic ring system comprising up to 7 atoms in each ring. Preferably, the heterocyclyl contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

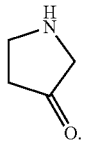

In describing the heteroatoms contained in a specified heterocyclyl group, the expression, "having one to x heteroatoms selected from the group of N, O, P and S" (wherein x is a specified integer), for example, means that each heteroatom in the specified heterocyclyl is independently selected from the specified selection of heteroatoms. Attachment of a heterocyclyl substituent can occur via a carbon atom or via a heteroatom.

"Heterocyclenyl" means a non-aromatic monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3, dihydro-2H-pyranyl, dihydrofuranyl, fluorodihydrofuranyl, 7-oxabicyclo [2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

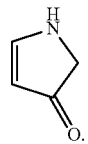

In describing the heteroatoms contained in a specified heterocyclenyl group, the expression, "having one to x heteroatoms selected from the group of N, O, P and S" (wherein x is an a specified integer), for example, means that each heteroatom in the specified heterocyclenyl is independently selected from the specified selection of heteroatoms.

It should also be noted that tautomeric forms such as, for example, the moieties:

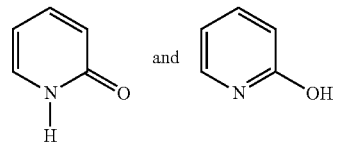 [SMILES: O=c1cccc[nH]1 ; Oc1ccccn1]

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and, suitable alkyl groups are described herein. The bond to the parent moiety is through the cycloalkyl group.

An "arylalkyl group" is an aryl group substituted with an alkyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl(which can be substituted), alkylcycloalkyl (which can be substituted), and aryloxy.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected" this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

As used herein, the term "composition" is intended to encompass a product comprising the specified ingredients in the specified amounts, as well as any product which results, directly or indirectly, from combination of the specified ingredients in the specified amounts.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Solvates

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen, bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

Pharmaceutically Acceptable Salts

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) la 201-217; Ahderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention.

Compounds of Formula I, and salts, solvates thereof, may exist in their tautomeric form (for example, as an amide or imino ether). All such tautomeric forms are contemplated herein as part of the present invention.

Pharmaceutical Compositions

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Isolation of the compound at various stages of the reaction may be achieved by standard techniques such as for example, filtration, evaporation of solvent and the like. Purification of the product and the like, may also be performed by standard techniques such as recrystallization, distillation, sublimation, chromatography, conversion to a suitable derivative. Such techniques are well known to those skilled in the art. The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the compounds of the invention as an active ingredient. The pharmaceutical compositions generally additionally comprise a pharmaceutically acceptable carrier diluent, excipient or carrier (collectively referred to herein as carrier materials).

In yet another embodiment, the present invention discloses methods for preparing pharmaceutical compositions comprising the compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of Varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount td achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one anticancer therapy and/or anti-cancer agent described below, wherein the amounts of the two or more ingredients result in desired therapeutic effect.

Capsule—refers to a special container or enclosure made of methyl cellulose, polyvinyl alcohols, or denatured gelatins Or starch for holding or containing compositions comprising the active ingredients. Hard shell capsules are typically made of blends of relatively high gel strength Nine and pork skin gelatins. The capsule itself may contain small amounts of dyes, opaquing agents, plasticizers and preservatives.

Tablet—refers to a compressed or molded solid dosage form containing the active ingredients with suitable diluents. the tablet can be prepared by compression of mixtures or granulations obtained by wet granulation, dry granulation or by compaction.

Oral gels—refer to the active ingredients dispersed or solubilized in a hydrophillic semi-solid matrix.

Powders for constitution refer to powder blends containing the active ingredients and suitable diluents which can be suspended in water or juices.

Diluent—refers to substances that usually snake up the major portion of the composition or dosage form. Suitable diluents include but are not limited to sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition.

Disintegrants—refers to materials added to the composition to help it break apart (disintegrate) and release the medicaments. Suitable disintegrants include but are not limited to modified starches such as sodium carboxymethyl starch; methylcellulose, microcrystalline celluloses and sodium croscarmellose; and sodium alginate. The amount of disintegrant in the composition can range from about 2 to about 10% by weight of the composition.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as high molecular weight polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Method of Treatment

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formula I can be inhibitors or antagonists of the Human or Mouse Double Minute 2 protein interaction with p53 protein and it can be activators of the p53 protein in cells. Furthermore, the pharmacological properties of the compounds of Formula I can be used to treat or prevent cancer, treat or prevent other disease states associated with abnormal cell proliferation, and treat or prevent diseases resulting from inadequate levels of p53 protein in cells.

Those skilled in the art will realize that the term "cancer" to be the name for diseases in which the body's cells become abnormal and divide without control.

Cancers that may be treated by the compounds, compositions and methods of the invention include, but are not limited to Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that can be useful in treating cancer. In one embodiment, the compounds of the invention are for the potential treatment of cancer.

The compounds of Formula I can be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the Central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

Due to the key role of p53 in the regulation of cellular apoptosis (cell death), the compounds of Formula I could act as agent to induce cell death which may be useful in the treatment of any disease process which features abnormal cellular proliferation eg, cancers of various origin and tissue types, inflammation, immunological disorders.

Due to the key role of HDM2 and p53 in the regulation of cellular proliferation, the compounds of Formula I could act as reversible cytostatic agents which may be useful in the treatment of any disease process which features abnormal cellular proliferation, inhibitors could act as reversible cytostatic agents which may be useful in the treatment of any disease process which features abnormal cell proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formula I may also be useful in the chemoprevention of cancer. Chemoprevention is defined as inhibiting the development of invasive cancer by either blocking the initiating mutagenic event by blocking the progression of pre-malignant cells that have already suffered an insult or inhibiting tumor relapse.

Compounds of Formula I may also be useful in inhibiting tumor angiogenesis and metastasis.

Another aspect of this invention is a potential method of treating a mammal (e.g., human) having a disease or condition associated with HDM2 by administering a therapeutically effective amount of at least one compound of Formula I, or a pharmaceutically acceptable salt or solvate of said compound to the mammal.

The invention also provides a method of inhibiting one or more HDM2 proteins in a patient in need thereof, comprising administering to the patient a therapeutically effective amount of at least one compound of claim 1 or a pharmaceutically acceptable salt or solvate thereof.

Another aspect of the present invention is a potential method of treating, or slowing the progression of a disease associated with one or more HDM2 proteins in a patient, comprising administering to a patient in need thereof, a therapeutically effective amount of at least one compound of the present invention or a pharmaceutically acceptable salt or solvate thereof.

Another aspect of the present invention is a potential method of treating, or slowing the progression of a disease associated with inadequate p53 levels in a patient, comprising administering to a patient in need thereof, a therapeutically effective amount of at least one compound of the present invention or a pharmaceutically acceptable salt or solvate thereof.

Yet another aspect of the present invention is a potential method of treating one or more diseases associated with HDM2, comprising administering to a mammal in need of such treatment an amount of a first compound, which is a compound of the present invention, or a pharmaceutically acceptable salt or solvate thereof; and an amount of at least one second compound, the second compound being an anti-cancer agent, wherein the amounts of the first compound and the second compound result in a therapeutic effect.

Another aspect of the present invention is a potential method of treating one or more diseases associated with inadequate p53 levels, comprising administering to a mammal in need of such treatment an amount of a first compound, which is a compound of the present invention, or a pharmaceutically acceptable salt or solvate thereof; and an amount of at least one second compound, the second compound being an anti-cancer agent, wherein the amounts of the first compound and the second compound result in a therapeutic effect.

Another aspect of the present invention is a potential method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt or solvate thereof.

Another aspect of the present invention is a potential method of treating, or slowing the progression of, a disease associated with inadequate p53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt or solvate thereof.

In one embodiment, the dosage is about 0.001 to 500 mg/kg of body weight/day of the compound of Formula I. In another embodiment, the dosage is about 0.01 to 25 mg/kg of body weight/day of a compound of Formula I, or a pharmaceutically acceptable salt or solvate of said compound.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Patient" includes both human and animals.

"Mammal" means humans and other mammalian animals.

Combination Therapy

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are also useful when co-administered with radiation therapy. The compounds of the present invention can be present in the same dosage unit as the anticancer agent or in separate dotage units.

Another aspect of the present invention is a potential method of treating one or more diseases associated with HDM2, comprising administering to a mammal in need of such treatment an amount of a first compound, which is a compound of the present invention, or a pharmaceutically acceptable salt or solvate thereof; and an amount of at least bile second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and microRNA) against cancer and neoplastic diseases,
1) anti-metabolites (such as methoxtrexate, 5-fluorouracil, gemcitabine, fludarabine, capecitabine);
2) alkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) topoisomerase II inhibitors, such as etoposide, doxorubicin,
6) topoisomerase I inhibitors, such as irinotecan, topotecan,
7) tubulin interacting agents, such as paclitaxel, docetaxel, Abraxane, epothilones,
8) kinesin spindle protein inhibitors,
9) spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) sex hormone modulating agents,
   a. anti-estrogens, such as tamoxifen, fulvestrant,
   b. selective estrogen receptor Modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 C17 lyase (CYP450c17, also called 17α-hydroxylase/17,20 lysase) inhibitors, such as Abiraterone acetate, VN/124-1, TAK-700
   g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors,
   a. ABL kinase inhibitors, imatinib and nilotinib, dasatinib
   b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
   c. Polo-like kinase inhibitors
   d. Aurora kinase inhibitors
   e. JAK inhibitor
   f. c-MET kinase inhibitors
   g. Cyclin-dependent kinase inhibitors, such as CDK1 and CDK2 inhibitor SCH 727965
   h. PI3K and mTOR inhibitors, such as GDC-0941, BEZ-235, BKM-120 and AZD-8055
   i. Rapamycin and its analogs, such as Temsirolimus, everolimus, and deforolimus
23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone Propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelarnine, Bexxar, Zevalin, Trisenox, Profiler, Thiotepa, Altretamine, Doxil, Ontak, Depocyt, Aranesp, Neupogen, Neulasta, Kepivance.
24) Farnesyl protein transferase inhibitors, such as, SARASAR™ (4-[2-[4-[(11R)-3,10-dibromo-8-chloro-6, 11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) Anti-CTLA-4 antibodies, such as ipilimumab
34) antibodies against CTA1, CEA, CD5, CD19, CD22, CD30, CD44, CD44V6, CD55, CD56, EpCAM, FAP, MHCII, HGF, IL-6, MUC1, PSMA, TALE, TAG-72, TRAILR, VEGFR, IGF-2, FGF,
35) anti-IGF-1R antibodies, such as dalotuzumab (MK-0646) and robatumumab (SCH 717454).

If formulated as a fixed dose such combination products employ the compounds of this invention within the dosage range described herein and the other pharmaceutically active agent or treatment within its dosage range. Compounds of Formula I may also be administered sequentially with known anticancer or cytotoxic agents when a combination formulation is inappropriate. The invention is not limited in the sequence of administration; compounds of Formula I may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formula I, or a pharmaceutically acceptable salt or solvate thereof, and an amount of one or more anti-cancer treatments and anti-cancer agents listed above wherein the amounts of the compounds/treatments result in desired therapeutic effect.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cystostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response Modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cystostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycamptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-anninoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylaminol]-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-ylacetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LEBCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/08169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 67/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxemide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-biS-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598.

Inhibitors of COX-2 can be useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed compounds with PPAR-γ (i.e., PPAR-gamma) agonists and PPAR-δ (i.e., PPAR-delta) agonists can be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (Such as DkF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses angiogenesis-Dependent Tumor Growth and Dissemination in Mice" Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (vaispodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939; 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, CI1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/

031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with potassium salts, magnesium salts, beta-blockers (such as atenolol) and endothelin-a (ETa) antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors: olaparib, MK-4827 and veliparib.

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomybin (Cerubidine®); degarelix (Firmagon®); Denileukin diftitox (Ontak®); dexrazoxane (Zinecard®); dexrazoxane hydrochloride (Totect®); didemnin B, 17-DMAG; docetaxel (Taxotere®); doxorubicin (Adriamycin PFS®); doxorubicin (Adriamycin®, Rubex®); doxorubicin (Adriamycin PFS Injection®); dokorubicin liposomal (Doxil®); dromostanolone propionate (Drorhostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargate (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-

1742), and the Physician's Desk Reference, 57th Edition, 2003 (Published by Thompson PDR, Montvale, N.J. 07645-1742).

The invention disclosed herein is exemplified by the following preparations and examples which should not be construed to limit the scope of the disclosure.

EXAMPLES

The following abbreviations have the following meanings unless defined otherwise:
ACN Acetonitrile
AcOH Acetic acid
DAST (diethylamino)sulfur trifluoride
DCC Dicyclohexylcarbodiimide
DCU Dicyclohexylurea
DCM Dichloromethane
DI Deionized water
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DTT Dithiothreitol
EDCI 1-(3-dimethylamino-propyl)-3-ethylcarbodiimide hydrochloride
EtOAc Ethyl acetate
EtOH Ethanol
HATU N,N,N',N'-Tetramethyl-O-(7-Azabenzotriazol-1-yl)Uronium hexafluorophosphate
Hex hexanes
HOBt 1-Hydroxylbenzotriazole
HPLC High pressure liquid chromatography
LCMS Liquid chromatography mass spectrometry
LDA Lithium diisopropylamide
mCPBA meta-Chloroperoxybenzoic acid
MeOH Methanol
MTT (3-[4,5-dimethyl-thiazol-2-yl]-2,5-diphenyltetrazolium bromide, Thiazolyl blue)
NMR Nuclear magnetic resonance
PFP Pentafluorophenol
PMB p-methoxybenzyl
Pyr Pyridine
Rb Round bottom flask
Rbt Round bottom flask
RT Room temperature
SEMCl 2-(Trimethylsily)ethoxy methyl chloride
TBTU O-(Benzotriazol-1-yl)-N,N,N',N'-tetramethyluronium tetrafluoroborate
TEA Triethylamine
Tr Triphenyl methane
Trt Triphenyl methane
TrCl Triphenyl methane chloride
TFA Trifluoroacetic acid
THF Tetrahydrofuran
TLC Thin layer chromatography
TMS Trimethylsilyl Example 1

Representative Procedures to Prepare Substituted Tetrahydroisoquinolines

The following common intermediates were prepared according to previous publications (US 2008/0004287 A1; WO 2011/046771 A1).

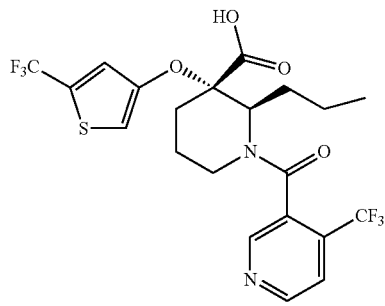

1

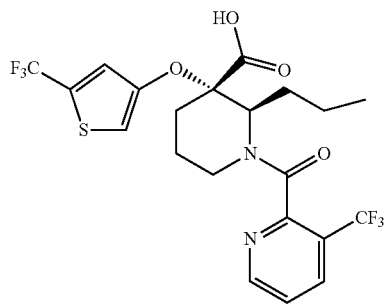

2

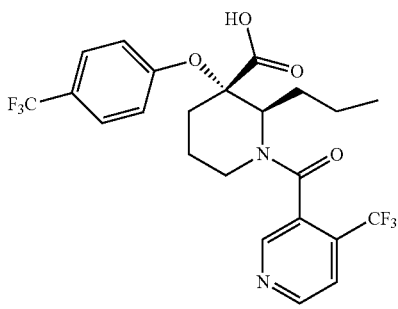

3

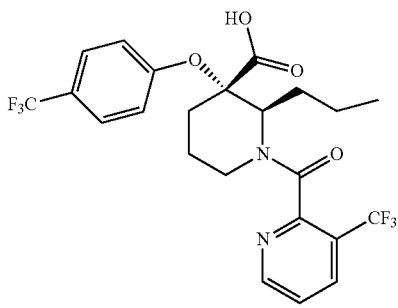

4

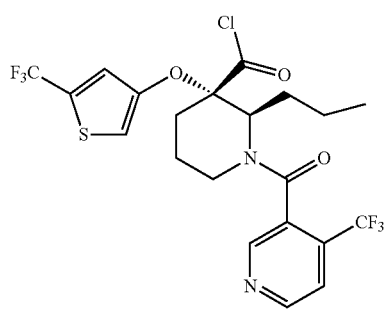

5

-continued

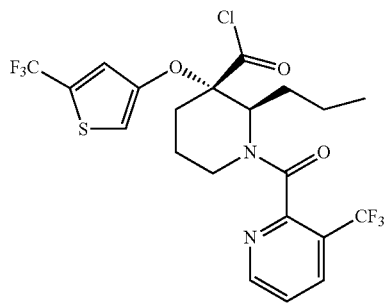
6

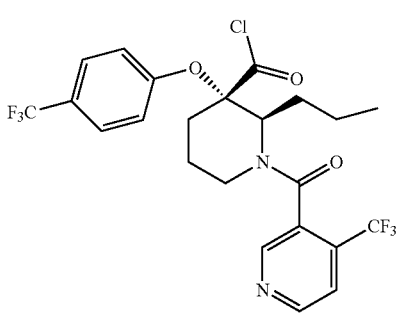
7

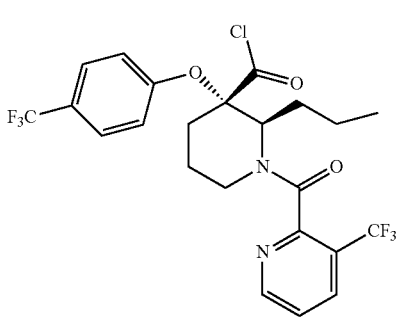
8

Synthesis of (R)-6-chloro-2-(ethoxycarbonyl)-1,2,3,4-tetrahydroisoquinoline-3-carboxylic acid (10)

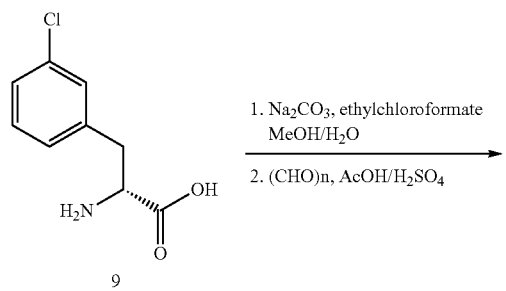

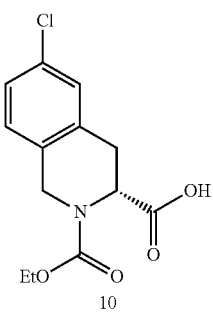

Na$_2$CO$_3$ (2.12 g, 20.04 mmol) was added to a suspension of 3-chloro-D-phenylalanine 9 (2.6 g, 10.02 mmol) in MeOH/H$_2$O (8.3 mL/8.3 mL) at room temperature. Ethyl chloroformate (1.44 mL, 15.03 mmol) was added drop wise over 20 min via syringe pump and the reaction was stirred overnight. The reaction mixture was washed with Et$_2$O (1×15 mL) and the aqueous layer was acidified to pH ~5 with 2 M HCl (aq). The aqueous layer was extracted with EtOAc (2×30 mL). The combined organics were washed with brine, dried over MgSO$_4$, filtered and concentrated to obtain the ethyl carbamate.

The crude ethyl carbamate (1.62 g, 6.35 mmol) was dissolved in AcOH/conc. H$_2$SO$_4$ (3:1, 6.0 mL/2.0 mL). Paraformaldehyde (200 mg, 6.67 mmol) was added and the reaction was stirred at room temperature overnight. EtOAc (15 mL) and H$_2$O (15 mL) were added to the reaction mixture. The layers were separated and the aqueous layer was extracted with EtOAc (3×20 mL). The combined organics were dried over MgSO$_4$, filtered and concentrated to obtain (R)-6-chloro-2-(ethoxycarbonyl)-1,2,3,4-tetrahydroisoquinoline-3-carboxylic acid 10 (2.3 g, 8.13 mmol, 81% overall yield).

Synthesis of (R)-2-tert-butyl 3-methyl 6-chloro-3,4-dihydroisoquinoline-2,3(1H)-dicarboxylate (11)

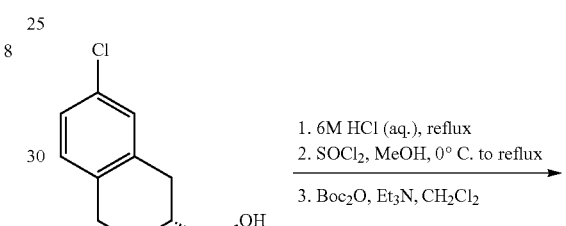

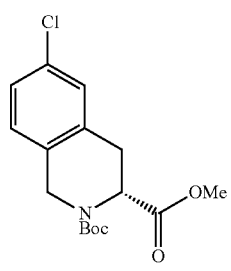

6 M aq. HCl (28 mL) was added to tetrahydroisoquinoline carbamate 10 (2.3 g, 8.13 mmol) and was refluxed overnight. The reaction mixture was cooled to room temperature as precipitate had formed. The solution was further cooled to 0° C. for 1 h. The precipitate was filtered, washed with Et$_2$O (3×) and was dried Under vacuum overnight to obtain the free tetrahydroisoquinoline.

The tetrahydroisoquinoline carboxylic acid (715 mg, 3.39 mmol) was suspended in MeOH (4.7 mL) and was cooled to 0° C. SOCl$_2$ (371 µL, 6.08 mmol) was added dropwise. The reaction was then refluxed under N$_2$ for 1.5 h. The mixture was cooled to room temperature and was concentrated to obtain the methyl ester.

The free tetrahydroisoquinoline (652 mg, 2.50 mmol) was dissolved in CH$_2$Cl$_2$ (16 mL). A solution of Boc$_2$O (572 mg, 2.62 mmol) and Et$_3$N (697 µL, 5.0 mmol) in CH$_2$Cl$_2$ (4 mL) was added to the reaction mixture and was stirred overnight at room temperature. The reaction was diluted with H$_2$O and Synthesis of (R)-6-chloro-2-((2R,3S)-2-propyl-1-(3-(trifluoromethyl)picolinoyl)-3-(5-(trifluoromethyl)thiophen-3-yloxy)piperidine-3-carbonyl)-1,2,3,4-tetrahydroisoquinoline-3-carboxylic acid (A129)

Synthesis of (R,E)-tert-butyl 6-chloro-3-(3-ethoxy-3-oxoprop-1-enyl)-3,4-dihydroisoquinoline-2(1H)-carboxylate (12)

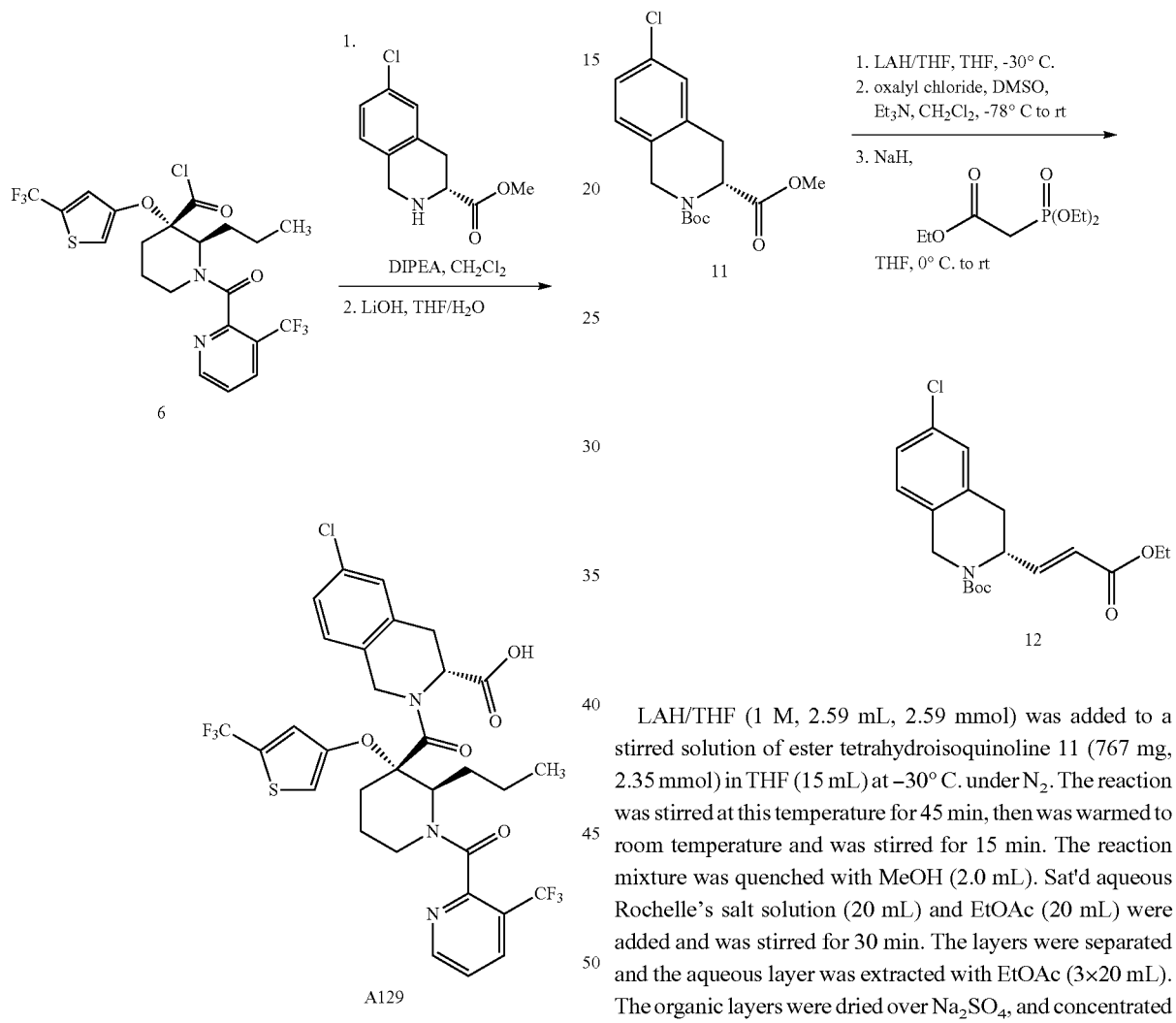

The acid chloride 6 (40 mg, 75.6 μmol) was dissolved in $CH_2Cl_2$ (0.8 mL). A solution of tetrahydroisoquinoline amine (30 mg, 11.3 μmol, obtained from the treatment of purified 11 with 4N HCl in dioxane) and DIPEA (40 μL, 22.7 μmol) in $CH_2Cl_2$ (0.5 mL) was added to the reaction mixture. The reaction was stirred at room temperature for 3 h. The reaction was concentrated and was purified by silica gel chromatography (EtOAc/hexane, gradient, 30% to 50%).

LiOH (9 mg, 37.8 μmol) was added to a stirred solution of the ester (54 mg, 75.6 μmol) in $EtOH/H_2O$ (0.8 mL/2 drops). The reaction mixture was stirred at 50° C. for 1 h. The reaction was concentrated and was acidified to pH ~4 with 1 M HCl (aq). The mixture was extracted with EtOAc (3×15 mL). The organic layers were dried over $Na_2SO_4$ and concentrated. The crude product was purified by reverse phase preparative HPLC to yield A129.

LAH/THF (1 M, 2.59 mL, 2.59 mmol) was added to a stirred solution of ester tetrahydroisoquinoline 11 (767 mg, 2.35 mmol) in THF (15 mL) at −30° C. under $N_2$. The reaction was stirred at this temperature for 45 min, then was warmed to room temperature and was stirred for 15 min. The reaction mixture was quenched with MeOH (2.0 mL). Sat'd aqueous Rochelle's salt solution (20 mL) and EtOAc (20 mL) were added and was stirred for 30 min. The layers were separated and the aqueous layer was extracted with EtOAc (3×20 mL). The organic layers were dried over $Na_2SO_4$, and concentrated to obtain the corresponding alcohol.

Oxalyl chloride (388 μL, 4.08 mmol) was added to a stirred solution of DMSO (580 μL, 8.16 mmol) in $CH_2Cl_2$ (18 mL) at −78° C. under $N_2$ and was stirred for 15 min. A solution of the alcohol (608 mg, 2.04 mmol) in $CH_2Cl_2$ (2.0 mL) was added to the reaction mixture and was stirred at −78° C. for 1 h. $Et_3N$ (1.42 mi., 10.2 mmol) was added and the solution was warmed to room temperature and Was stirred for 1 h. The reaction mixture was quenched with sat'd aqueous $NaHCO_3$. The layers were separated and the aqueous layers was extracted with $CH_2Cl_2$ (2×x20 mL). The organic layers were washed with brine, dried over $MgSO_4$, filtered and concentrated to obtain the corresponding aldehyde.

NaH (60% in oil, 92 mg, 2.31 mmol) was washed with hexanes (2×3 mL). THF (15 mL) was added under N₂. The solution was cooled to 0° C. and triethylphosphonoacetate (499 μL, 2.52 mmol) was added drop wise and was stirred for 20 min. A solution of the aldehyde (620 mg, 2.10 mmol) in THF (5 mL) was added to the reaction mixture at 0° C. The reaction was warmed to room temperature and was stirred overnight. The reaction mixture was quenched with sat'd aqueous NH₄Cl (5 mL). The layers were separated and the aqueous layer was extracted with EtOAc (2×20 mL). The organic layers were washed with brine (1×30 mL), dried over MgSO₄, filtered and concentrated to obtain the desired product, 12. The crude product 12 was purified by silica gel chromatography (EtOAc/hexanes, gradient, 10% to 30%).

Synthesis of (S)-ethyl 3-(6-chloro-1,2,3,4-tetrahydroisoquinolin-3-yl)propanoate (13)

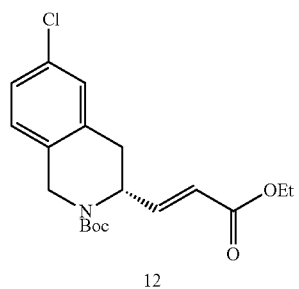

ZnBr₂ (13 mg, 58.6 μmol) was added to a stirred solution of the 12 (107 mg, 0.293 mmol) in MeOH. The solution was degassed with N₂ for a few minutes. Pd(OH)₂/C (20%, 20 mg) was added and then H₂ was bubbled into the mixture for a few minutes. The reaction was stirred under a H₂ balloon overnight at room temperature. The solution was filtered through Celite, washed with EtOAc and concentrated to obtain the hydrogenated product and dichlorinated product (<10%). The crude product was purified by silica gel chromatography (EtOAc/hexanes, gradient, 10% to 20%).

HCl/dioxane (4 M, 511 μL, 2.04 mmol) was added to neat Boc-tetrahydroisoquinoline (75 mg, 0.204 mmol) at room temperature and was stirred for 2 h. The reaction mixture was concentrated to obtain (S)-ethyl 3-(6-chloro-1,2,3,4-tetrahydroisoquinolin-3-yl)propanoate 13.

Synthesis of 3-((S)-6-chloro-24(2R,3S)-2-propyl-1-(3-(trifluoromethyl)picolinoyl)-3-(6-(trifluoromethyl)thiophen-3-yloxy)piperidine-3-carbonyl)-1,2,3,4-tetrahydroisoquinolin-3-yl)propanoic acid, A130

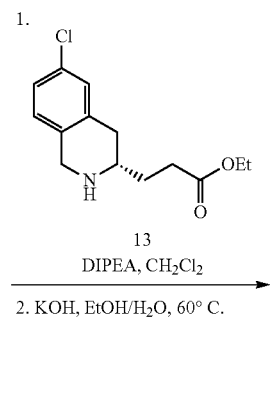

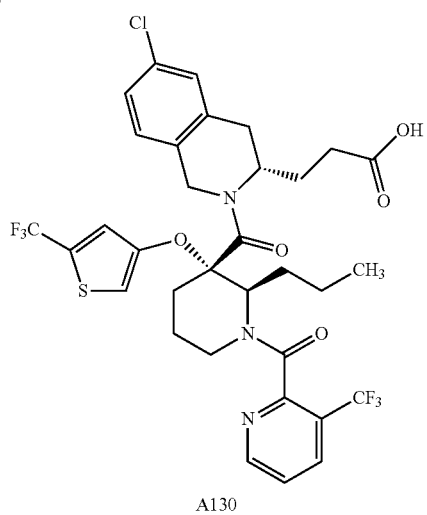

The acid chloride 6 (87 mg, 0.165 mmol) was dissolved in CH₂Cl₂ (1.15 mL). A solution of (S)-ethyl 3-(6-chloro-1,2,3,4-tetrahydroisoquinolin-3-yl)propanoate 13 (60 mg, 0.198 mmol) and DIPEA (88 μL, 0.495 mmol) in CH₂Cl₂ (0.5 mL) was added to the reaction mixture. The reaction was stirred at room temperature for 2.5 h. The reaction was concentrated and was purified by silica gel chromatography (EtOAc/hexanes, gradient, 30% to 50%).

KOH (18 mg, 0.32 mmol) was added to a stirred solution of the ester (49 mg, 64.5 μmol) in EtOH/H₂O (0.7 mL/2 drops). The reaction mixture was stirred at 60° C. for 1 h. The reaction was concentrated and was acidified to pH ~4 with 1 M HCl (aq). The mixture was extracted with EtOAc (3×15 mL). The organic layers were dried over Na₂SO₄ and concentrated. The crude product was purified by reverse phase preparative HPLC to yield 3-((S)-6-chloro-24(2R,3S)-2-propyl-1-(3-(trifluoromethyl)picolinoyl)-3-(5-(trifluoromethyl)thiophen-3-yloxy)piperidine-3-carbonyl)-1,2,3,4-tetrahydroisoquinolin-3-yl)propanoic acid, A130. LC/MS RT (10 min method)=4.315 min.

Two Representative Routes to Modify the Substituted Tetrahydroisoquinolines: preparation of A45

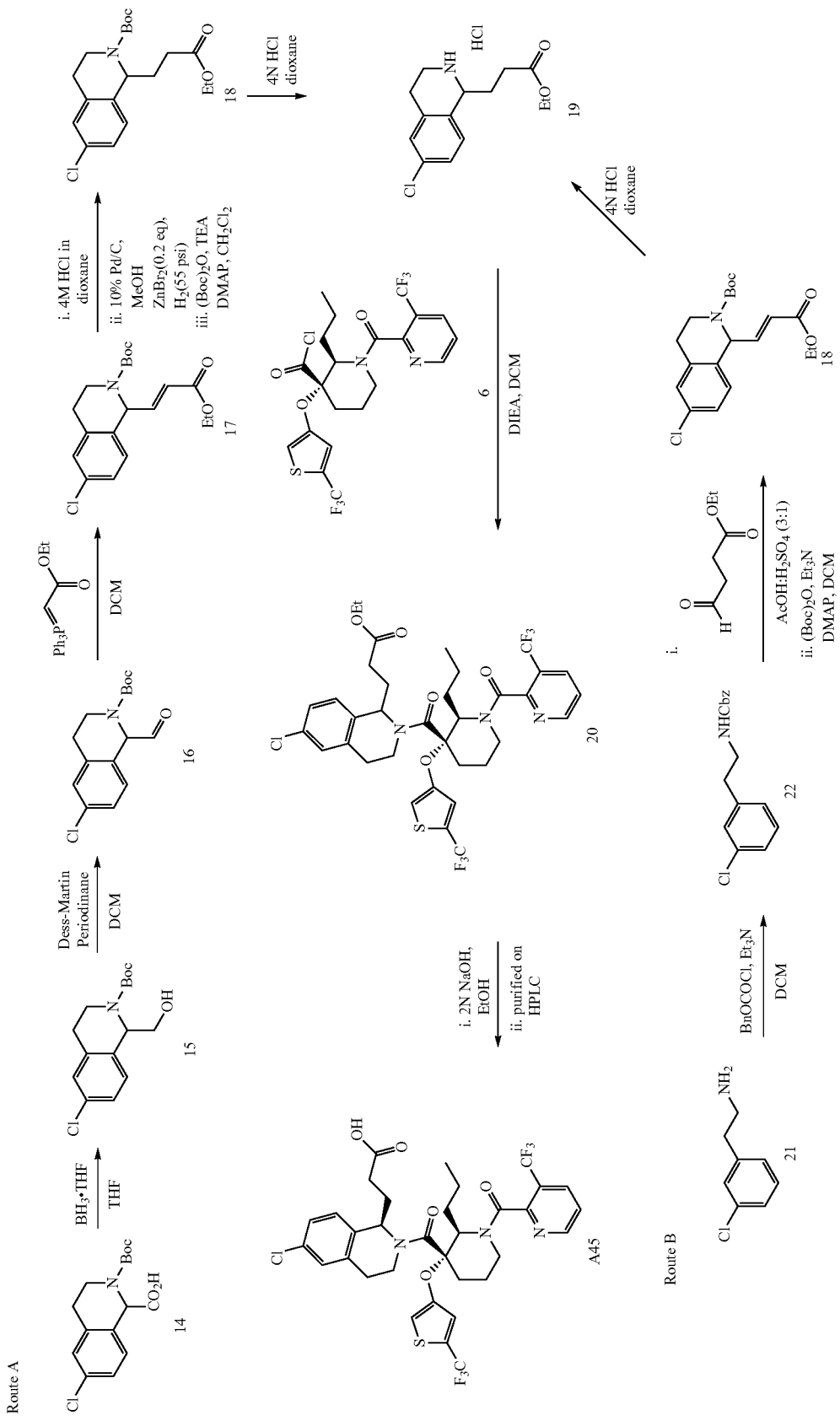

Route A

To a solution of 14 (6.4 mmol, 2.0 g) in tetrahydrofuran at 0° C. was added borane-THF complex (1.0M in THF, 8 mmol, 8.0 ml). The reaction mixture was stirred at rt for 4 h. The reaction was quenched with water, extracted with EtOAc. The combined organic layer was washed with brine, dried (MgSO4), and concentrated. The crude product 15 was obtained as colorless oil (~2.0 g) and used in the next step without further purification.

To a stirring solution of 15 (~2.0 g) in DCM (30 ml) at room temperature was added Dess-Martin Periodinane and the reaction mixture was stirred at rt for 1 h. The solvent was removed in vacuo. The reaction was quenched with water, extracted with EtOAc. The combined organic layer was washed with brine, dried (MgSO4), and concentrated. The crude product 16 was obtained as colorless oil (1.8 g) and used in the next step without further purification.

To a stirring solution of 16 (1.8 g) in DCM (30 ml) at room temperature was added (carbethoxymethylene)triphenylphosphorane and the reaction mixture was stirred at rt for 3 days. The solvent was removed in vacuo. The crude product was purified on Biotage (EtOAc in hexane: 10~25%) to give 17 as yellowish oil (1.0 g). 17 (50 mg, 0.14 mmol) was treated with 4M HCl for 1 h. Then the solvent was removed in vacuo. To the residue in MeOH was added catalytical amount of 10% Pd/C followed by Zinc Bromide (0.2 eq) and the mixture was subjected to hydrogenation (55 psi) on Parr Shaker. After stirring at room temperature overnight, the mixture was filtered through Celite. The filtrate was concentrated in vacuo, to give the residue that was protected With Boc by following standard conditions. After work-up, the crude product Bog-protected amine was purified on Biotage (EtOAc in hexane: 5~10%) to give 18 as colorless oil (30 mg).

To a solution of 18 in acetonitrile at room temperature was added 4.0 M hydrochloride in 1,4-dioxane. After 1 h, the solvent was removed by lyophilization, to give 19 as white solid.

To a stirring mixture of acid intermediate 6 and 19 in DCM at room temperature was added followed by DIEA. The reaction was stirred at room temperature overnight. The solvent was removed in vacuo. The crude product was purified on Biotage (EtOAc in hexane: 25~50%), to give 20 as white solid.

To 20 in ethanol was added 2.0 M NaOH aqueous solution and the mixture was stirred at 70° C. for 1 h. Then the solvent was removed in vacuo. The residue was redissolved in water, acidified with 6N HCl to pH ~4, then extracted with EtOAc (2×30 ml), dried (MgSO4), concentrated, purified on Gilson, to give two isomers with both as white solids. The 1$^{st}$ one obtained was A45.

Route B

To a solution of 2-(3-chlorophenyl)-ethylamine 21 (24 g, 0.15 mol) in DCM (500 ml) and triethylamine (23 ml, 0.165 mmol) at 0° C. was added dropwise benzyl chloroformate and the resulting solution was stirred at 0° C. for 30 min and then at rt overnight. The reaction mixture was washed with saturated NaHCO$_3$, brine, and then concentrated. The crude product was purified on Biotage (EtOAc in hexane: 10~25%) to give 22 (35 g) as light yellow oil.

To a stirring mixture of 22 (5.9 g, 20 mmol) and methyl-4-oxobutyrate (3.4 ml, 30 mmol) at 0° C. was added the premixed solvent H$_2$SO$_4$:AcOH (1:3, 40 ml) and the mixture was stirred at room temperature overnight. The reaction mixture was then poured into ice, extracted with DCM (4×75 ml). The organic phase was concentrated. The crude product 18 was obtained as reddish oil (~6.0 g), which was subjected the Boc-protection by following standard condition. After work-up and purification on Biotage (EtOAc in hexane: 5-10%) to give the pure product 19 as pinky oil (0.8 g).

Synthesis of A73 and A74

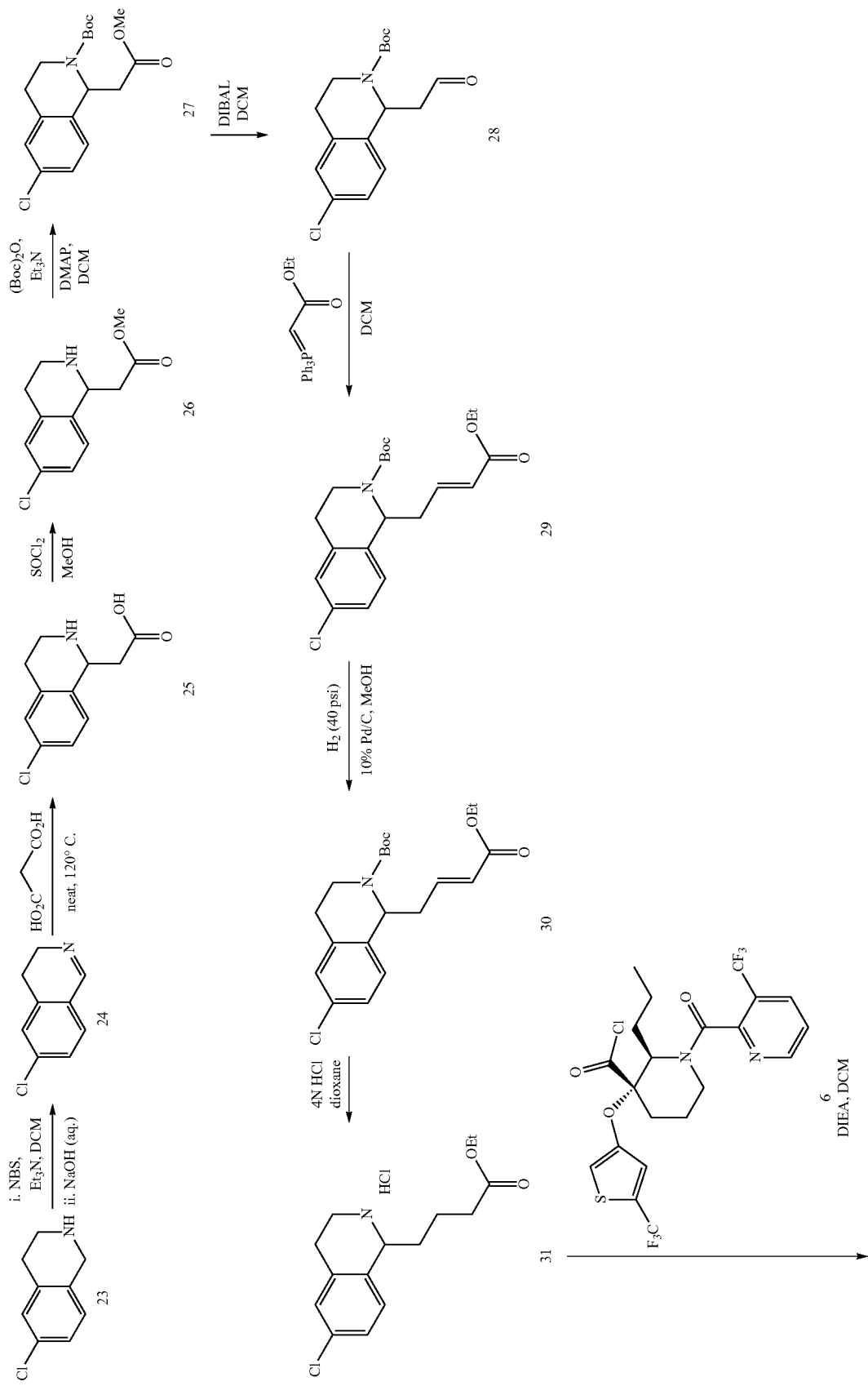

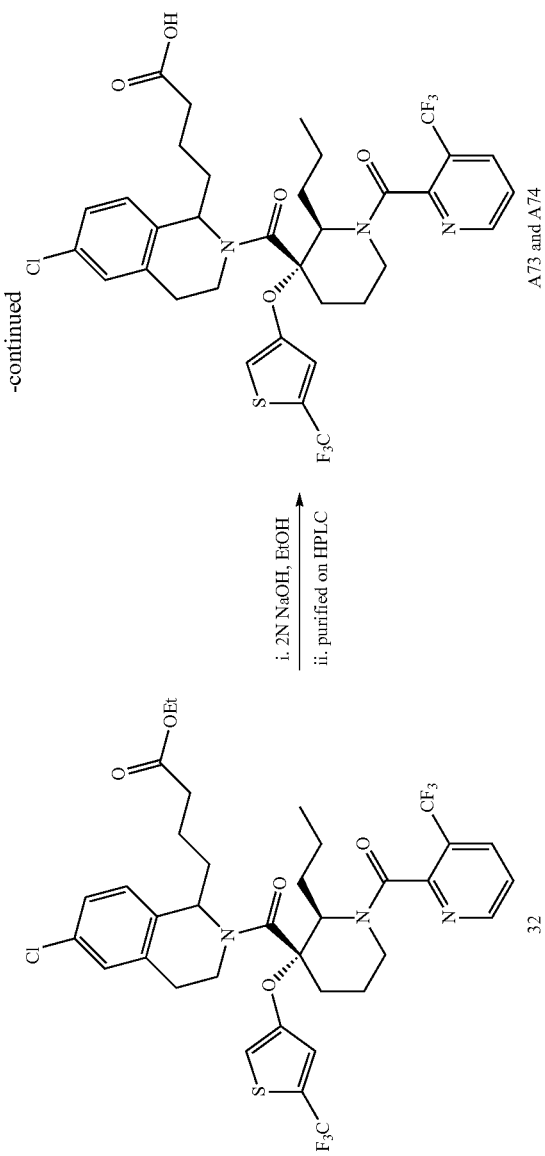

To a stirring solution of 23 (1 mmol, 200 mg) in dichloromethane and triethylamine (2 mmol, 0.3 ml) at room temperature was added N-bromosuccinimide (1.1 mmol, 200 mg). The reaction mixture was stirred at room temperature for 30 min. Then 2.0 M NaOH aqueous solution was added and the reaction mixture was stirred at rt for another 1 h. The reaction mixture as extracted with DCM. The combined organic layer was over MgSO₄. The solvent was removed in vacuo. The crude product 24 was used in the next step without further purification.

The crude material 24 (1 mmol) and Malonic acid were mixed well at room temperature. The mixture was immersed in an oil bath that was preheated to 120° C. and stirred for 1 h. After cooling down, the residue 25 was used in the next step without further purification.

Thionyl chloride (1.1 mmol, 80 ul) was added dropwise with stirring to methanol at −10° C. Stirring was continued for 30 min at −10° C. A solution of 25 in MeOH was then added and the reaction mixture was stirred et rt overnight. The solvent was removed in vacuo. The residue was dissolved in DCM and added with 3 drops of triethylamine, then diluted with EtOAc, washed with saturated NaHCO₃ twice, then brine and then dried over MgSO₄. The solvent was removed in vacuo. The crude product 26 was obtained as brownish oil (~0.2 g).

To a stirring solution of 26 in dichloromethane and triethylamine at room temperature was added di-t-butyl dicarbonate followed by DMAP. The reaction mixture was stirred at room temperature overnight and then diluted with EtOAc, washed with water, brine, then dried (MgSO₄). The solvent was removed in vacuo. The crude product 27 was obtained as brownish oil, which was used in the next step without further purification.

To a solution of 27 in dichloromethane was added diisobutylaluminum and the reaction mixture was stirred at −78° C. for 1 h. Then Rochelle salt solution was added, and the mixture was stirred vigorously for 30 min and then extracted with EtOAc. The organic phase was separated and the aqueous phase was extracted with EtOAc. The combined organic phase was dried over MgSO₄, concentrated. The crude product 28 was used in the next step without further purification.

To a stirring solution of 28 in DCM at room temperature was added (carbothoxymethylene)triphenylphosphorane and the reaction mixture was stirred at reflux overnight. The solvent was removed in vacuo. The crude product was purified on Biotage (EtOAc in hexane: 10~25%) to give 29 as colorless oil. To a stirring solution of 29 in EtOAc was added catalytical amount of 10% palladium on carbon and the reaction mixture was purged with Hydrogen balloon. After stirring at room temperature overnight, the mixture was filtered through celite and concentrated in vacuo, to give 30 as colorless oil, which was used in the next step without further purification. To a solution of 30 in acetonitrile at room temperature was added 4.0 M hydrochloride in 1,4-dioxane. After 1 h, the solvent was removed by lyophilization, to give 31 as yellowish oil.

To a stirring mixture of acid intermediate 6 (0.1 mmol, 50 mg) and 31 (0.2 mmol, 70 mg) in DCM at room temperature was added HATU (0.15 mmol, 57 mg) followed by DIEA (0.1 ml). The reaction was stirred at room temperature overnight. The solvent was removed in vacuo. The crude product was purified on Biotage (EtOAc in hexane: 25~50%), to give 32 as white solid.

To 32 in ethanol was added 2.0 M NaOH aqueous solution and the mixture was stirred at 70° C. for 1 h. Then the solvent was removed in vacuo. The residue was redissolved in water and acidified with 6N HCl to pH~4, then extracted with EtOAc (2×30 ml), dried (MgSO₄), concentrated, purified on HPLC, treated with 4.0 M HCl in dioxane (2-3 drops), lyophilized, give the two separated isomers A73 and A74, both of which are white solid.

Using analogous methods as described above, the following compounds in Table 1 can be synthesized.

| Name | Structure | IUPAC Name | Exact Mass [M + H]+ | FP IC50 (um) |
|------|-----------|------------|---------------------|--------------|
| A1 | 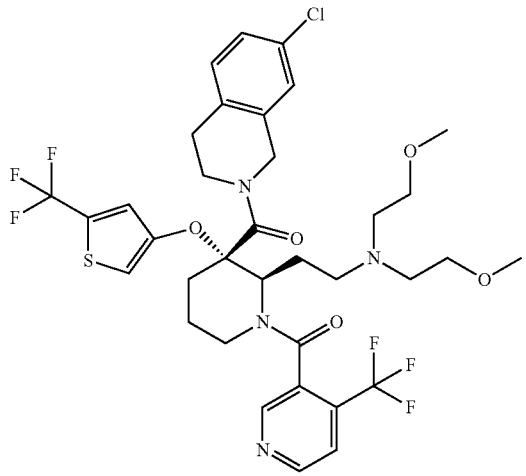 [SMILES: COCCN(CCOC)CC[C@H]1N(C(=O)c2cnccc2C(F)(F)F)CCC[C@@]1(Oc1csc(C(F)(F)F)c1)C(=O)N1CCc2ccc(Cl)cc2C1] | 2-[(2R,3S)-3-[(7-chloro-3,4-dihydroisoquinblin-2(1H)-yl)carbonyl]-1-{[4-(trifluoromethyl)byridin-3-yl]carbonyl}-3-{[5-(trifluoromethyl)thiophen-3-yl]oxy}piperidin-2-yl]-N,N-bis(2-methoxyethyl)ethanamine | Calc'd 777.2, found 776.8 | 472 |

-continued

| Name | Structure | IUPAC Name | Exact Mass [M + H]+ | FP IC50 (um) |
|---|---|---|---|---|
| A2 | 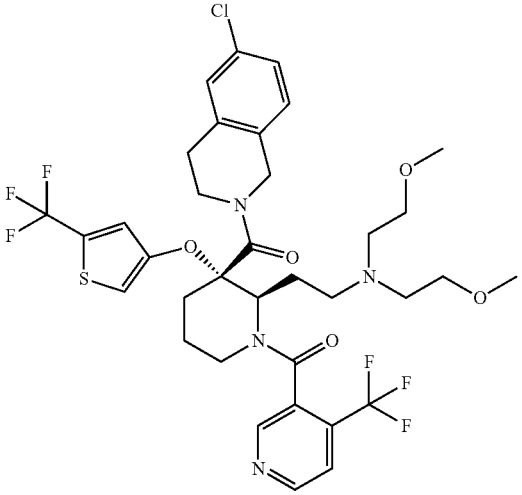 [SMILES: COCCN(CCOC)CC[C@H]1N(C(=O)c2cnccc2C(F)(F)F)CCC[C@@]1(Oc1csc(C(F)(F)F)c1)C(=O)N1CCc2cc(Cl)ccc2C1] | 2-[(2R,3S)-3-[(6-chloro-3,4-dihydroisoquinblin-2(1H)-yl)carbonyl]-1-{[4-(trifluoromethyl)byridin-3-yl]carbonyl}-3-{[5-(trifluoromethyl)thiophen-3-yl]oxy}piperidin-2-yl]-N,N-bis(2-methoxyethyl)ethanamine | Calc'd 777.2, found 776.8 | A |
| A3 | 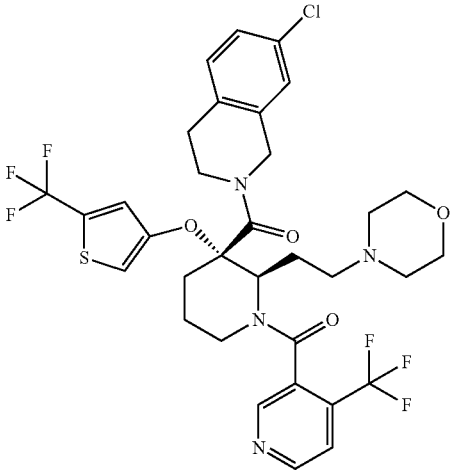 [SMILES: O=C(c1cnccc1C(F)(F)F)N1CCC[C@@](Oc2csc(C(F)(F)F)c2)(C(=O)N2CCc3ccc(Cl)cc3C2)[C@H]1CCN1CCOCC1] | 7-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline | Calc'd 731.2, found 731.1 | B |
| A4 | 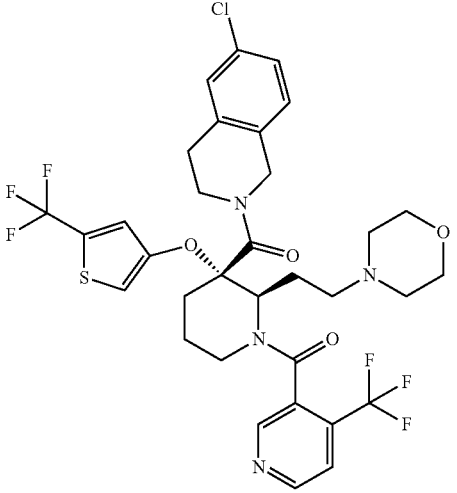 [SMILES: O=C(c1cnccc1C(F)(F)F)N1CCC[C@@](Oc2csc(C(F)(F)F)c2)(C(=O)N2CCc3cc(Cl)ccc3C2)[C@H]1CCN1CCOCC1] | 6-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline | Calc'd 731.2, found 731.1 | A |

| Name | Structure | IUPAC Name | Exact Mass [M + H]+ | FP IC50 (um) |
|---|---|---|---|---|
| A5 | 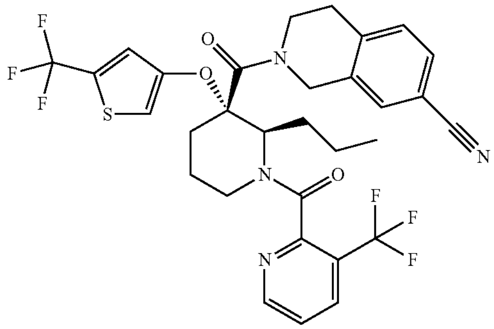 [SMILES: CCC[C@H]1N(C(=O)c2ncccc2C(F)(F)F)CCC[C@@]1(Oc1csc(C(F)(F)F)c1)C(=O)N1CCc2ccc(C#N)cc2C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-7-carbonitrile | Calc'd 651.2, found 651.1 | B |
| A6 | 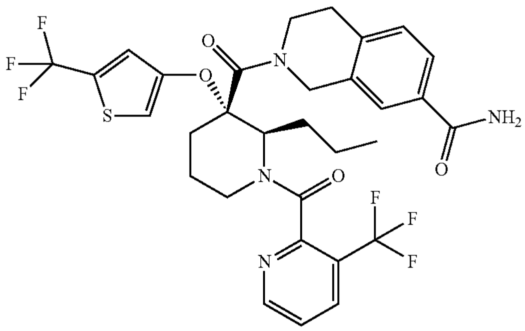 [SMILES: CCC[C@H]1N(C(=O)c2ncccc2C(F)(F)F)CCC[C@@]1(Oc1csc(C(F)(F)F)c1)C(=O)N1CCc2ccc(C(N)=O)cc2C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-7-carboxamide | Calc'd 669.2, found 669.1 | B |
| A7 | 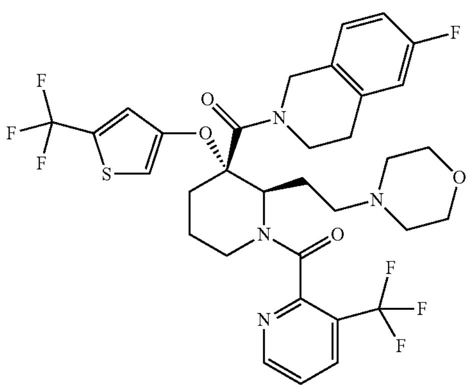 [SMILES: O=C(c1ncccc1C(F)(F)F)N1CCC[C@@](Oc2csc(C(F)(F)F)c2)(C(=O)N2CCc3cc(F)ccc3C2)[C@H]1CCN1CCOCC1] | 6-fluoro-2-{[(2R,3S)-2-(2-morpholin-4-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 715.2, found 715 | A |
| A8 | 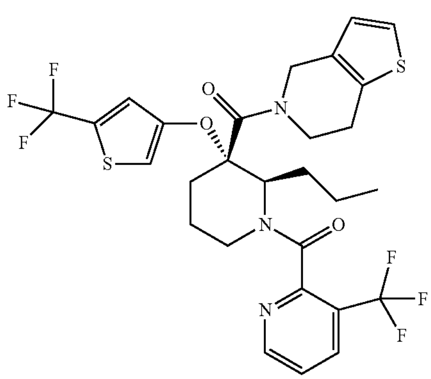 [SMILES: CCC[C@H]1N(C(=O)c2ncccc2C(F)(F)F)CCC[C@@]1(Oc1csc(C(F)(F)F)c1)C(=O)N1CCc2sccc2C1] | 5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine | Calc'd 632.1, found 632 | B |

-continued

| Name | Structure | IUPAC Name | Exact Mass [M + H]+ | FP IC50 (um) |
|---|---|---|---|---|
| A9 | 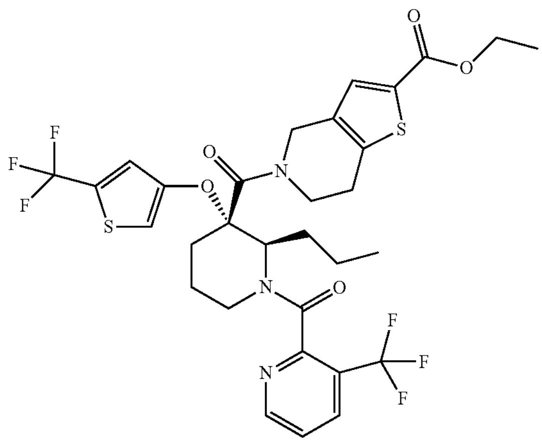 [SMILES: CCC[C@H]1N(C(=O)c2ncccc2C(F)(F)F)CCC[C@@]1(Oc1csc(C(F)(F)F)c1)C(=O)N1CCc2sc(C(=O)OCC)cc2C1] | ethyl 5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylate | Calc'd 704.2, found 704.2 | B |
| A10 | 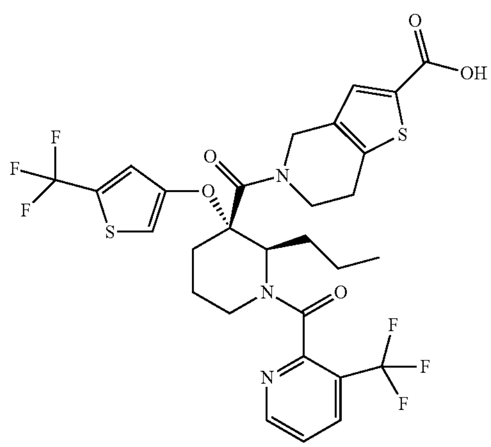 [SMILES: CCC[C@H]1N(C(=O)c2ncccc2C(F)(F)F)CCC[C@@]1(Oc1csc(C(F)(F)F)c1)C(=O)N1CCc2sc(C(=O)O)cc2C1] | 5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylic acid | Calc'd 676.1, found 676 | B |
| A11 | 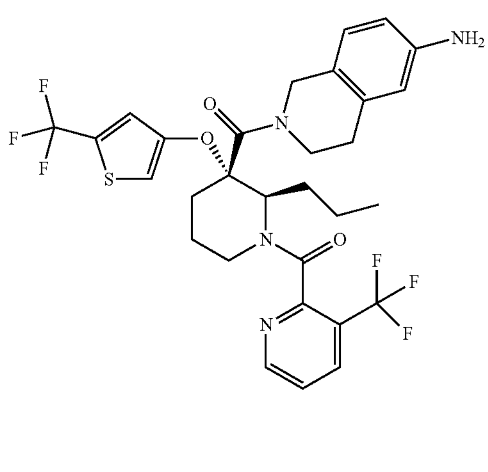 [SMILES: CCC[C@H]1N(C(=O)c2ncccc2C(F)(F)F)CCC[C@@]1(Oc1csc(C(F)(F)F)c1)C(=O)N1CCc2cc(N)ccc2C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine | Calc'd 641.2, found 641 | B |

-continued

| Name | Structure | IUPAC Name | Exact Mass [M + H]+ | FP IC50 (um) |
|---|---|---|---|---|
| A12 | 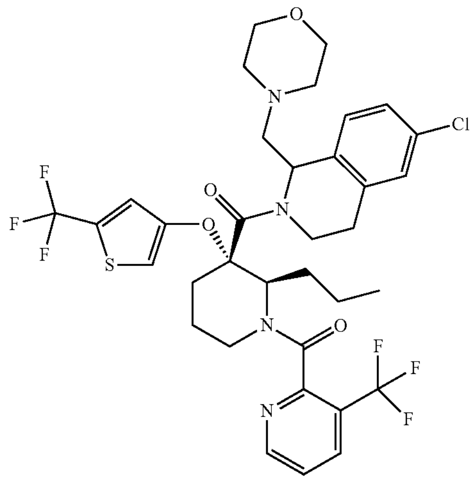 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CN1CCOCC1] | 6-chloro-1-(morpholin-4-ylmethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 759.2, found 759 | A |
| A13 | 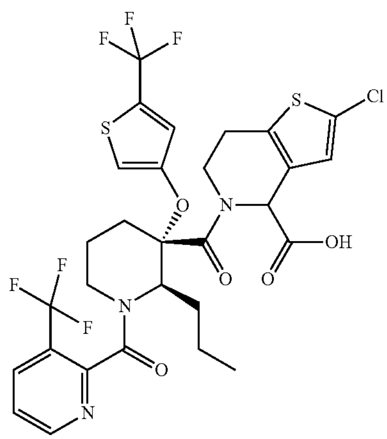 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1C(=O)O] | 2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid | Calc'd 710.1, found 709.9 | A |
| A14 | 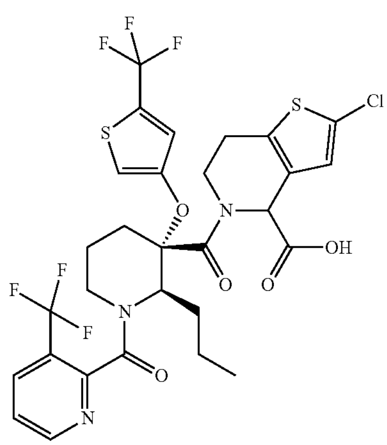 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1C(=O)O] | 2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid | Calc'd 710.1, found 709.9 | A |

| Name | Structure | IUPAC Name | Exact Mass [M + H]+ | FP IC50 (um) |
|---|---|---|---|---|
| A15 | 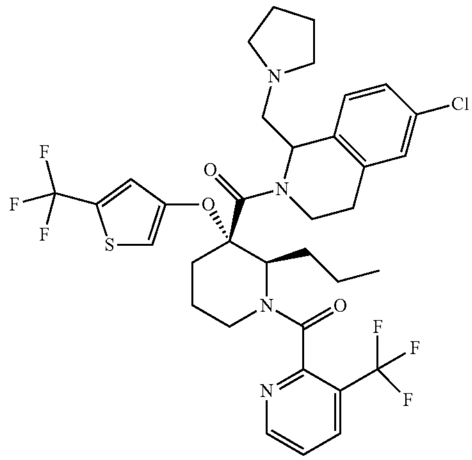 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CN1CCCC1] | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1-(pyrrolidin-1-ylmethyl)-1,2,3,4-tetrahydroisoquinoline | Calc'd 743.2, found 743 | B |
| A16 | 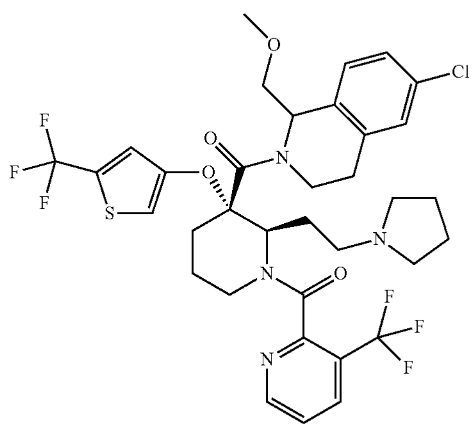 [SMILES: COCC1c2ccc(Cl)cc2CCN1C(=O)[C@]1(Oc2csc(C(F)(F)F)c2)CCCN(C(=O)c2ncccc2C(F)(F)F)[C@@H]1CCN1CCCC1] | 6-chloro-1-(methoxymethyl)-2-{[(2R,3S)-2-(2-pyrrolidin-1-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 759.2, found 759 | A |
| A17 | 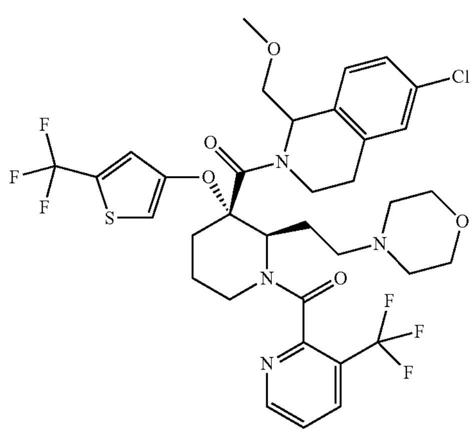 [SMILES: COCC1c2ccc(Cl)cc2CCN1C(=O)[C@]1(Oc2csc(C(F)(F)F)c2)CCCN(C(=O)c2ncccc2C(F)(F)F)[C@@H]1CCN1CCOCC1] | 6-chloro-1-(methoxymethyl)-2-{[(2R,3S)-2-(2-morpholin-4-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 775.2, found 774.8 | A |

-continued

| Name | Structure | IUPAC Name | Exact Mass [M + H]+ | FP IC50 (um) |
|---|---|---|---|---|
| A18 | 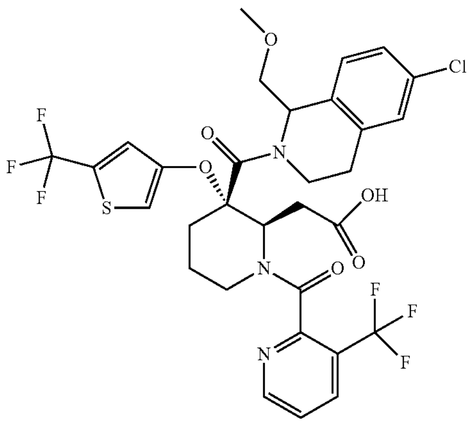 [SMILES: COCC1c2ccc(Cl)cc2CCN1C(=O)[C@]1(Oc2csc(C(F)(F)F)c2)CCCN(C(=O)c2ncccc2C(F)(F)F)[C@@H]1CC(=O)O] | [(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]acetic acid | Calc'd 720.1, found 720.1 | A |
| A19 | 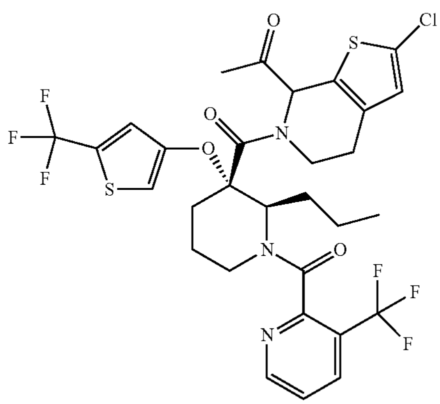 [SMILES: CCC[C@H]1N(C(=O)c2ncccc2C(F)(F)F)CCC[C@@]1(Oc1csc(C(F)(F)F)c1)C(=O)N1CCc2cc(Cl)sc2C1C(C)=O] | 2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-7-carboxylic acid | Calc'd 710.1, found 709.7 | A |
| A20 | 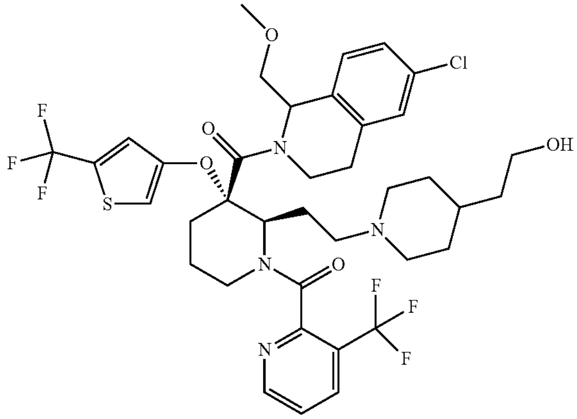 [SMILES: COCC1c2ccc(Cl)cc2CCN1C(=O)[C@]1(Oc2csc(C(F)(F)F)c2)CCCN(C(=O)c2ncccc2C(F)(F)F)[C@@H]1CCN1CCC(CCO)CC1] | 2-(1-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}piperidin-4-yl)ethanol | Calc'd 817.3, found 817 | A |

-continued

| Name | Structure | IUPAC Name | Exact Mass [M + H]+ | FP IC50 (um) |
|---|---|---|---|---|
| A21 | 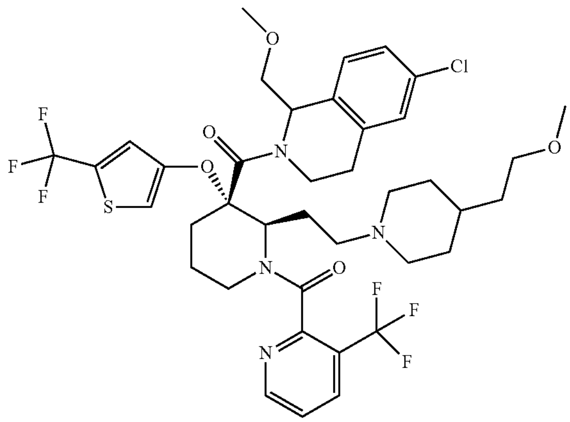 [SMILES: COCCC1CCN(CC[C@H]2N(C(=O)c3ncccc3C(F)(F)F)CCC[C@@]2(Oc2csc(C(F)(F)F)c2)C(=O)N2CCc3cc(Cl)ccc3C2COC)CC1] | 6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1-(methoxymethyl)-1,2,3,4-tetrahydroisoquinoline | Calc'd 832.3, found 832 | A |
| A22 | 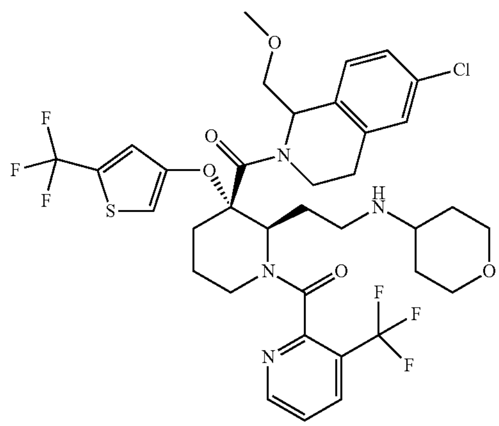 [SMILES: COCC1c2ccc(Cl)cc2CCN1C(=O)[C@]1(Oc2csc(C(F)(F)F)c2)CCCN(C(=O)c2ncccc2C(F)(F)F)[C@@H]1CCNC1CCOCC1] | N-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine | Calc'd 789.2, found 789 | A |
| A23 | 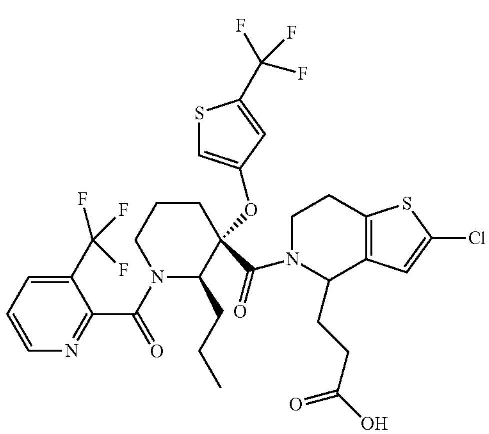 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCC(=O)O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)propanoic acid | Calc'd 738.1, found 739 | A |

-continued

| Name | Structure | IUPAC Name | Exact Mass [M + H]+ | FP IC50 (um) |
|---|---|---|---|---|
| A24 | 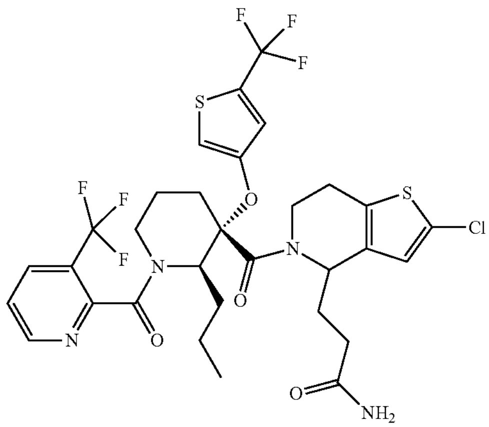 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCC(N)=O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl]propanamide | Calc'd 737.1, found 737 | B |
| A25 | 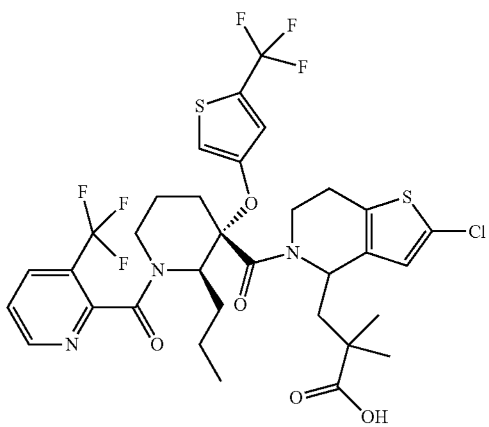 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CC(C)(C)C(=O)O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid | Calc'd 766.2, found 766.1 | A |
| A26 | 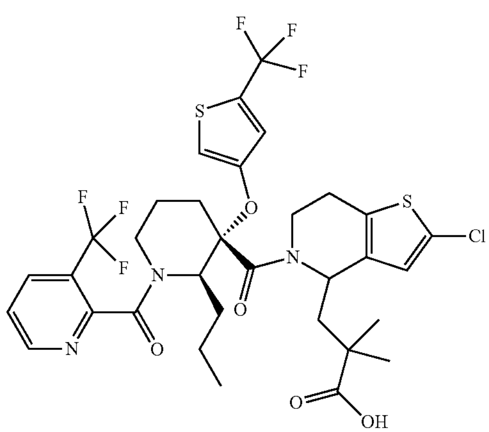 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CC(C)(C)C(=O)O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid | Calc'd 766.2, found 766.1 | A |

| Name | Structure | IUPAC Name | Exact Mass [M + H]+ | FP IC50 (um) |
|------|-----------|------------|---------------------|--------------|
| A27 | 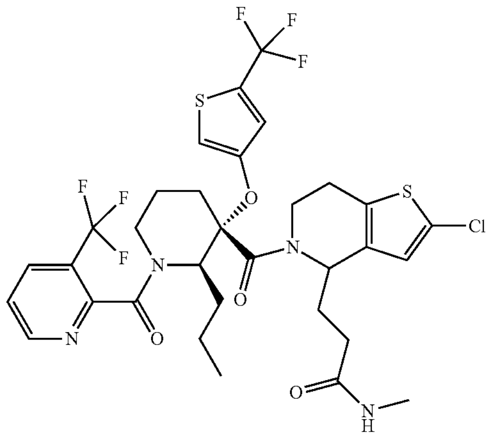 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCC(=O)NC] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-methylpropanamide | Calc'd 751.2, found 751 | B |
| A28 | 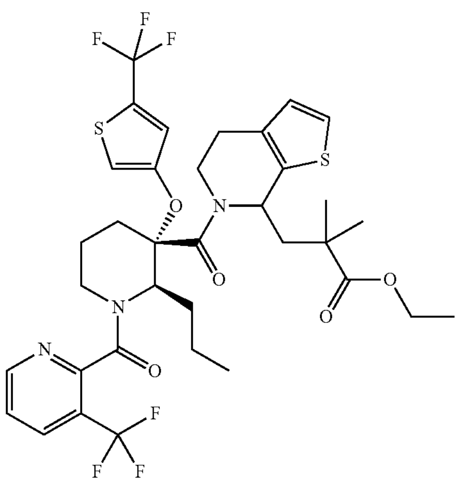 [SMILES: CCC[C@H]1N(C(=O)c2ncccc2C(F)(F)F)CCC[C@@]1(Oc1csc(C(F)(F)F)c1)C(=O)N1CCc2ccsc2C1CC(C)(C)C(=O)OCC] | ethyl 2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoate | Calc'd 760.2, found 760.1 | B |
| A29 | 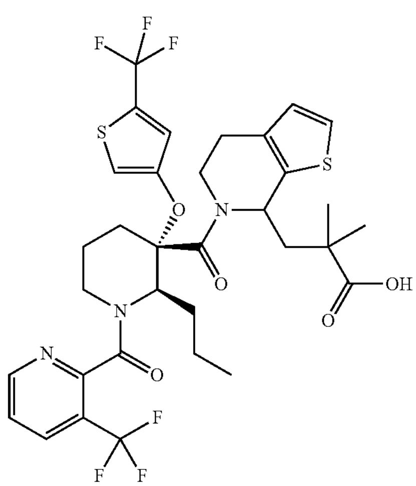 [SMILES: CCC[C@H]1N(C(=O)c2ncccc2C(F)(F)F)CCC[C@@]1(Oc1csc(C(F)(F)F)c1)C(=O)N1CCc2ccsc2C1CC(C)(C)C(=O)O] | 2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoic acid | Calc'd 732.2, found 732.1 | A |

| Name | Structure | IUPAC Name | Exact Mass [M + H]+ | FP IC50 (um) |
|---|---|---|---|---|
| A30 | 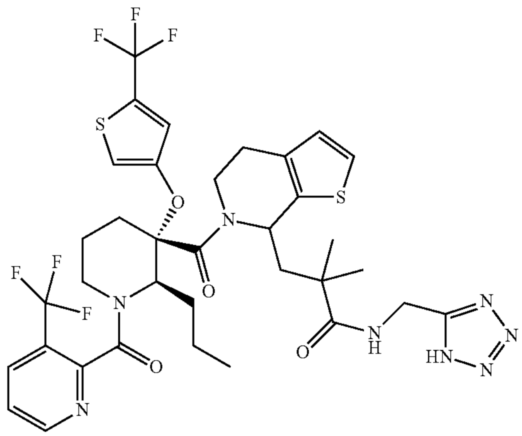 [SMILES: CCC[C@H]1N(C(=O)c2ncccc2C(F)(F)F)CCC[C@@]1(Oc1csc(C(F)(F)F)c1)C(=O)N1CCc2ccsc2C1CC(C)(C)C(=O)NCc1nnn[nH]1] | 2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-N-(1H-tetrazol-5-ylmethyl)propanamide | Calc'd 813.2, found 813.1 | A |
| A31 | 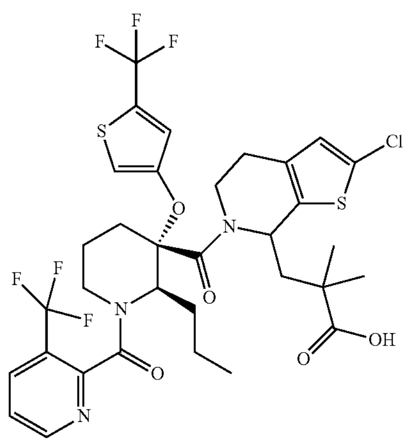 [SMILES: CCC[C@H]1N(C(=O)c2ncccc2C(F)(F)F)CCC[C@@]1(Oc1csc(C(F)(F)F)c1)C(=O)N1CCc2cc(Cl)sc2C1CC(C)(C)C(=O)O] | 3-(2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-2,2-dimethylpropanoic acid | Calc'd 766.2, found 766.2 | A |
| A32 | 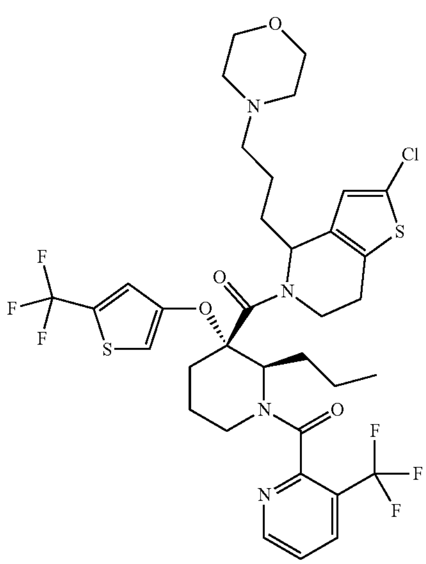 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCCN1CCOCC1] | 2-chloro-4-(3-morpholin-4-ylpropyl)-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine | Calc'd 793.2, found 793.2 | B |

-continued

| Name | Structure | IUPAC Name | Exact Mass [M + H]+ | FP IC50 (um) |
|---|---|---|---|---|
| A33 | 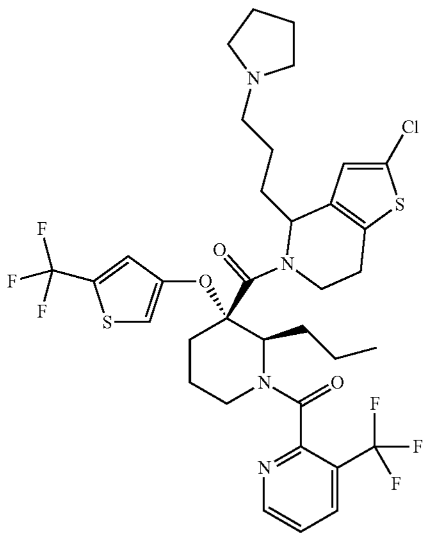 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCCN1CCCC1] | 2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(3-pyrrolidin-1-ylpropyl)-4,5,6,7-tetrahydrothieno[3,2-c]pyridine | Calc'd 777.2, found 777.1 | B |
| A34 | 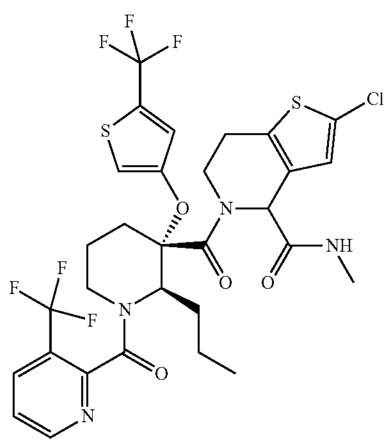 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1C(=O)NC] | 2-chloro-N-methyl-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxamide | Calc'd 723.1, found 723 | B |
| A35 | 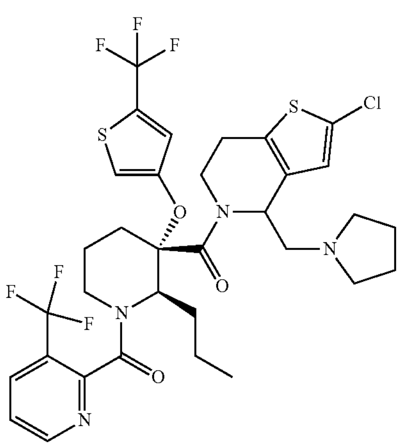 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CN1CCCC1] | 2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(pyrrolidin-1-ylmethyl)-4,5,6,7-tetrahydrothieno[3,2-c]pyridine | Calc'd 749.2, found 749.1 | B |

| Name | Structure | IUPAC Name | Exact Mass [M + H]+ | FP IC50 (um) |
|---|---|---|---|---|
| A36 | 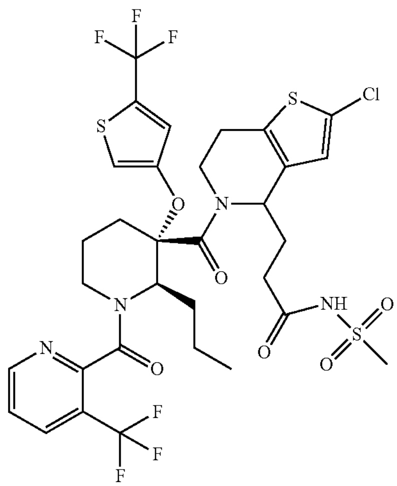 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCC(=O)NS(C)(=O)=O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl) propanamide | Calc'd 815.1, found 814.7 | A |
| A37 | 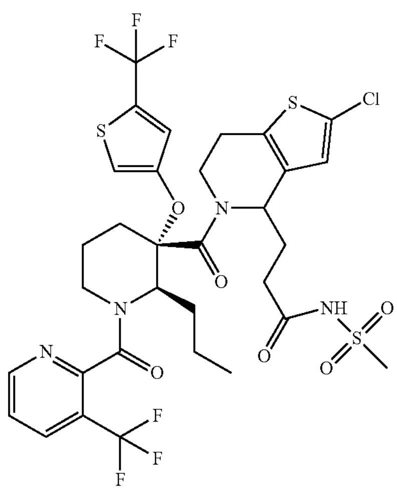 [SMILES: CCC[C@H]1N(C(=O)c2ncccc2C(F)(F)F)CCC[C@@]1(Oc1csc(C(F)(F)F)c1)C(=O)N1CCc2sc(Cl)cc2C1CCC(=O)NS(C)(=O)=O] | 3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl) propanamide | Calc'd 815.1, found 814.7 | A |
| A38 | 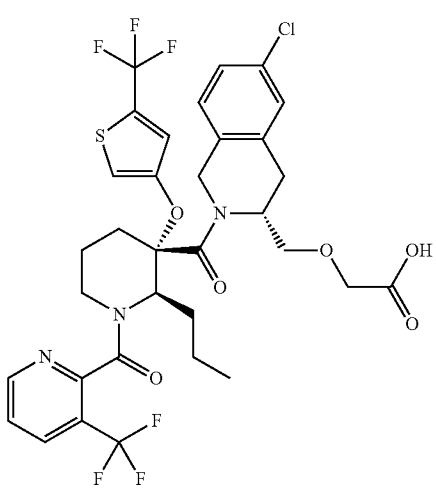 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1COCC(=O)O] | {[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methoxy}acetic acid | Calc'd 748.2, found 747.8 | A |

| Name | Structure | IUPAC Name | Exact Mass [M + H]+ | FP IC50 (um) |
|---|---|---|---|---|
| A39 | 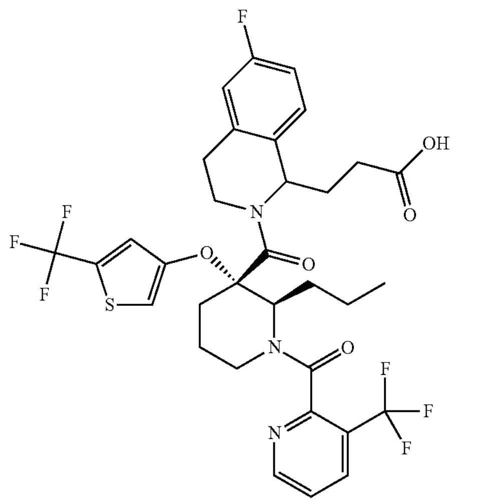 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCC(=O)O] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid | Calc'd 716.2, found 716.02 | A |
| A40 | 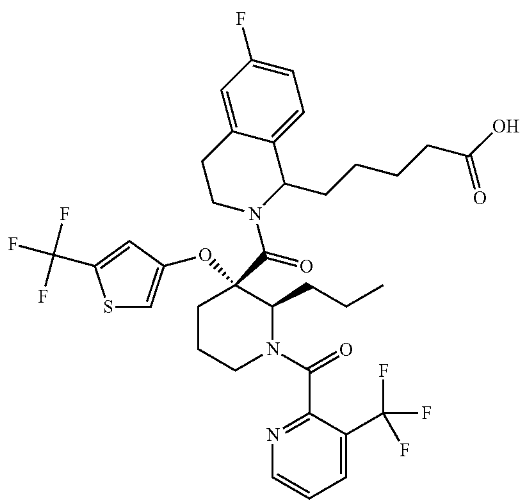 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCCCC(=O)O] | 5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid | Calc'd 744.2, found 744.2 | A |
| A41 | 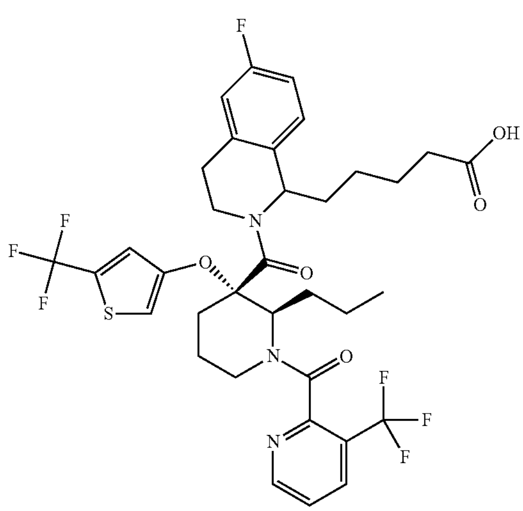 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCCCC(=O)O] | 5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid | Calc'd 744.2, found 744.2 | A |

-continued

| Name | Structure | IUPAC Name | Exact Mass [M + H]+ | FP IC50 (um) |
|---|---|---|---|---|
| A42 | 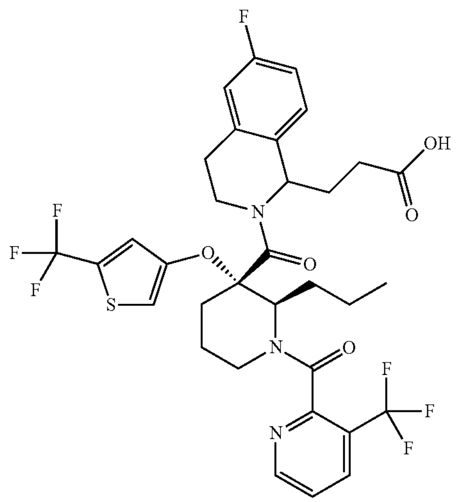 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCC(=O)O] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid | Calc'd 716.2, found 716.2 | A |
| A43 | 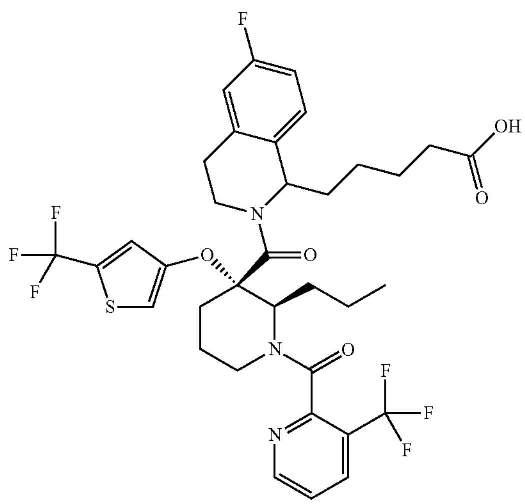 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCCCC(=O)O] | 5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid | Calc'd 744.2, found 744.2 | A |
| A44 | 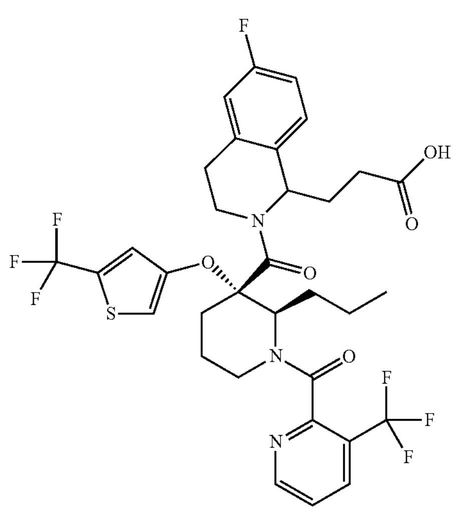 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCC(=O)O] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid | Calc'd 716.2, found 716.2 | A |

-continued

| Name | Structure | IUPAC Name | Exact Mass [M + H]+ | FP IC50 (um) |
|---|---|---|---|---|
| A45 | 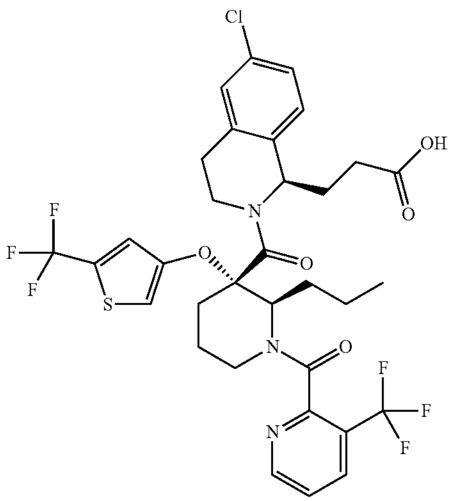 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@H]1CCC(=O)O] | 3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoic acid | Calc'd 732.2, found 732.1 | A |
| A46 | 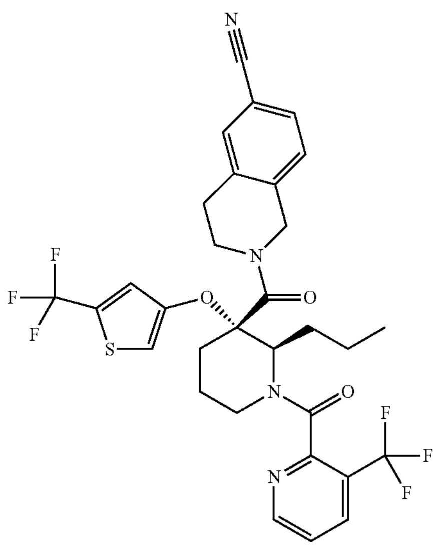 [SMILES: CCC[C@H]1N(C(=O)c2ncccc2C(F)(F)F)CCC[C@@]1(Oc1csc(C(F)(F)F)c1)C(=O)N1CCc2cc(C#N)ccc2C1] | 2-{[(2R,3S)-2-propyl-1-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carbonitrile | Calc'd 651.2, found 651.1 | B |
| A47 | 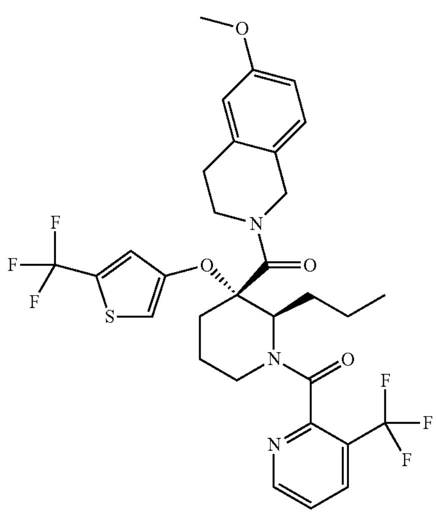 [SMILES: CCC[C@H]1N(C(=O)c2ncccc2C(F)(F)F)CCC[C@@]1(Oc1csc(C(F)(F)F)c1)C(=O)N1CCc2cc(OC)ccc2C1] | 6-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 656.2, found 656.2 | B |

-continued

| Name | Structure | IUPAC Name | Exact Mass [M + H]+ | FP IC50 (um) |
|---|---|---|---|---|
| A48 | 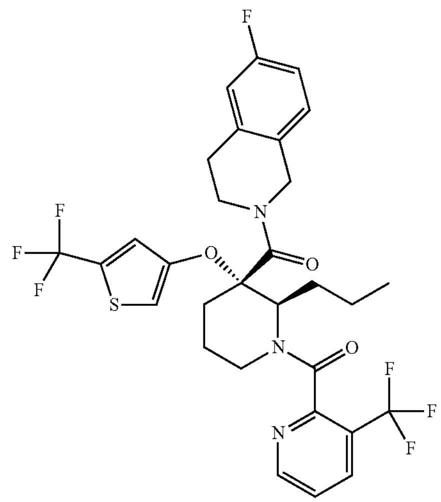 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1] | 6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 644.2, found 644.2 | B |
| A49 | 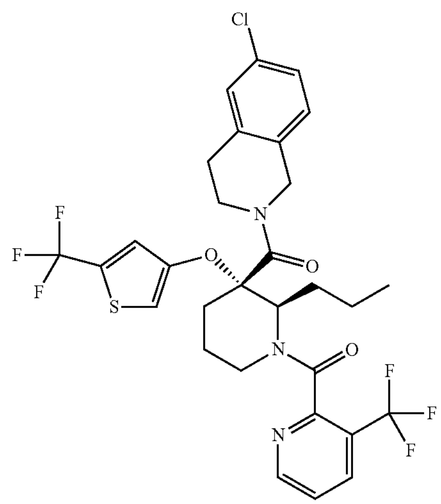 | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 660.2, found 660 | A |
| A50 | 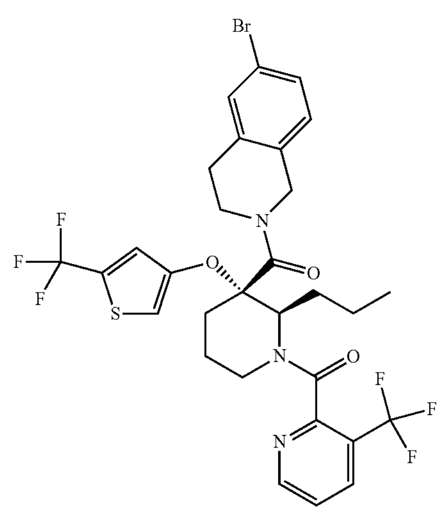 [SMILES: CCC[C@H]1N(C(=O)c2ncccc2C(F)(F)F)CCC[C@@]1(Oc1csc(C(F)(F)F)c1)C(=O)N1CCc2cc(Br)ccc2C1] | 6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 704.1, found 704 | A |

-continued

| Name | Structure | IUPAC Name | Exact Mass [M + H]+ | FP IC50 (um) |
|---|---|---|---|---|
| A51 | 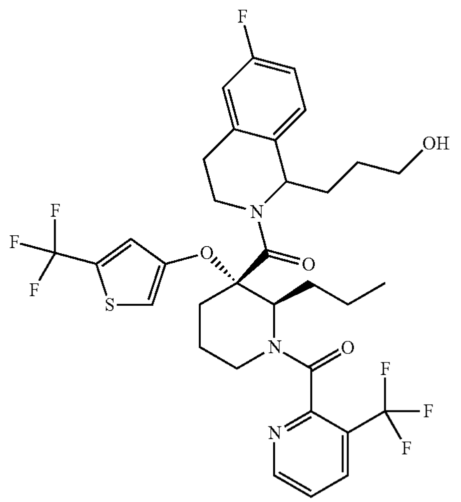 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCCO] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol | Calc'd 702.2, found 702.2 | A |
| A52 | 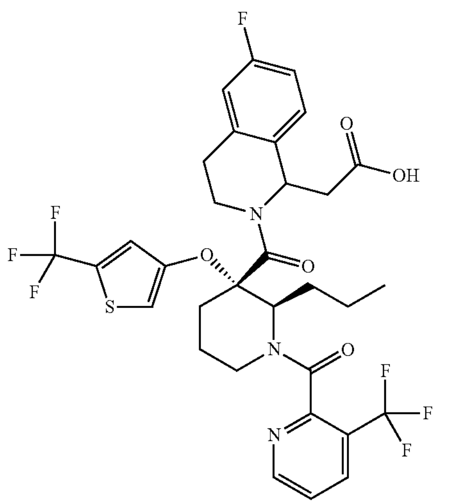 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CC(=O)O] | (6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid | Calc'd 702.2, found 702.2 | A |
| A53 | 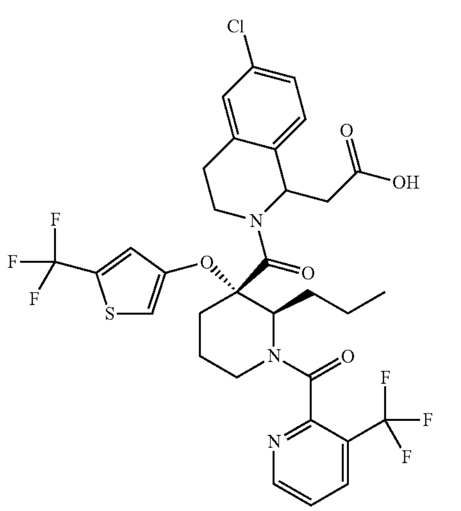 | (6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid | Calc'd 718.2, found 718.2 | A |

| Name | Structure | IUPAC Name | Exact Mass [M + H]+ | FP IC50 (um) |
|---|---|---|---|---|
| A54 | 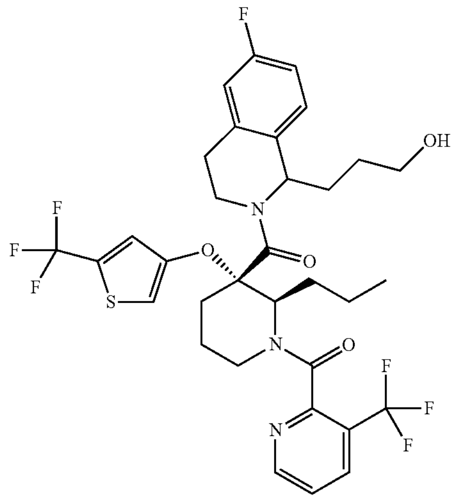 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCCO] | 3-(6-fludro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol | Calc'd 702.2, found 702.2 | B |
| A55 | 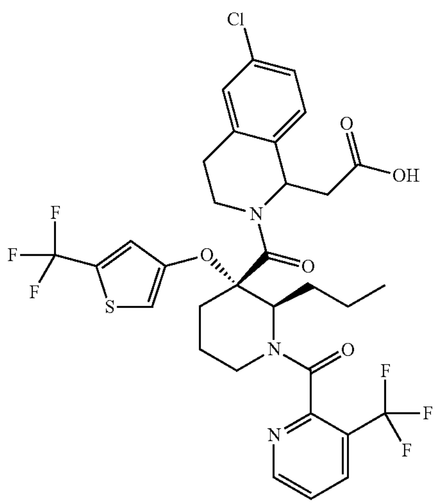 | (6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-.tetrahydroisoquinolin-1-yl)acetic acid | Calc'd 718.2, found 718.2 | A |
| A56 | 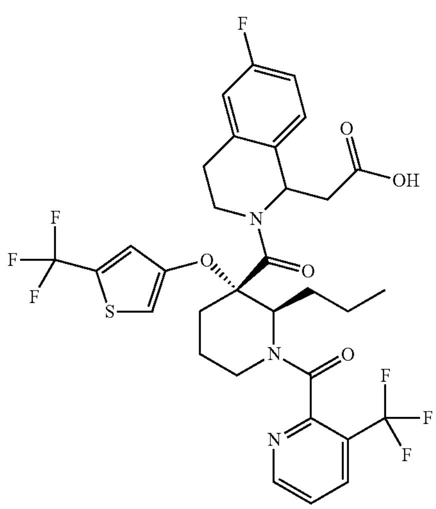 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CC(=O)O] | (6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-.tetrahydroisoquinolin-1-yl)acetic acid | Calc'd 702.2, found 702.2 | A |

| Name | Structure | IUPAC Name | Exact Mass [M + H]+ | FP IC50 (um) |
|---|---|---|---|---|
| A57 | 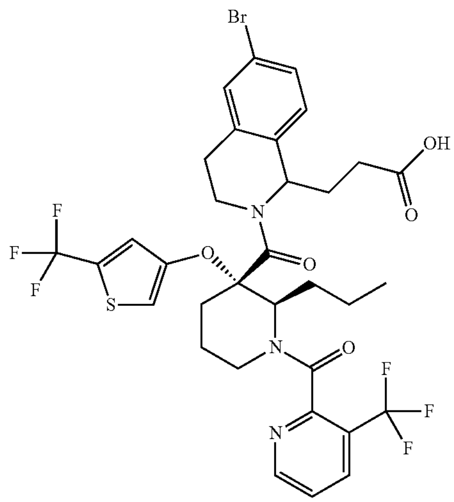 [SMILES: CCC[C@H]1N(C(=O)c2ncccc2C(F)(F)F)CCC[C@@]1(Oc1csc(C(F)(F)F)c1)C(=O)N1CCc2cc(Br)ccc2C1CCC(=O)O] | 3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid | Calc'd 776.1, found 776 | A |
| A58 | 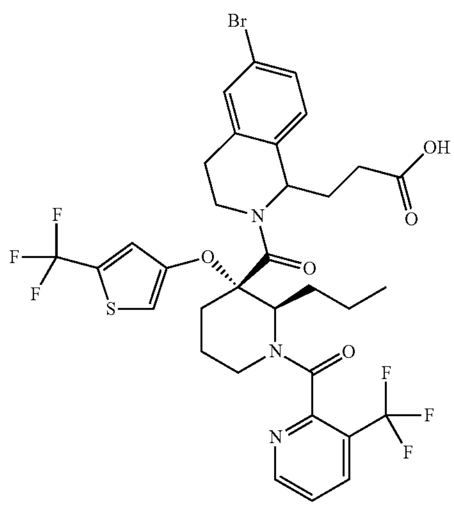 [SMILES: CCC[C@H]1N(C(=O)c2ncccc2C(F)(F)F)CCC[C@@]1(Oc1csc(C(F)(F)F)c1)C(=O)N1CCc2cc(Br)ccc2C1CCC(=O)O] | 3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid | Calc'd 776.1, found 776 | A |
| A59 | 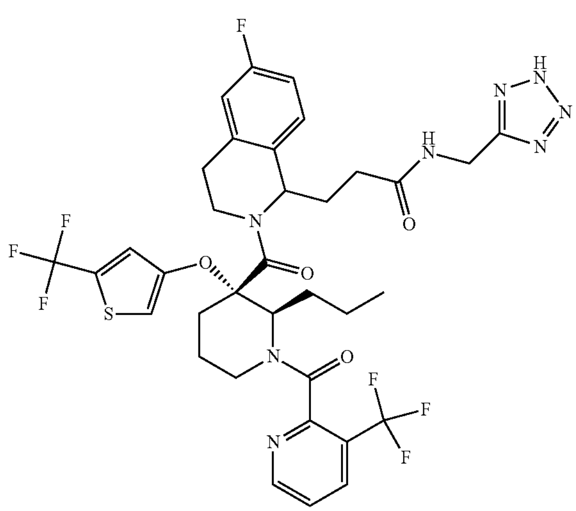 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCC(=O)NCc1nn[nH]n1] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide | Calc'd 797.2, found 797 | A |

-continued

| Name | Structure | IUPAC Name | Exact Mass [M + H]+ | FP IC50 (um) |
|---|---|---|---|---|
| A60 | 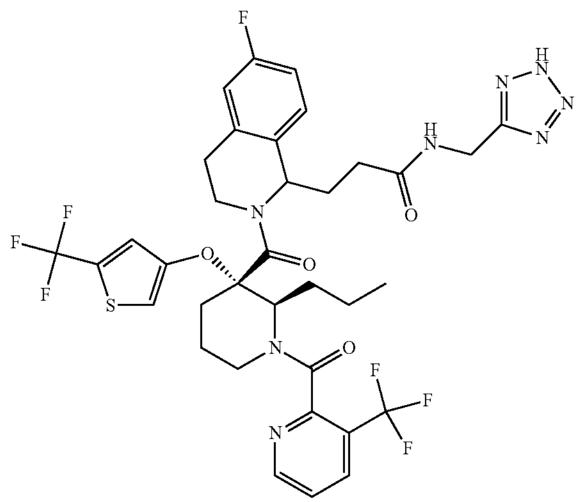 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1CCC(=O)NCc1nn[nH]n1] | 3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide | Calc'd 797.2, found 797.1 | A |
| A61 | 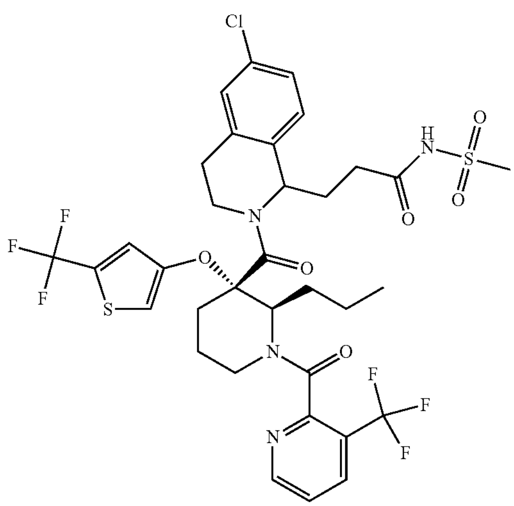 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CCC(=O)NS(C)(=O)=O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl)propanamide | Calc'd 809.2, found 808.9 | A |
| A62 | 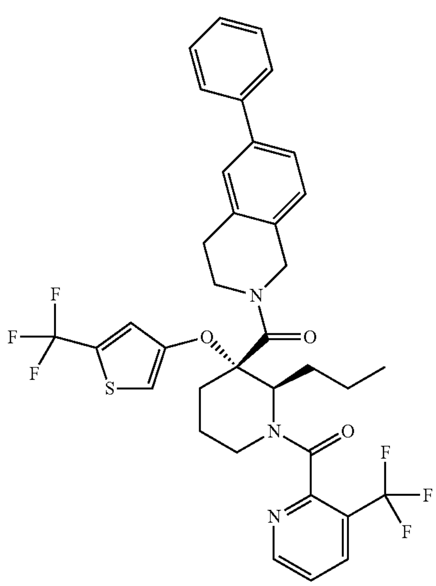 [SMILES: CCC[C@H]1N(C(=O)c2ncccc2C(F)(F)F)CCC[C@@]1(Oc1csc(C(F)(F)F)c1)C(=O)N1CCc2cc(-c3ccccc3)ccc2C1] | 6-phenyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 702.2, found 702.1 | B |

-continued

| Name | Structure | IUPAC Name | Exact Mass [M + H]+ | FP IC50 (um) |
|---|---|---|---|---|
| A63 | 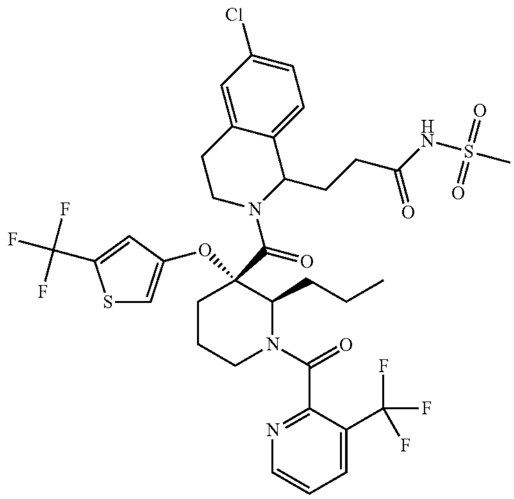 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CCC(=O)NS(C)(=O)=O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl) propanamide | Calc'd 809.2, found 809 | A |
| A64 | 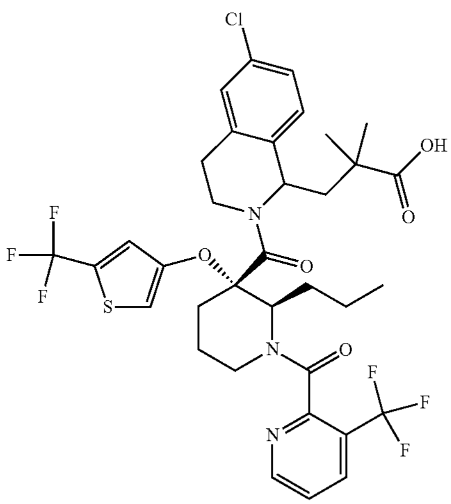 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C(=O)O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid | Calc'd 760.2, found 760.2 | A |
| A65 | 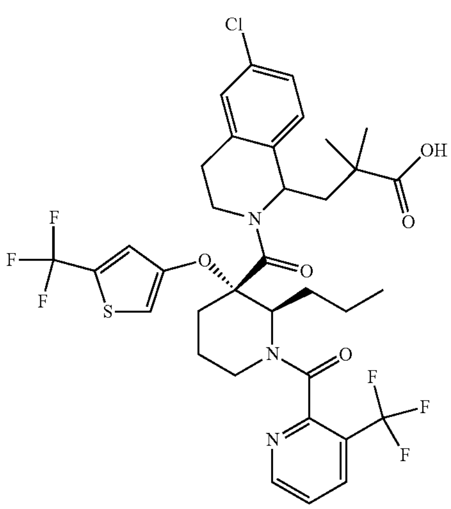 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C(=O)O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid | Calc'd 760.2, found 760.2 | A |

-continued

| Name | Structure | IUPAC Name | Exact Mass [M + H]+ | FP IC50 (um) |
|---|---|---|---|---|
| A66 | 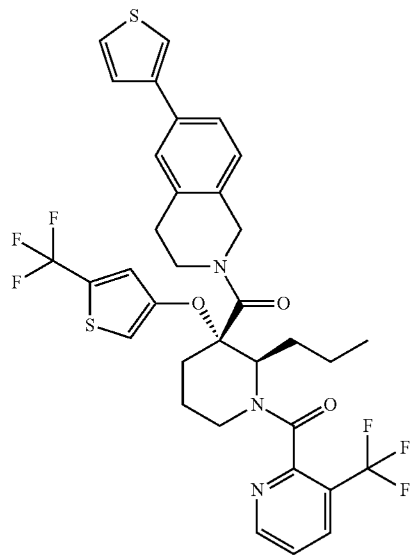 [SMILES: CCC[C@H]1N(C(=O)c2ncccc2C(F)(F)F)CCC[C@@]1(Oc1csc(C(F)(F)F)c1)C(=O)N1CCc2cc(-c3ccsc3)ccc2C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-6-thiophen-3-yl-1,2,3,4-tetrahydroisoquinoline | Calc'd 708.2, found 708.1 | B |
| A67 | 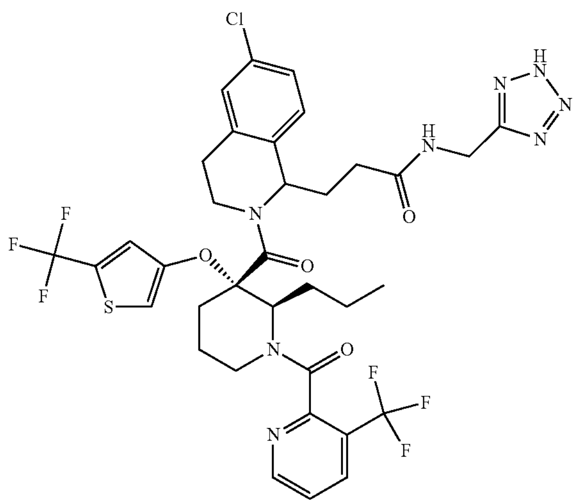 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CCC(=O)NCc1nn[nH]n1] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide | Calc'd 813.2, found 813.1 | A |
| A68 | 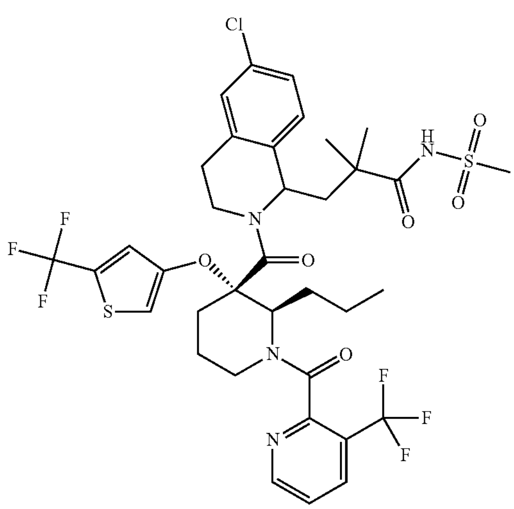 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C(=O)NS(C)(=O)=O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethyl-N-(methylsulfonyl)propanamide (stereoisomer 1) | Calc'd 837.2, found 837.1 | A |

| Name | Structure | IUPAC Name | Exact Mass [M + H]+ | FP IC50 (um) |
|---|---|---|---|---|
| A69 | 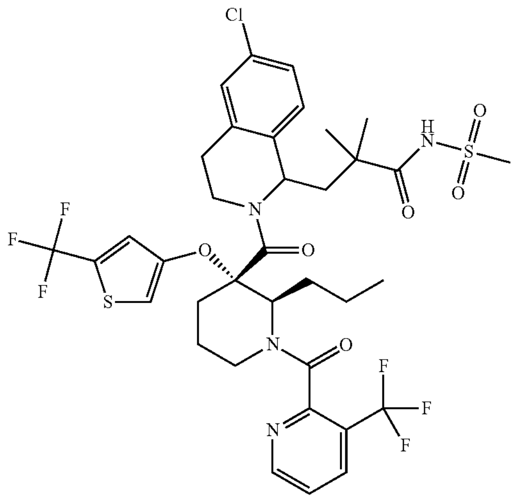 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C(=O)NS(C)(=O)=O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethyl-N-(methylsulfonyl)propanamide (stereoisomer 2) | Calc'd 837.2, found 837.1 | A |
| A70 | 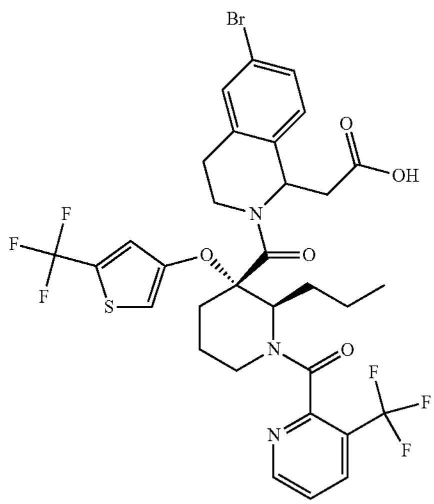 [SMILES: CCC[C@H]1N(C(=O)c2ncccc2C(F)(F)F)CCC[C@@]1(Oc1csc(C(F)(F)F)c1)C(=O)N1CCc2cc(Br)ccc2C1CC(=O)O] | (6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid | Calc'd 762.1, found 762.1 | A |
| A71 | 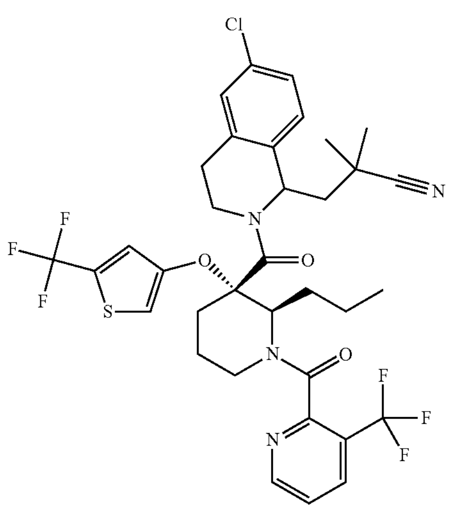 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C#N] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanenitrile | Calc'd 741.2, found 741.1 | B |

-continued

| Name | Structure | IUPAC Name | Exact Mass [M + H]+ | FP IC50 (um) |
|------|-----------|------------|---------------------|--------------|
| A72 | 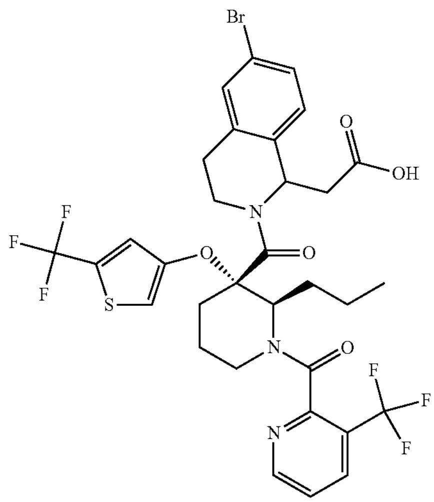 [SMILES: CCC[C@H]1N(C(=O)c2ncccc2C(F)(F)F)CCC[C@@]1(Oc1csc(C(F)(F)F)c1)C(=O)N1CCc2cc(Br)ccc2C1CC(=O)O] | (6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid | Calc'd 762.1, found 762.1 | A |
| A73 | 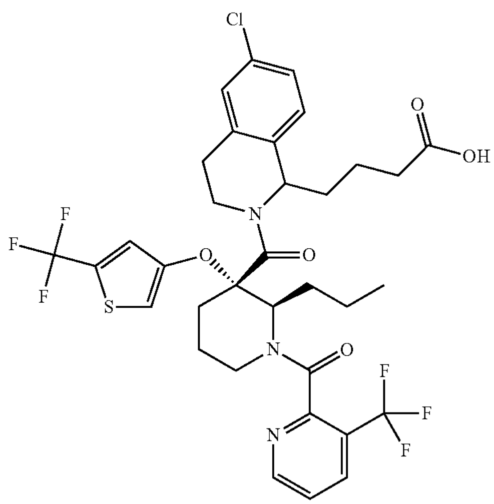 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CCCC(=O)O] | 4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid | Calc'd 746.2, found 746 | A |
| A74 | 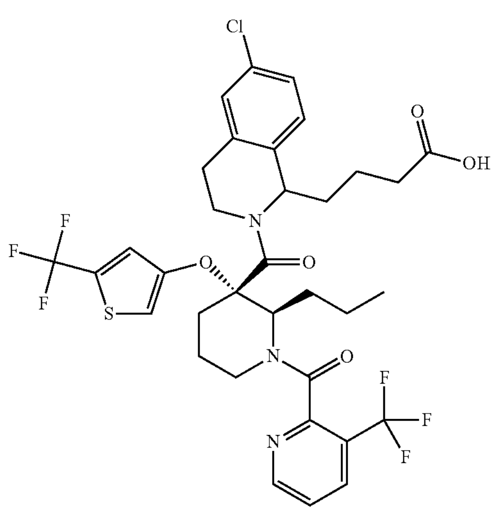 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CCCC(=O)O] | 4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid | Calc'd 746.2, found 746 | A |

-continued

| Name | Structure | IUPAC Name | Exact Mass [M + H]+ | FP IC50 (um) |
|---|---|---|---|---|
| A75 | 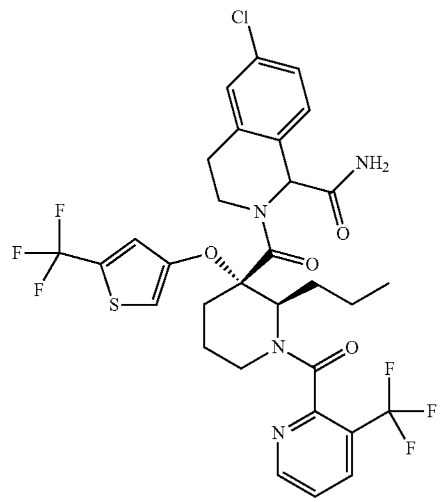 | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide | Calc'd 703.2, found 703 | A |
| A76 | 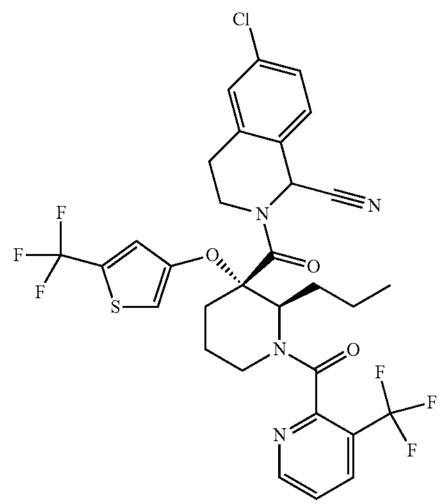 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C#N] | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carbonitrile | Calc'd 685.1, found 684.9 | B |
| A77 | 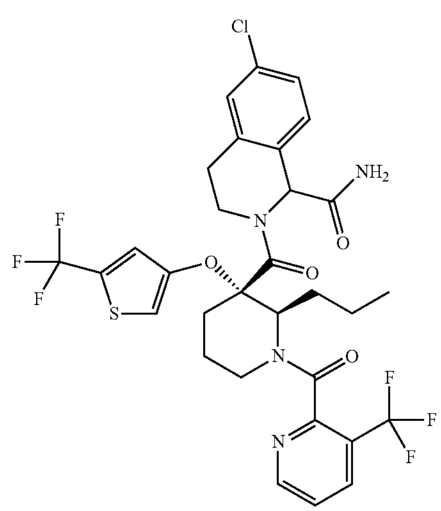 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C(N)=O] | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide | Calc'd 703.2, found 703 | A |

-continued

| Name | Structure | IUPAC Name | Exact Mass [M + H]+ | FP IC50 (um) |
|---|---|---|---|---|
| A78 | 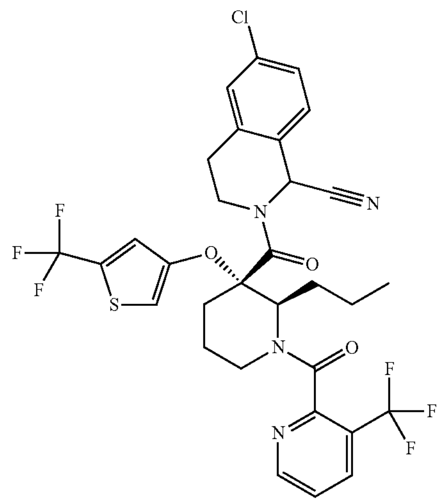 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C#N] | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carbonitrile | Calc'd 685.1, found 684.9 | B |
| A79 | 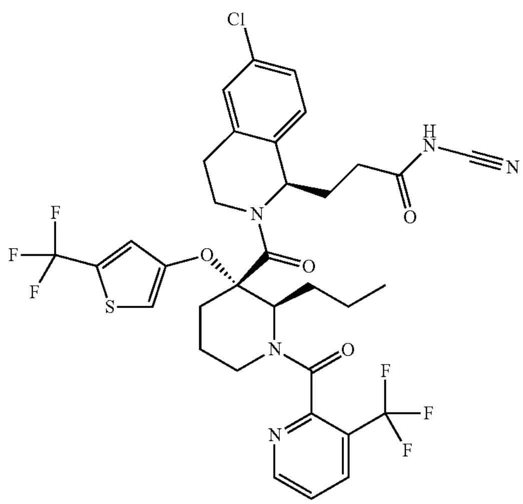 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@H]1CCC(=O)NC#N] | 3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]-N-cyanopropanamide | Calc'd 756.2, found 756 | A |
| A80 | 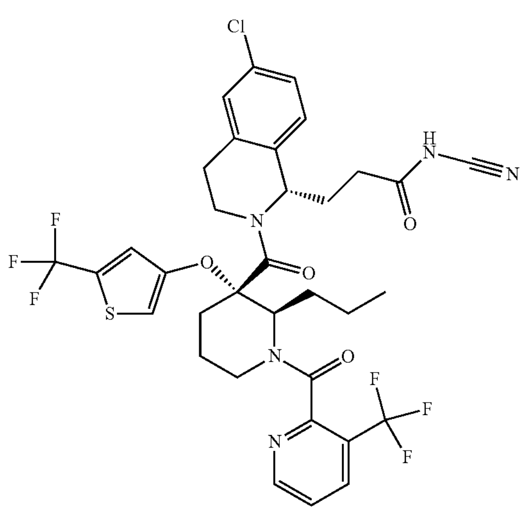 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@@H]1CCC(=O)NC#N] | 3-[(1S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]-N-cyanopropanamide | Calc'd 756.2, found 756.1 | A |

-continued

| Name | Structure | IUPAC Name | Exact Mass [M + H]+ | FP IC50 (um) |
|---|---|---|---|---|
| A81 | 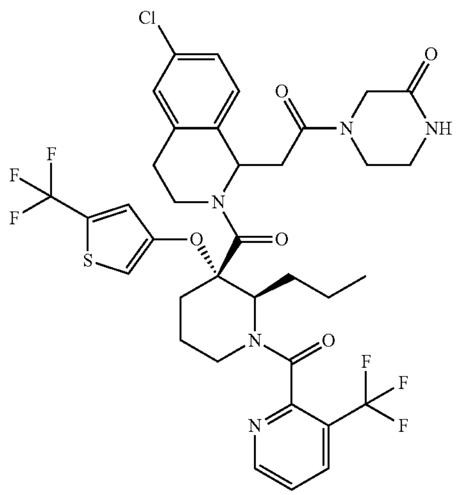 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(=O)N1CCNC(=O)C1] | 4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one | Calc'd 800.2, found 800 | A |
| A82 | 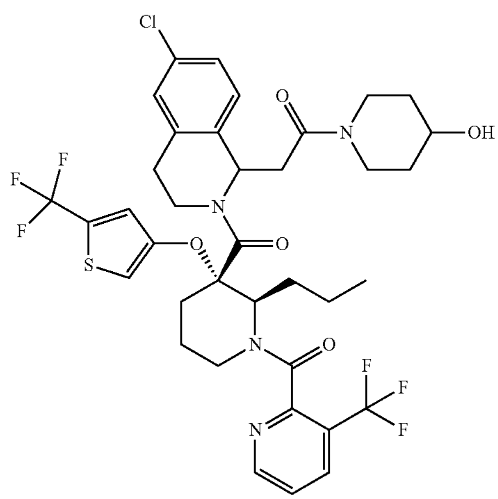 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(=O)N1CCC(O)CC1] | 1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol | Calc'd 801.2, found 801 | A |
| A83 | 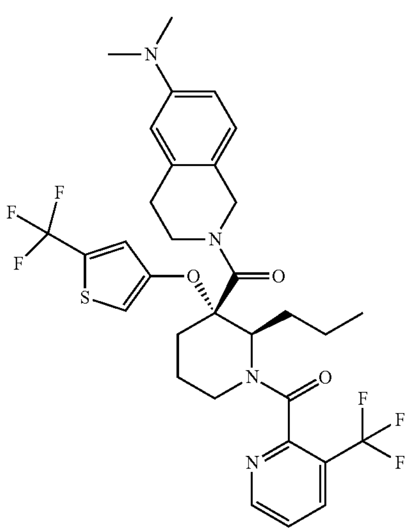 [SMILES: CCC[C@H]1N(C(=O)c2ncccc2C(F)(F)F)CCC[C@@]1(Oc1csc(C(F)(F)F)c1)C(=O)N1CCc2cc(N(C)C)ccc2C1] | N,N-dimethyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine | Calc'd 669.2, found 669.1 | B |

| Name | Structure | IUPAC Name | Exact Mass [M + H]+ | FP IC50 (um) |
|---|---|---|---|---|
| A84 | 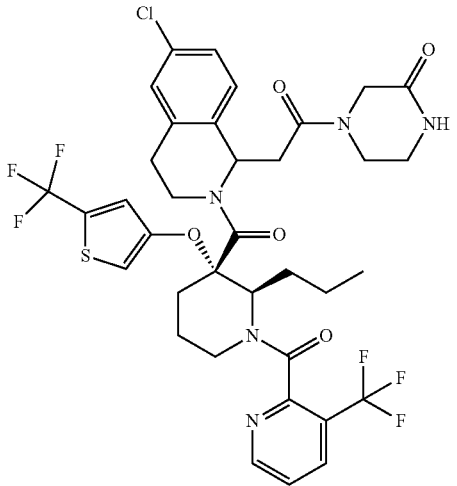 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(=O)N1CCNC(=O)C1] | 4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one | Calc'd 800.2, found 799.9 | A |
| A85 | 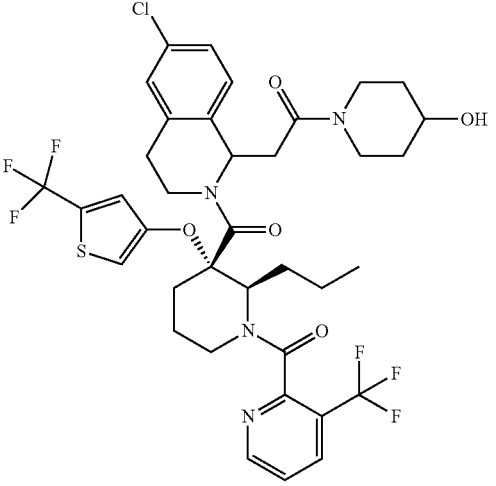 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(=O)N1CCC(O)CC1] | 1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol | Calc'd 801.2, found 801 | A |
| A86 | 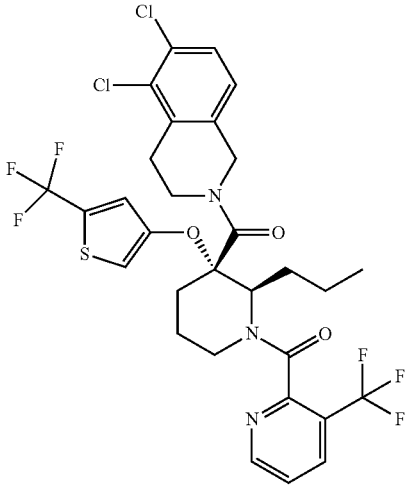 [SMILES: CCC[C@H]1N(C(=O)c2ncccc2C(F)(F)F)CCC[C@@]1(Oc1csc(C(F)(F)F)c1)C(=O)N1CCc2c(ccc(Cl)c2Cl)C1] | 5,6-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 694.1, found 694 | B |

| Name | Structure | IUPAC Name | Exact Mass [M + H]+ | FP IC50 (um) |
|---|---|---|---|---|
| A87 | 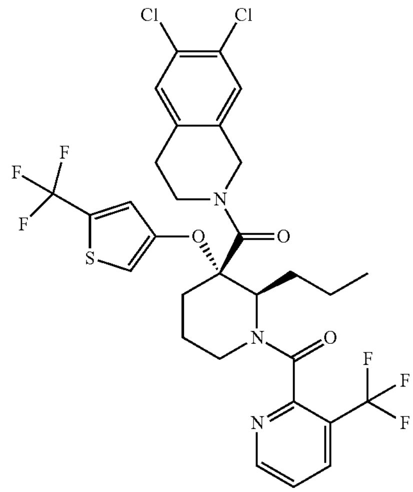 [SMILES: CCC[C@H]1N(C(=O)c2ncccc2C(F)(F)F)CCC[C@@]1(Oc1csc(C(F)(F)F)c1)C(=O)N1CCc2cc(Cl)c(Cl)cc2C1] | 6,7-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 694.1, found 694 | B |
| A88 | 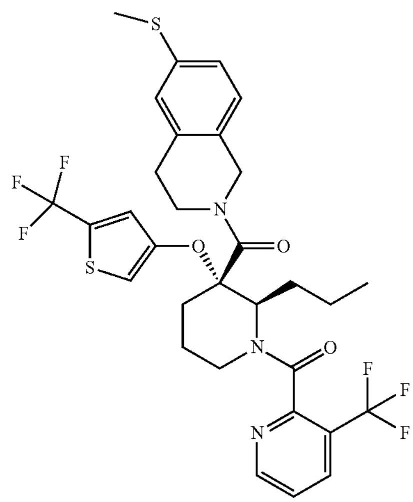 [SMILES: CCC[C@H]1N(C(=O)c2ncccc2C(F)(F)F)CCC[C@@]1(Oc1csc(C(F)(F)F)c1)C(=O)N1CCc2cc(SC)ccc2C1] | 6-(methylsulfanyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 672.2, found 672 | B |
| A89 | 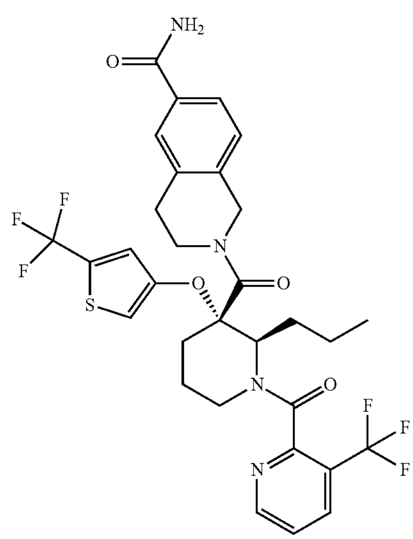 [SMILES: CCC[C@H]1N(C(=O)c2ncccc2C(F)(F)F)CCC[C@@]1(Oc1csc(C(F)(F)F)c1)C(=O)N1CCc2cc(C(N)=O)ccc2C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carboxamide | Calc'd 669.2, found 669 | B |

| Name | Structure | IUPAC Name | Exact Mass [M + H]+ | FP IC50 (um) |
|---|---|---|---|---|
| A90 | 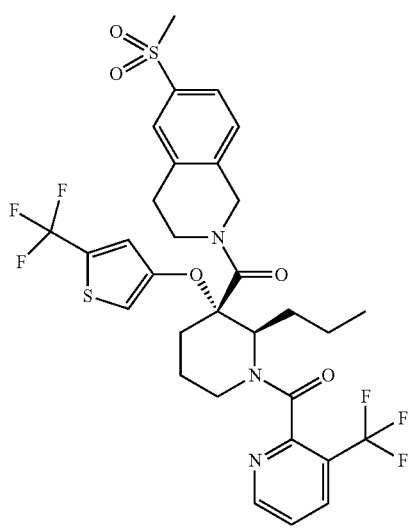 [SMILES: CCC[C@H]1N(C(=O)c2ncccc2C(F)(F)F)CCC[C@@]1(Oc1csc(C(F)(F)F)c1)C(=O)N1CCc2cc(S(C)(=O)=O)ccc2C1] | 6-(methylsulfonyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 704.2, found 704 | B |
| A91 | 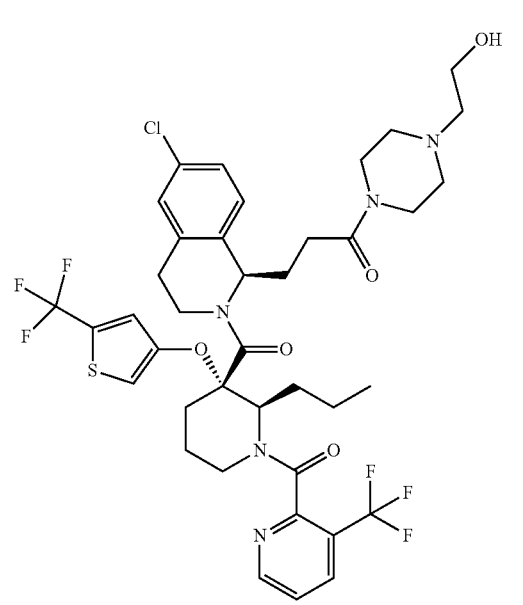 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@H]1CCC(=O)N1CCN(CCO)CC1] | 2-(4-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperazin-1-yl)ethanol | Calc'd 844.3, found 844 | A |

| Name | Structure | IUPAC Name | Exact Mass [M + H]+ | FP IC50 (um) |
|---|---|---|---|---|
| A92 | 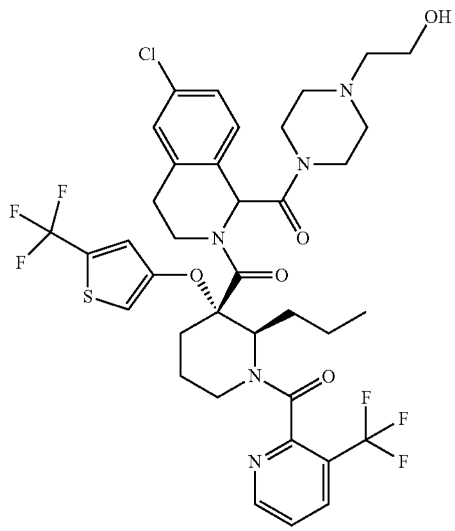 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C(=O)N1CCN(CCO)CC1] | 2-{4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol | Calc'd 816.2, found 816 | B |
| A93 | 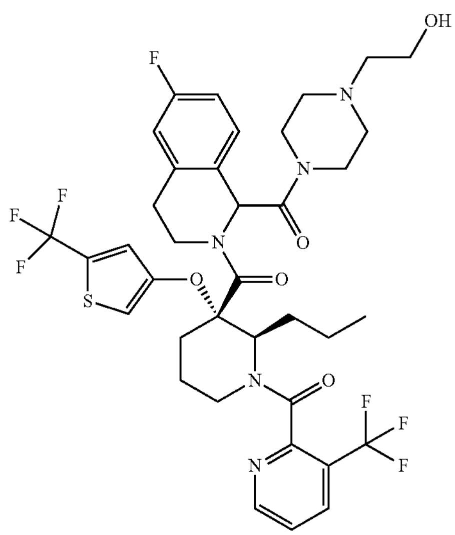 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1C(=O)N1CCN(CCO)CC1] | 2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol | Calc'd 800.3, found 800 | A |
| A94 | 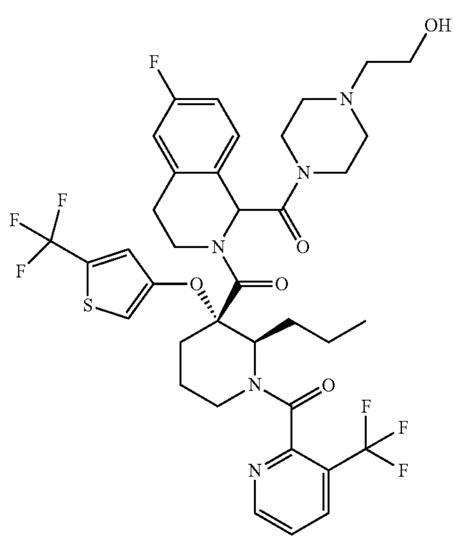 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1C(=O)N1CCN(CCO)CC1] | 2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol | Calc'd 800.3, found 799.9 | B |

| Name | Structure | IUPAC Name | Exact Mass [M + H]+ | FP IC50 (um) |
|---|---|---|---|---|
| A95 | 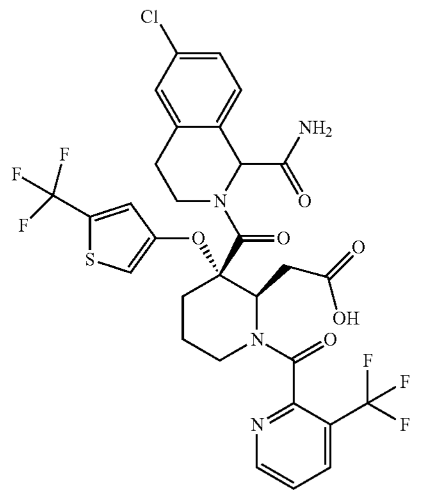 [SMILES: NC(=O)C1c2ccc(Cl)cc2CCN1C(=O)[C@]1(Oc2csc(C(F)(F)F)c2)CCCN(C(=O)c2ncccc2C(F)(F)F)[C@@H]1CC(=O)O] | [(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid | Calc'd 719.1, found 718.9 | A |
| A96 | 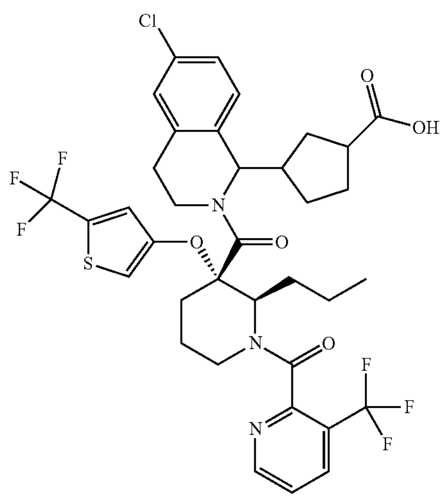 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C1CCC(C(=O)O)C1] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)cyclopentanecarboxylic acid | Calc'd 772.2, found 772 | A |
| A97 | 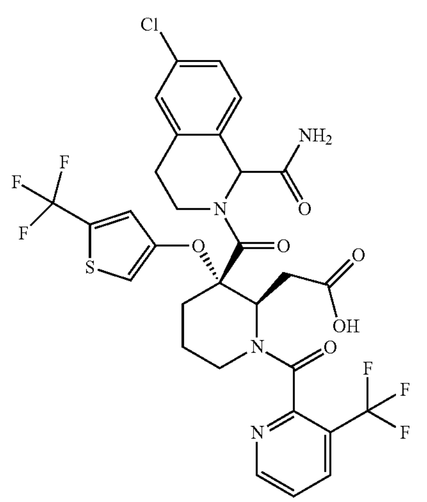 [SMILES: NC(=O)C1c2ccc(Cl)cc2CCN1C(=O)[C@]1(Oc2csc(C(F)(F)F)c2)CCCN(C(=O)c2ncccc2C(F)(F)F)[C@@H]1CC(=O)O] | [(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid | Calc'd 719.1, found 718.9 | A |

-continued

| Name | Structure | IUPAC Name | Exact Mass [M + H]+ | FP IC50 (um) |
|------|-----------|------------|---------------------|--------------|
| A98 | 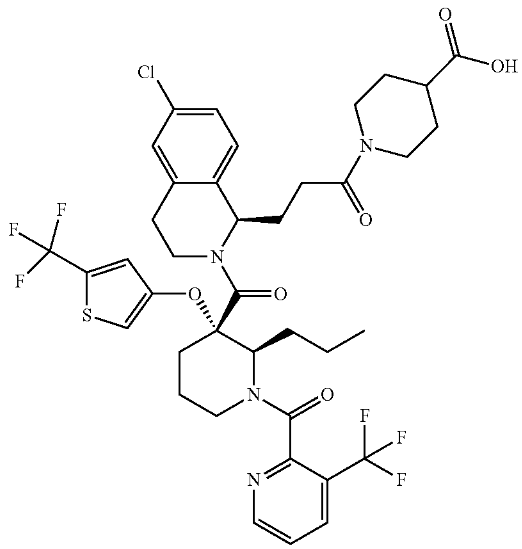 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@H]1CCC(=O)N1CCC(C(=O)O)CC1] | 1-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid | Calc'd 843.2, found 843.2 | A |
| A99 | 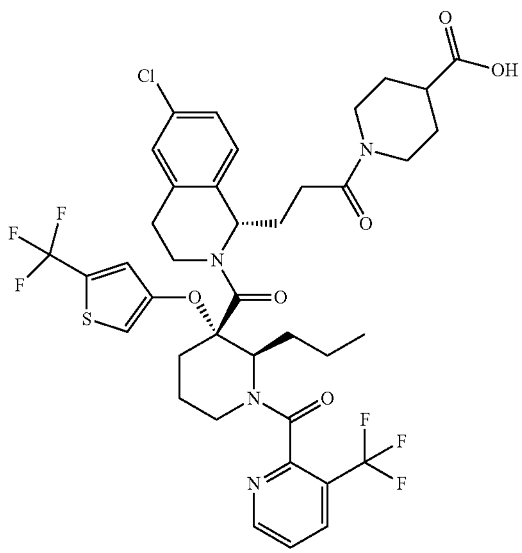 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2[C@@H]1CCC(=O)N1CCC(C(=O)O)CC1] | 1-{3-[(1S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid | Calc'd 843.2, found 843.2 | A |
| A100 | 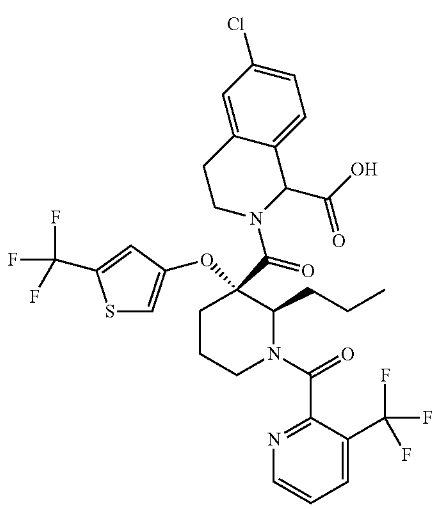 | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid | Calc'd 704.1, found 704 | A |

-continued

| Name | Structure | IUPAC Name | Exact Mass [M + H]+ | FP IC50 (um) |
|---|---|---|---|---|
| A101 | 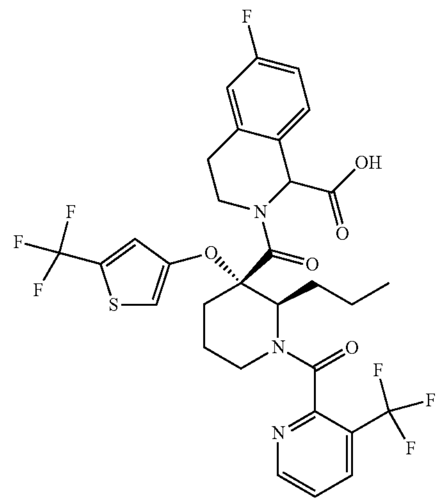 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1C(=O)O] | 6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid | Calc'd 688.2, found 688.2 | A |
| A102 | 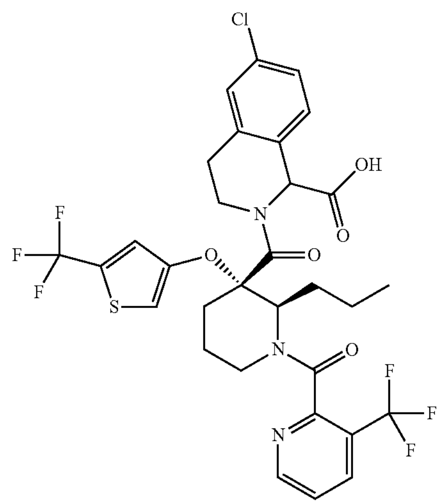 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1C(=O)O] | 6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid | Calc'd 704.1, found 704 | A |
| A103 | 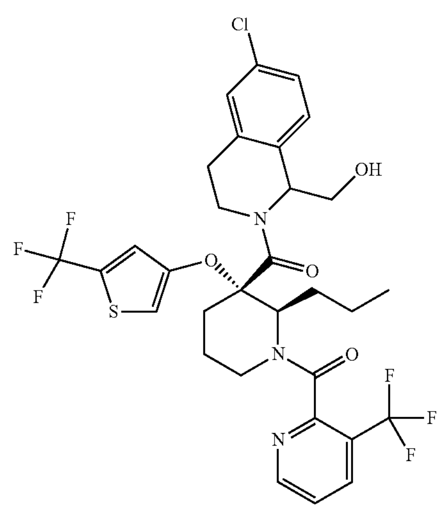 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CO] | (6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol | Calc'd 690.2, found 690.2 | B |

-continued

| Name | Structure | IUPAC Name | Exact Mass [M + H]+ | FP IC50 (um) |
|---|---|---|---|---|
| A104 | 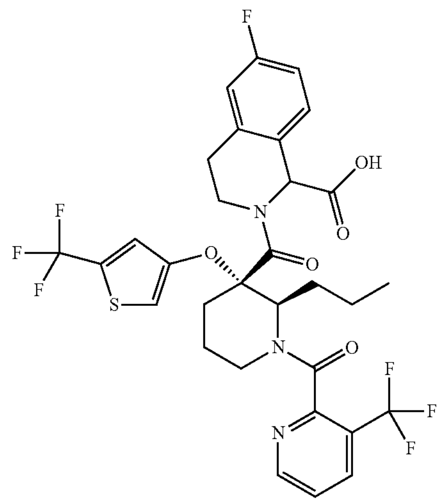 [SMILES: CCC[C@H]1N(C(=O)c2ncccc2C(F)(F)F)CCC[C@@]1(Oc1csc(C(F)(F)F)c1)C(=O)N1CCc2cc(F)ccc2C1C(=O)O] | 6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid | Calc'd 688.2, found 688.2 | A |
| A105 | 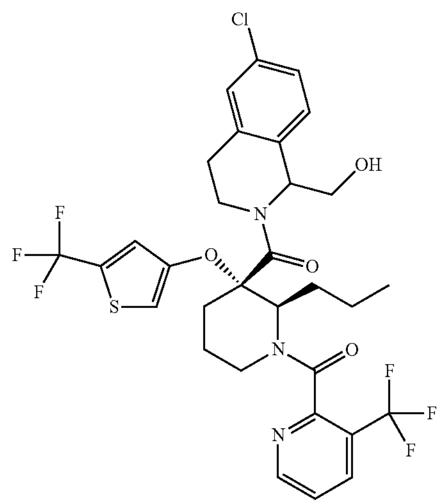 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CO] | (6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol | Calc'd 690.2, found 690.2 | B |
| A106 | 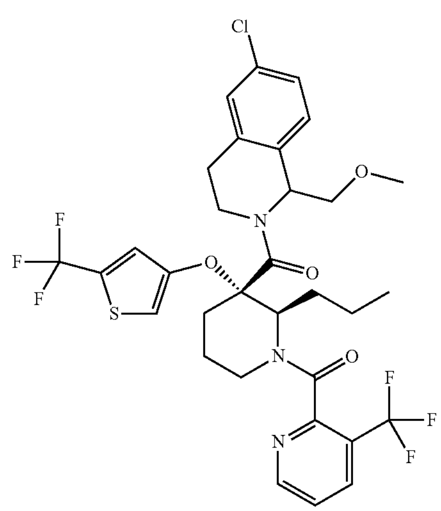 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1COC] | 6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 704.2, found 704.2 | A |

-continued

| Name | Structure | IUPAC Name | Exact Mass [M + H]+ | FP IC50 (um) |
|---|---|---|---|---|
| A107 | 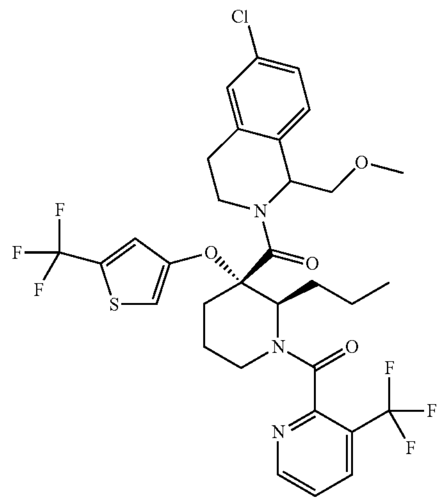 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1COC] | 6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 704.2, found 704.1 | B |
| A108 | 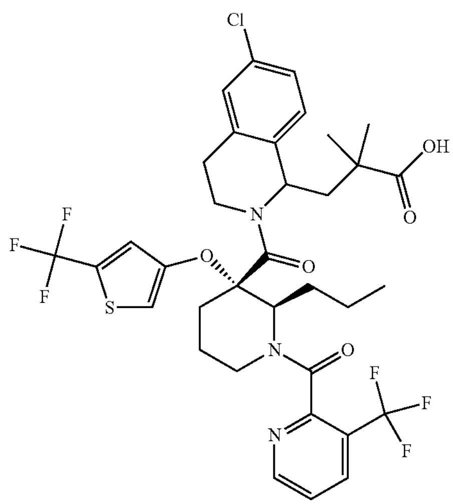 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)(C)C(=O)O] | 3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid | Calc'd 760.2, found 760.2 | A |
| A109 | 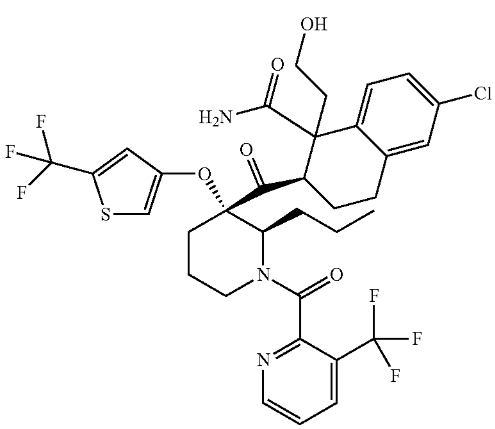 [SMILES: CCC[C@H]1N(C(=O)c2ncccc2C(F)(F)F)CCC[C@@]1(Oc1csc(C(F)(F)F)c1)C(=O)[C@@H]1CCc2cc(Cl)ccc2C1(CCO)C(N)=O] | 6-chloro-1-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide | Calc'd 747.2, found 746.8 | A |

| Name | Structure | IUPAC Name | Exact Mass [M + H]+ | FP IC50 (um) |
|---|---|---|---|---|
| A110 | 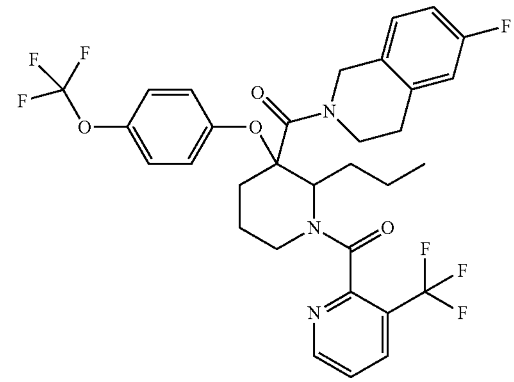 [SMILES: CCCC1N(C(=O)c2ncccc2C(F)(F)F)CCCC1(Oc1ccc(OC(F)(F)F)cc1)C(=O)N1CCc2cc(F)ccc2C1] | 6-fluoro-2-[(2-propyl-3-[4-(trifluoromethoxy)phenoxy]-1-{[3-(trifluoromethyl)pyridin-2-yl]carbonyl}piperidin-3-yl)carbonyl]-1,2,3,4-tetrahydroisoquinoline | Calc'd 654.2, found 654 | B |
| A111 | 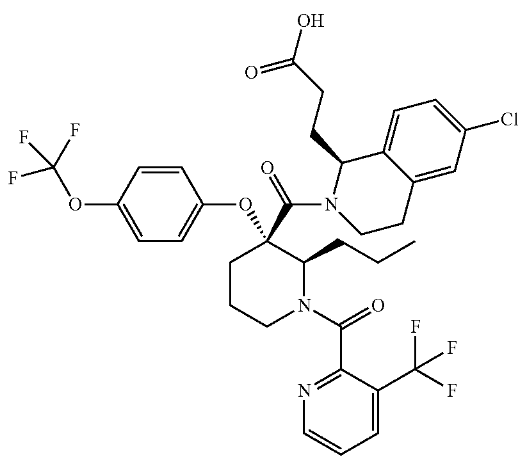 [SMILES: CCC[C@H]1N(C(=O)c2ncccc2C(F)(F)F)CCC[C@@]1(Oc1ccc(OC(F)(F)F)cc1)C(=O)N1CCc2cc(Cl)ccc2[C@@H]1CCC(=O)O] | 3-[(1S)-6-chloro-2-{[(2R,3S)-2-propyl-3-[4-(trifluoromethoxy)phenoxy]-1-{[3-(trifluoromethyl)pyridin-2-yl]carbonyl}piperidin-3-yl]carbonyl}-1,2,3,4-tetrahydroisoquinolin-1-yl]propanoic acid | Calc'd 742.2, found 741.8 | A |
| A112 | 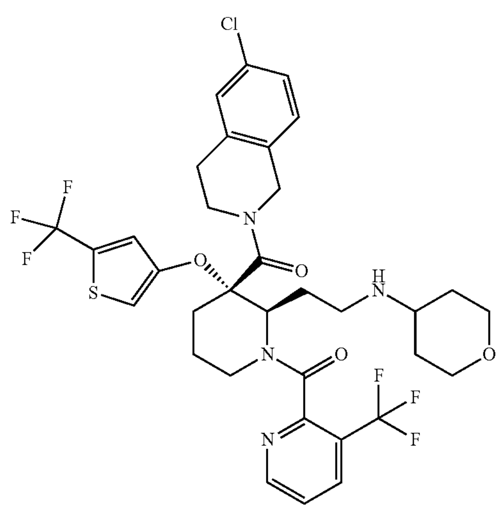 [SMILES: O=C(c1ncccc1C(F)(F)F)N1CCC[C@@](Oc2csc(C(F)(F)F)c2)(C(=O)N2CCc3cc(Cl)ccc3C2)[C@H]1CCNC1CCOCC1] | N-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine | Calc'd 745.2, found 745.2 | A |

| Name | Structure | IUPAC Name | Exact Mass [M + H]+ | FP IC50 (um) |
|---|---|---|---|---|
| A113 | 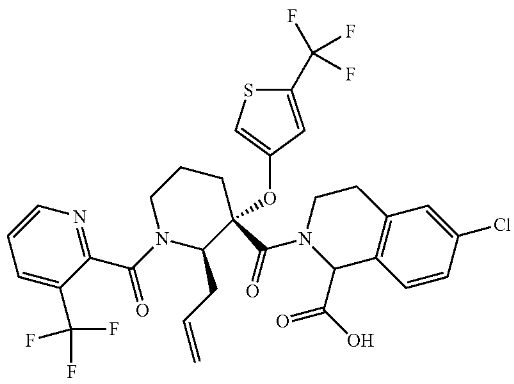 [SMILES: C=CC[C@H]1N(C(=O)c2ncccc2C(F)(F)F)CCC[C@@]1(Oc1csc(C(F)(F)F)c1)C(=O)N1CCc2cc(Cl)ccc2C1C(=O)O] | 6-chloro-2-{[(2R,3S)-2-prop-2-en-1-yl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid | Calc'd 702.1, found 702 | A |
| A114 | 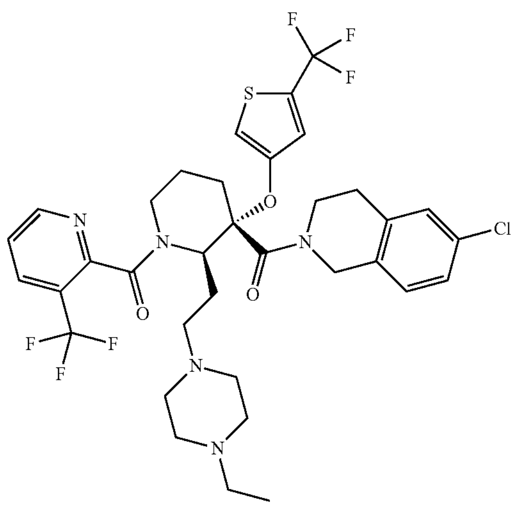 [SMILES: CCN1CCN(CC[C@H]2N(C(=O)c3ncccc3C(F)(F)F)CCC[C@@]2(Oc2csc(C(F)(F)F)c2)C(=O)N2CCc3cc(Cl)ccc3C2)CC1] | 6-chloro-2-{[(2R,3S)-2-[2-(4-ethylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 758.2, found 758.2 | A |
| A115 | 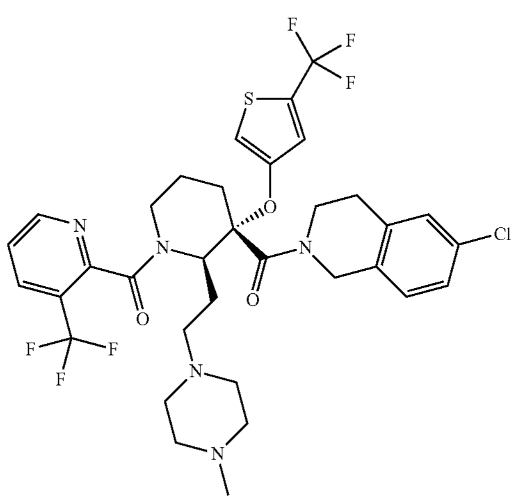 [SMILES: CN1CCN(CC[C@H]2N(C(=O)c3ncccc3C(F)(F)F)CCC[C@@]2(Oc2csc(C(F)(F)F)c2)C(=O)N2CCc3cc(Cl)ccc3C2)CC1] | 6-chloro-2-{[(2R,3S)-2-[2-(4-methylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 744.2, found 744.2 | A |

| Name | Structure | IUPAC Name | Exact Mass [M + H]+ | FP IC50 (um) |
|---|---|---|---|---|
| A116 | 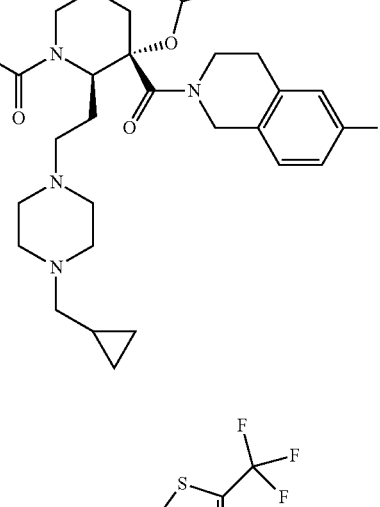 | 6-chloro-2-{[(2R,3S)-2-{2-[4-(cyclopropylmethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 784.3, found 784.2 | A |
| A117 | 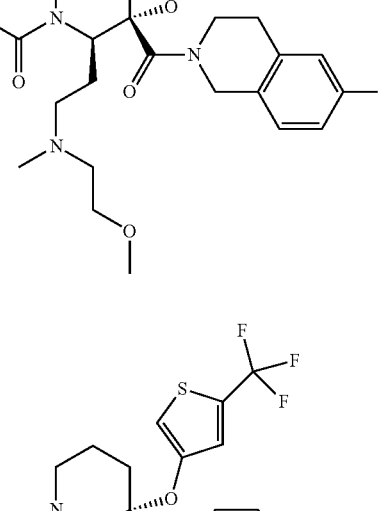 | 2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]-N-(2-methoxyethyl)-N-methylethanamine | Calc'd 733.2, found 733.2 | A |
| A118 | 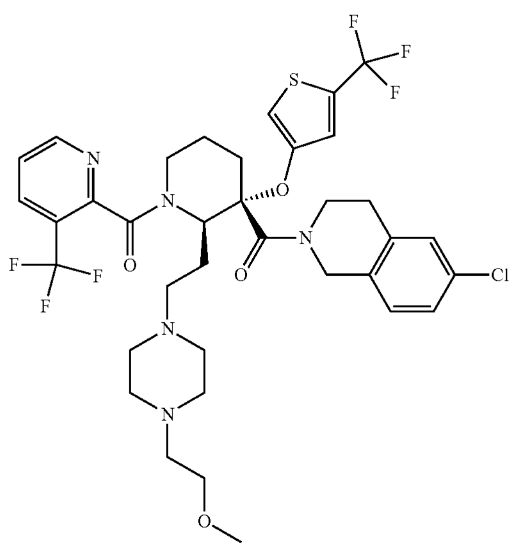 [SMILES: COCCN1CCN(CC[C@H]2N(C(=O)c3ncccc3C(F)(F)F)CCC[C@@]2(Oc2csc(C(F)(F)F)c2)C(=O)N2CCc3cc(Cl)ccc3C2)CC1] | 6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 788.2, found 788.2 | A |

-continued

| Name | Structure | IUPAC Name | Exact Mass [M + H]+ | FP IC50 (um) |
|---|---|---|---|---|
| A119 | 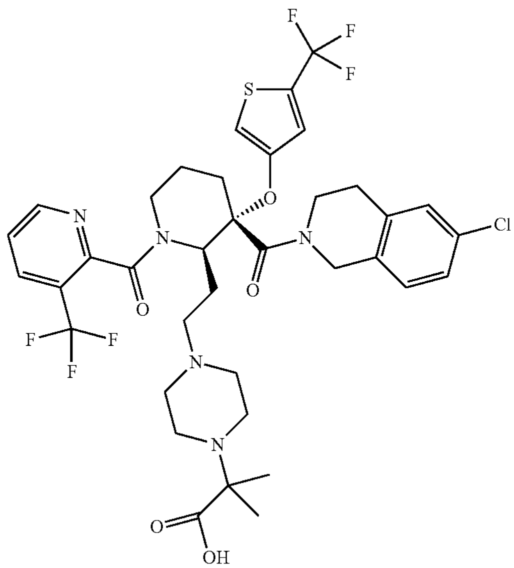 [SMILES: CC(C)(C(=O)O)N1CCN(CC[C@H]2N(C(=O)c3ncccc3C(F)(F)F)CCC[C@@]2(Oc2csc(C(F)(F)F)c2)C(=O)N2CCc3cc(Cl)ccc3C2)CC1] | 2-(1-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}piperidin-4-yl)-2-methylpropanoic acid | Calc'd 815.2, found 815.2 | A |
| A120 | 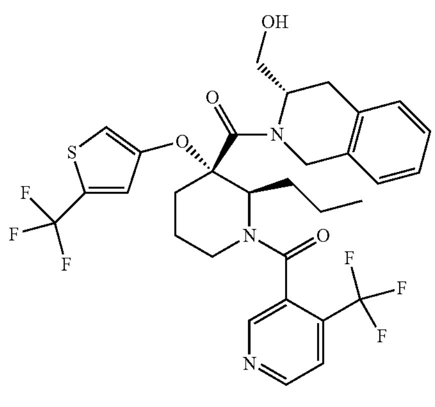 [SMILES: CCC[C@H]1N(C(=O)c2cnccc2C(F)(F)F)CCC[C@@]1(Oc1csc(C(F)(F)F)c1)C(=O)N1Cc2ccccc2C[C@H]1CO] | [(3S)-2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-3-yl]methanol | Calc'd 656.2, found 656 | B |
| A121 | 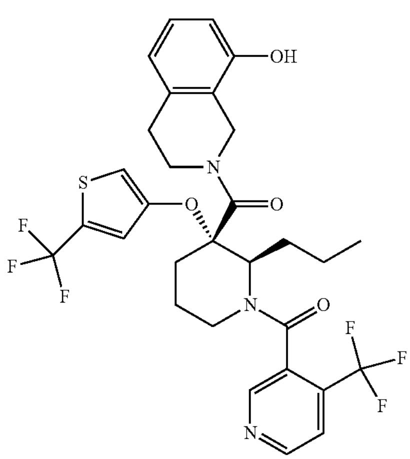 [SMILES: CCC[C@H]1N(C(=O)c2cnccc2C(F)(F)F)CCC[C@@]1(Oc1csc(C(F)(F)F)c1)C(=O)N1CCc2cccc(O)c2C1] | 2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-8-ol | Calc'd 642.2, found 642 | B |

-continued

| Name | Structure | IUPAC Name | Exact Mass [M + H]+ | FP IC50 (um) |
|---|---|---|---|---|
| A122 | 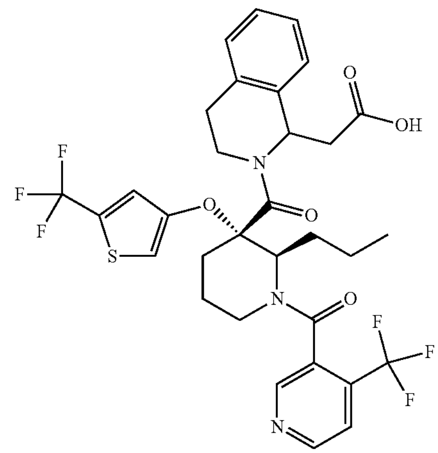 [SMILES: CCC[C@H]1N(C(=O)c2cnccc2C(F)(F)F)CCC[C@@]1(Oc1csc(C(F)(F)F)c1)C(=O)N1CCc2ccccc2C1CC(=O)O] | (2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-1-yl)acetic acid | Calc'd 684.2, found 684 | A |
| A123 | 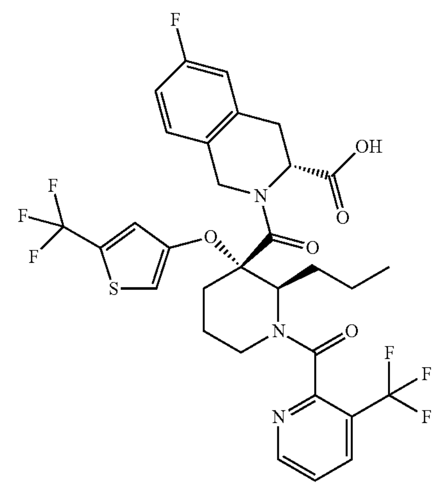 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1C(=O)O] | (3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 688.2, found 688 | A |
| A124 | 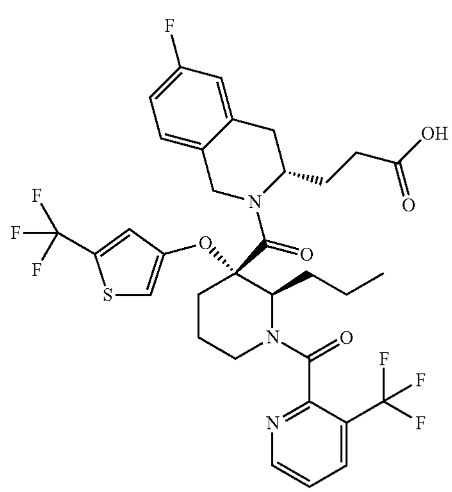 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1CCC(=O)O] | 3-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 716.2, found 716 | A |

| Name | Structure | IUPAC Name | Exact Mass [M + H]+ | FP IC50 (um) |
|------|-----------|------------|---------------------|--------------|
| A125 | 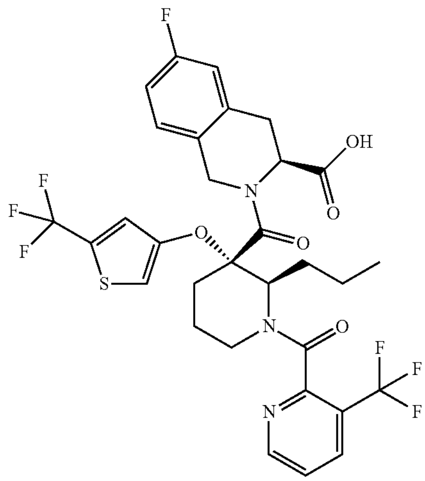 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1C(=O)O] | (3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 688.2, found 688 | A |
| A126 | 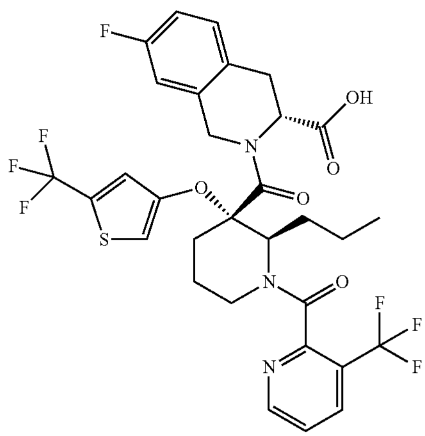 [SMILES: CCC[C@H]1N(C(=O)c2ncccc2C(F)(F)F)CCC[C@@]1(Oc1csc(C(F)(F)F)c1)C(=O)N1Cc2cc(F)ccc2C[C@@H]1C(=O)O] | (3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 688.2, found 688 | A |
| A127 | 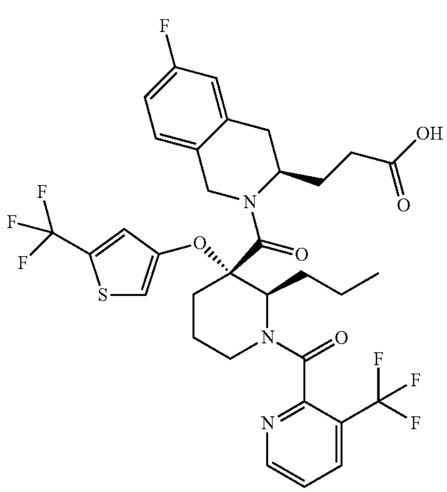 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CCC(=O)O] | 3-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 716.2, found 716 | A |

-continued

| Name | Structure | IUPAC Name | Exact Mass [M + H]+ | FP IC50 (um) |
|------|-----------|------------|---------------------|--------------|
| A128 | 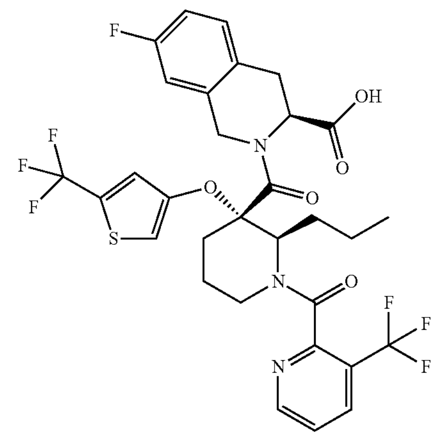 [SMILES: CCC[C@H]1N(C(=O)c2ncccc2C(F)(F)F)CCC[C@@]1(Oc1csc(C(F)(F)F)c1)C(=O)N1Cc2cc(F)ccc2C[C@H]1C(=O)O] | (3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 688.2, found 688 | A |
| A129 | 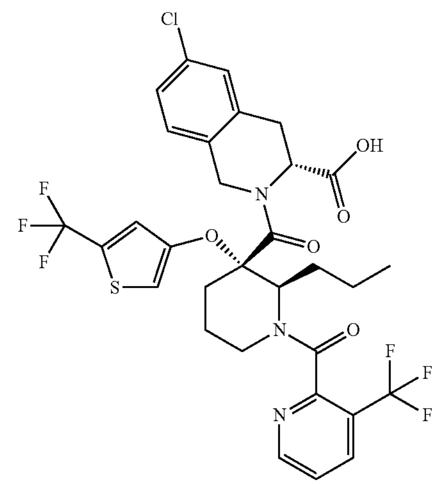 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(=O)O] | (3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 704.1, found 704 | A |
| A130 | 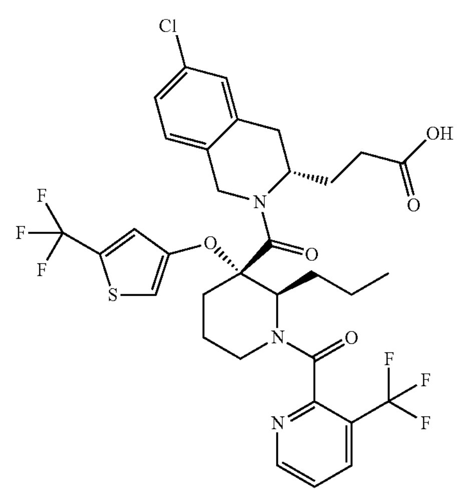 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCC(=O)O] | 3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 732.2, found 732 | A |

-continued

| Name | Structure | IUPAC Name | Exact Mass [M + H]+ | FP IC50 (um) |
|---|---|---|---|---|
| A131 | 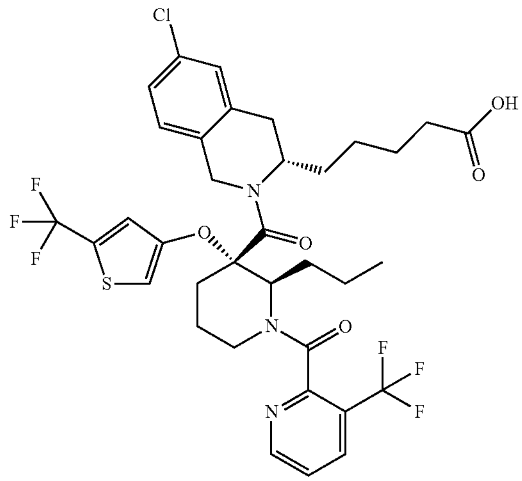 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCCCC(=O)O] | 5-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]pentanoic acid | Calc'd 744.2, found 744 | A |
| A132 | 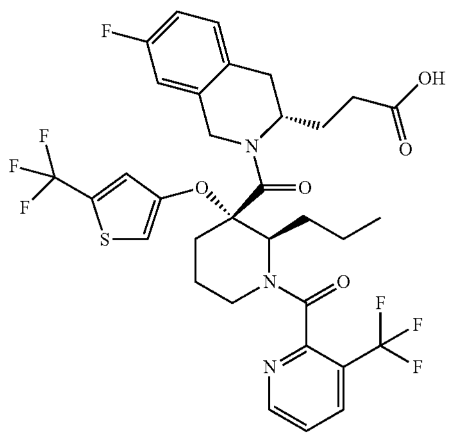 [SMILES: CCC[C@H]1N(C(=O)c2ncccc2C(F)(F)F)CCC[C@@]1(Oc1csc(C(F)(F)F)c1)C(=O)N1Cc2cc(F)ccc2C[C@@H]1CCC(=O)O] | 3-[(3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 716.2, found 716 | A |
| A133 | 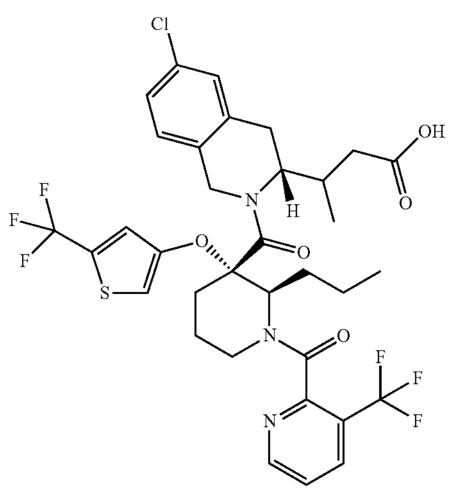 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(C)CC(=O)O] | 3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid | Calc'd 746.2, found 746 | A |

| Name | Structure | IUPAC Name | Exact Mass [M + H]+ | FP IC50 (um) |
|---|---|---|---|---|
| A134 | 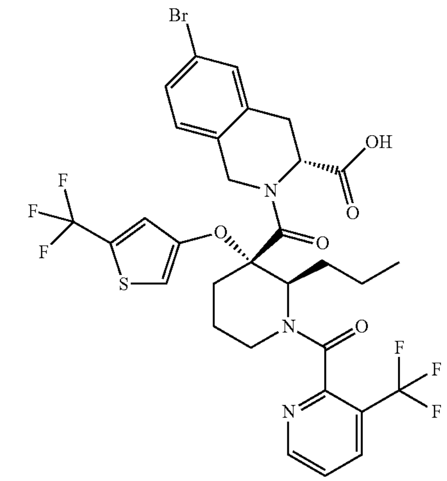 [SMILES: CCC[C@H]1N(C(=O)c2ncccc2C(F)(F)F)CCC[C@@]1(Oc1csc(C(F)(F)F)c1)C(=O)N1Cc2ccc(Br)cc2C[C@@H]1C(=O)O] | (3R)-6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid | Calc'd 748.1, found 748 | A |
| A135 | 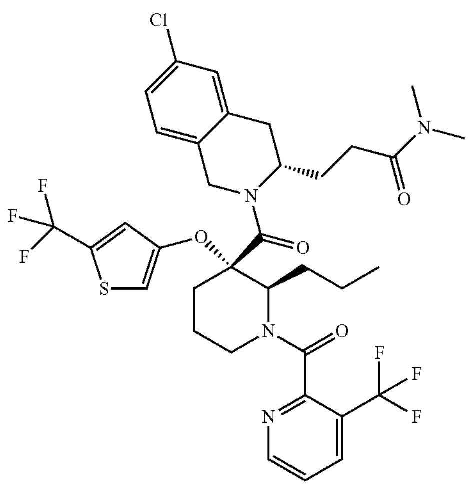 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCC(=O)N(C)C] | 3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N,N-dimethylpropanamide | Calc'd 759.2, found 759 | A |
| A136 | 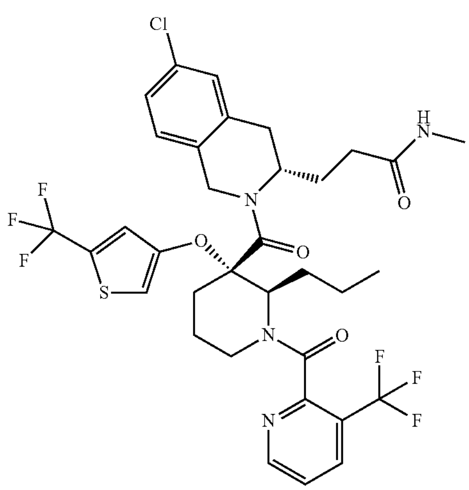 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCC(=O)NC] | 3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-methylpropanamide | Calc'd 745.2, found 745 | A |

-continued

| Name | Structure | IUPAC Name | Exact Mass [M + H]+ | FP IC50 (um) |
|---|---|---|---|---|
| A137 | 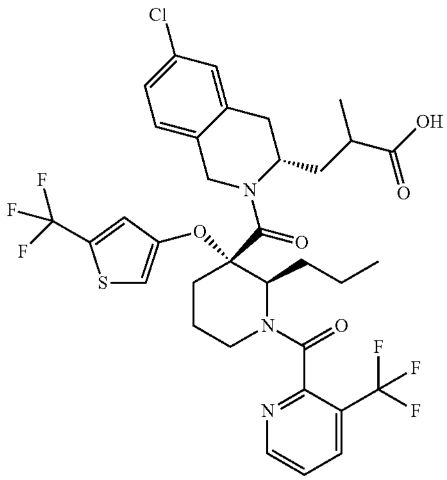 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CC(C)C(=O)O] | (2S)-3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-methylpropanoic acid | Calc'd 746.2, found 746 | A |
| A138 | 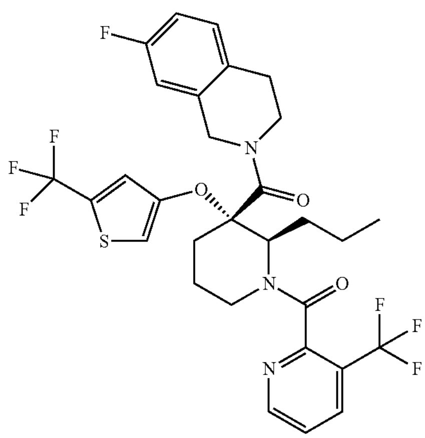 [SMILES: CCC[C@H]1N(C(=O)c2ncccc2C(F)(F)F)CCC[C@@]1(Oc1csc(C(F)(F)F)c1)C(=O)N1CCc2ccc(F)cc2C1] | 7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 644.2, found 644 | B |
| A139 | 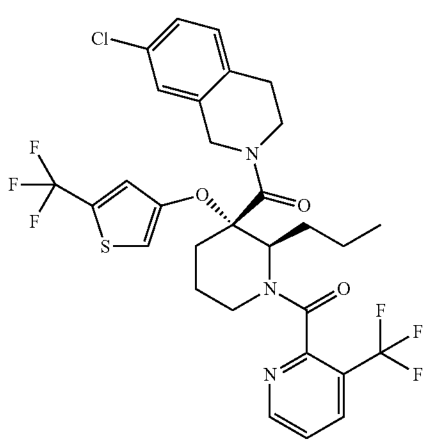 [SMILES: CCC[C@H]1N(C(=O)c2ncccc2C(F)(F)F)CCC[C@@]1(Oc1csc(C(F)(F)F)c1)C(=O)N1CCc2ccc(Cl)cc2C1] | 7-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 660.2, found 660 | B |

-continued

| Name | Structure | IUPAC Name | Exact Mass [M + H]+ | FP IC50 (um) |
|------|-----------|------------|---------------------|--------------|
| A140 | 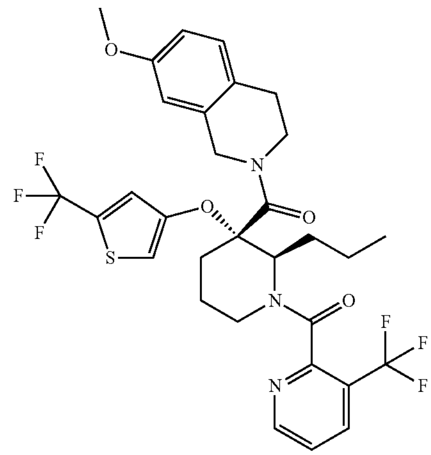 [SMILES: CCC[C@H]1N(C(=O)c2ncccc2C(F)(F)F)CCC[C@@]1(Oc1csc(C(F)(F)F)c1)C(=O)N1CCc2ccc(OC)cc2C1] | 7-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 656.2, found 656 | B |
| A141 | 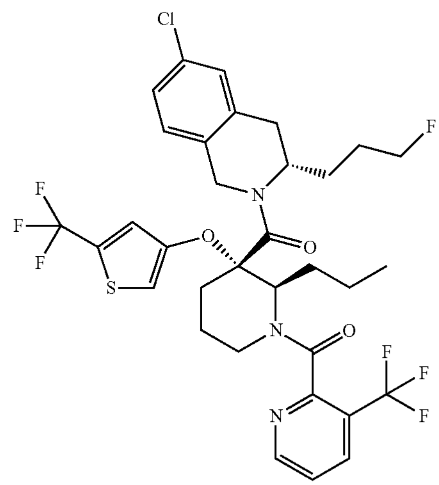 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCCF] | (3S)-6-chloro-3-(3-fluoropropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 720.2, found 720 | B |
| A142 | 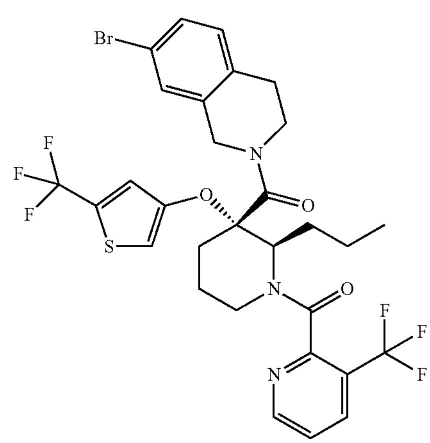 [SMILES: CCC[C@H]1N(C(=O)c2ncccc2C(F)(F)F)CCC[C@@]1(Oc1csc(C(F)(F)F)c1)C(=O)N1CCc2ccc(Br)cc2C1] | 7-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 704.1, found 704 | B |

-continued

| Name | Structure | IUPAC Name | Exact Mass [M + H]+ | FP IC50 (um) |
|------|-----------|------------|---------------------|--------------|
| A143 | 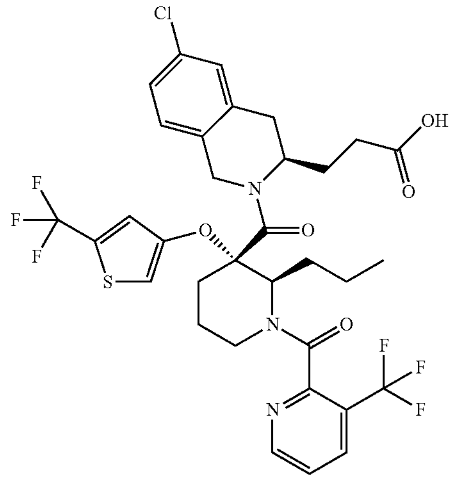 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@H]1CCC(=O)O] | 3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 732.2, found 732 | A |
| A144 | 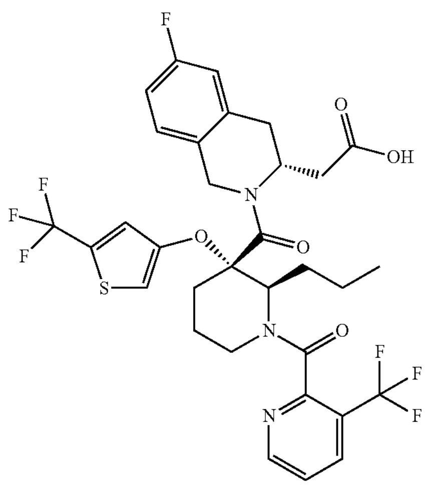 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1CC(=O)O] | [(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]acetic acid | Calc'd 702.2, fouhd 702 | A |
| A145 | 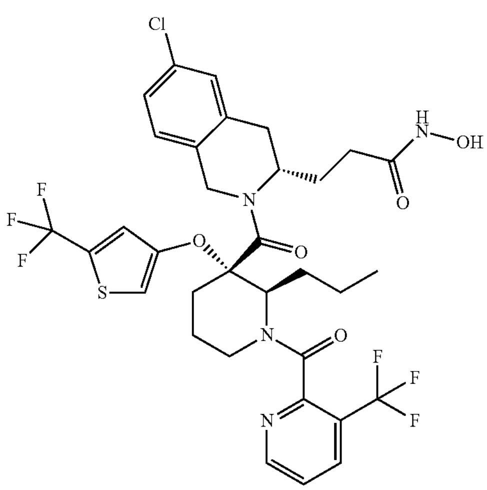 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCC(=O)NO] | 3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-hydroxypropanamide | Calc'd 747.2, found 747 | A |

-continued

| Name | Structure | IUPAC Name | Exact Mass [M + H]+ | FP IC50 (um) |
|---|---|---|---|---|
| A146 | 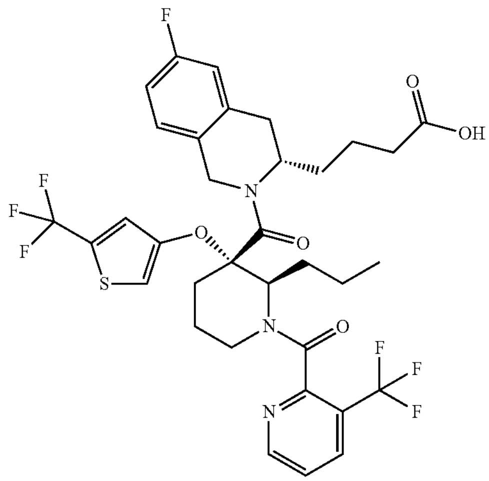 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1CCCC(=O)O] | 4-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid | Calc'd 730.2, found 730 | A |
| A147 | 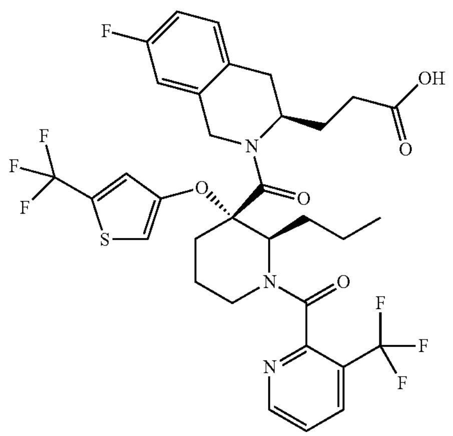 [SMILES: CCC[C@H]1N(C(=O)c2ncccc2C(F)(F)F)CCC[C@@]1(Oc1csc(C(F)(F)F)c1)C(=O)N1Cc2cc(F)ccc2C[C@H]1CCC(=O)O] | 3-[(3R)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 716.2, found 716 | A |
| A148 | 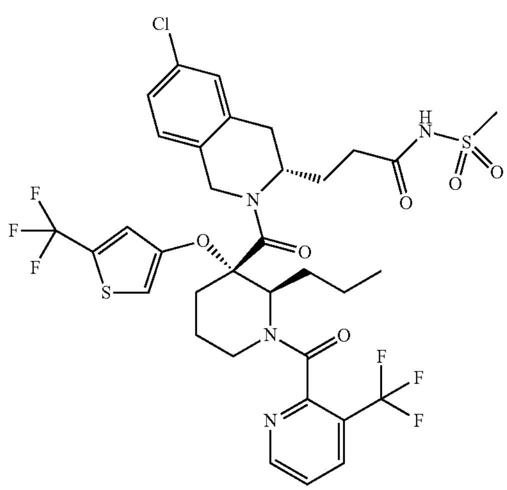 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCC(=O)NS(C)(=O)=O] | 3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-(methylsulfonyl)propanamide | Calc'd 809.2, found 809 | A |

| Name | Structure | IUPAC Name | Exact Mass [M + H]+ | FP IC50 (um) |
|---|---|---|---|---|
| A149 | 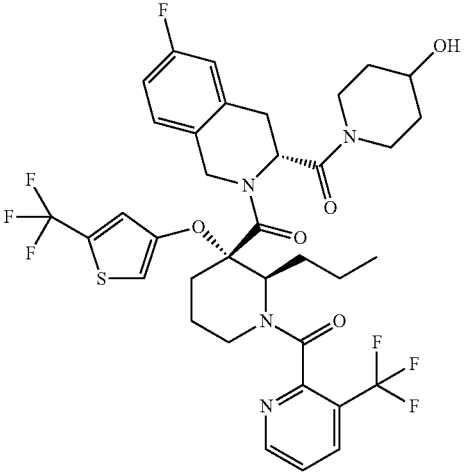 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1C(=O)N1CCC(O)CC1] | 1-{[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-4-ol | Calc'd 771.2, found 771 | A |
| A150 | 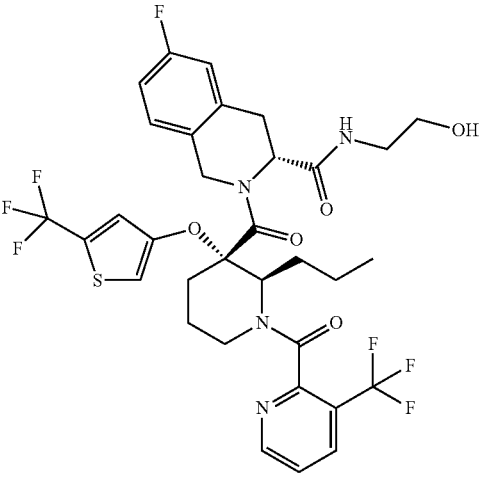 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1C(=O)NCCO] | (3R)-6-fluoro-N-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxamide | Calc'd 731.2, found 731 | A |
| A151 | 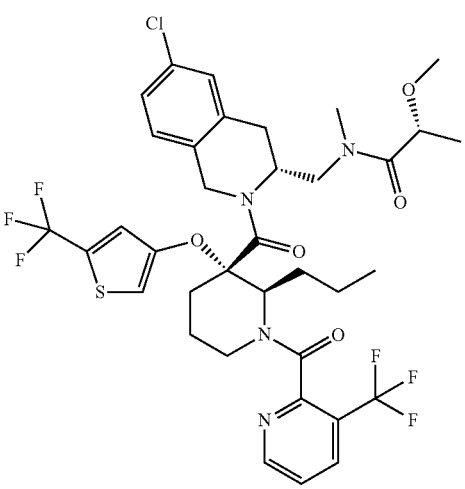 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CN(C)C(=O)[C@@H](C)OC] | (2R)-N-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-2-methoxy-N-methylpropanamide | Calc'd 789.2, found 789 | A |

-continued

| Name | Structure | IUPAC Name | Exact Mass [M + H]+ | FP IC50 (um) |
|---|---|---|---|---|
| A152 | 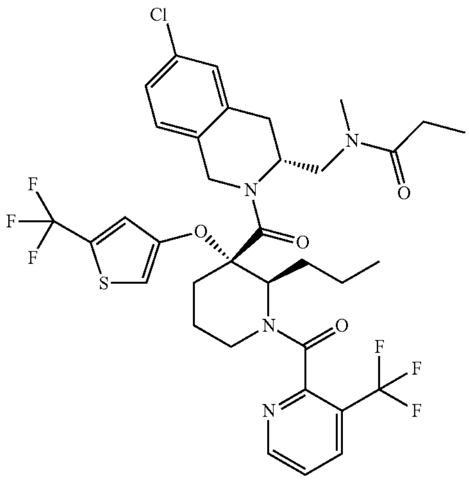 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CN(C)C(=O)CC] | N-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-N-methylpropanamide | Calc'd 759.2, found 759 | A |
| A153 | 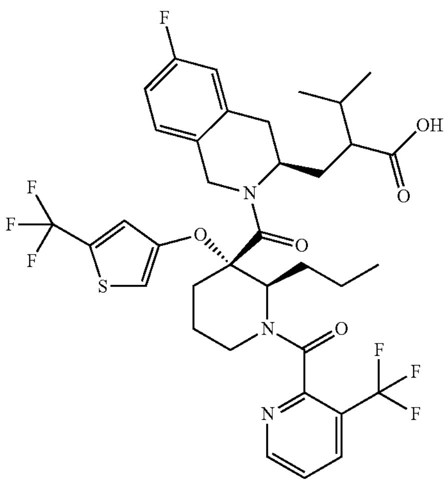 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CC(C(=O)O)C(C)C] | (2S)-2-{[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-3-methylbutanoic acid | Calc'd 758.2, found 758 | A |
| A154 | 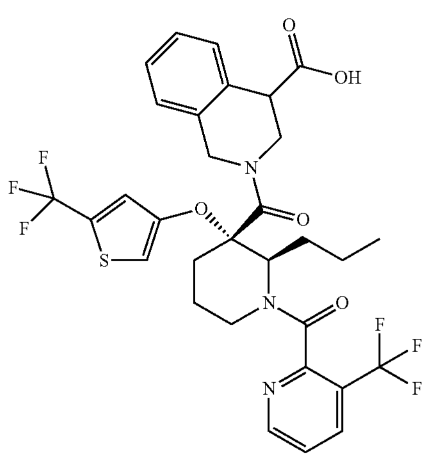 [SMILES: CCC[C@H]1N(C(=O)c2ncccc2C(F)(F)F)CCC[C@@]1(Oc1csc(C(F)(F)F)c1)C(=O)N1Cc2ccccc2C(C(=O)O)C1] | 2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-4-carboxylic acid | Calc'd 670.2, found 670 | B |

-continued

| Name | Structure | IUPAC Name | Exact Mass [M + H]+ | FP IC50 (um) |
|---|---|---|---|---|
| A155 | 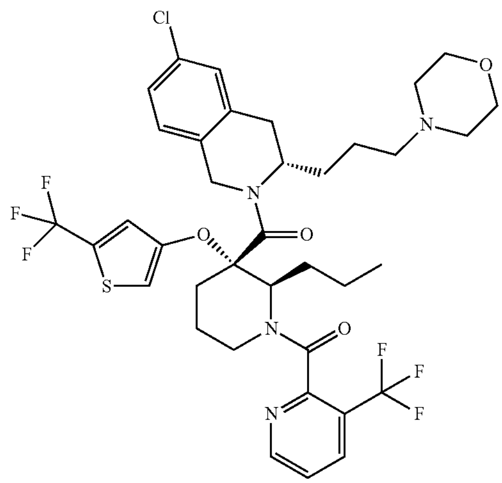 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCCN1CCOCC1] | (3S)-6-chloro-3-(3-morpholin-4-ylpropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 787.3, found 787 | A |
| A156 | 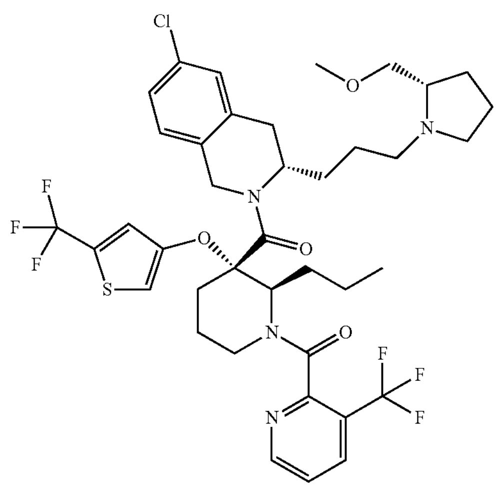 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CCCN1CCC[C@H]1COC] | (3S)-6-chloro-3-{3-[(2S)-2-(methoxymethyl)pyrrolidin-1-yl]propyl}-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 815.3, found 815 | A |
| A157 | 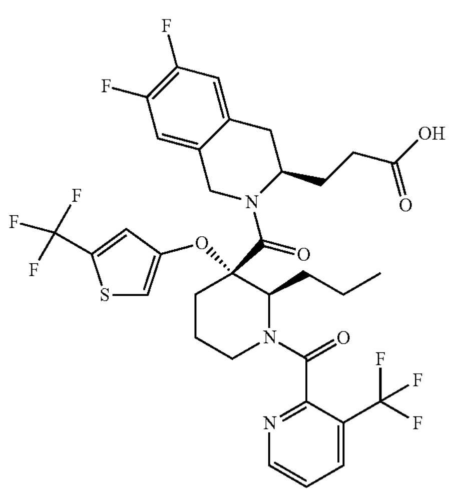 [SMILES: CCC[C@H]1N(C(=O)c2ncccc2C(F)(F)F)CCC[C@@]1(Oc1csc(C(F)(F)F)c1)C(=O)N1Cc2cc(F)c(F)cc2C[C@H]1CCC(=O)O] | 3-[(3R)-6,7-difluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid | Calc'd 734.2, found 734 | A |

-continued

| Name | Structure | IUPAC Name | Exact Mass [M + H]+ | FP IC50 (um) |
|---|---|---|---|---|
| A158 | 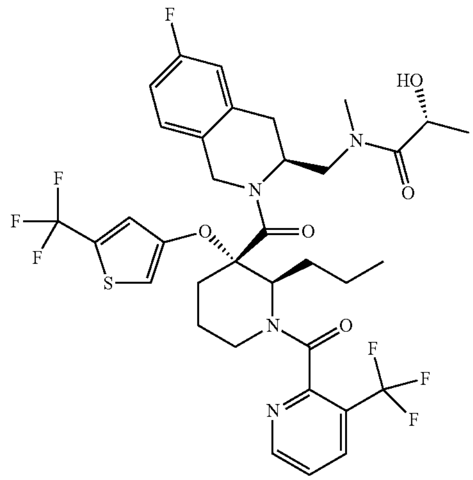 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CN(C)C(=O)[C@@H](C)O] | (2R)-N-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-2-hydroxy-N-methylpropanamide | Calc'd 759.2, found 759 | B |
| A159 | 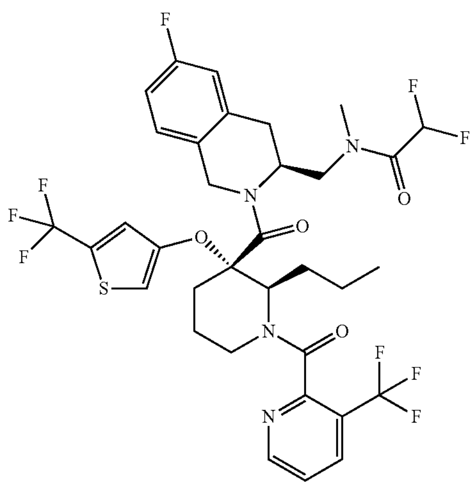 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CN(C)C(=O)C(F)F] | 2,2-difluoro-N-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-N-methylacetamide | Calc'd 765.2, found 765 | B |
| A160 | 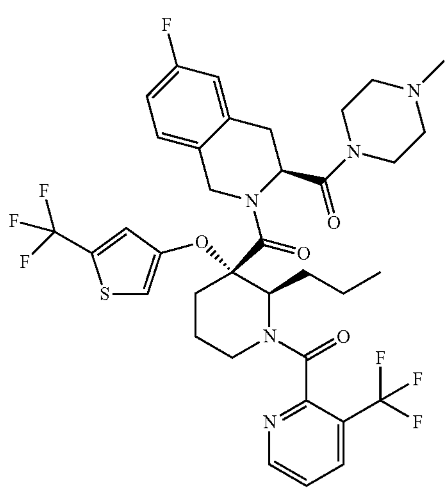 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1C(=O)N1CCN(C)CC1] | (3S)-6-fluoro-3-[(4-methylpiperazin-1-yl)carbonyl]-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 770.3, found 770 | B |

-continued

| Name | Structure | IUPAC Name | Exact Mass [M + H]+ | FP IC50 (um) |
|---|---|---|---|---|
| A161 | 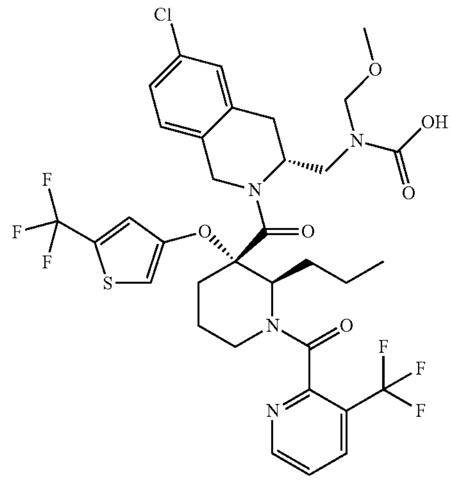 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CN(COC)C(=O)O] | (2R)-3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-(methoxymethyl)propanoic acid | Calc'd 776.2, found 776 | A |
| A162 | 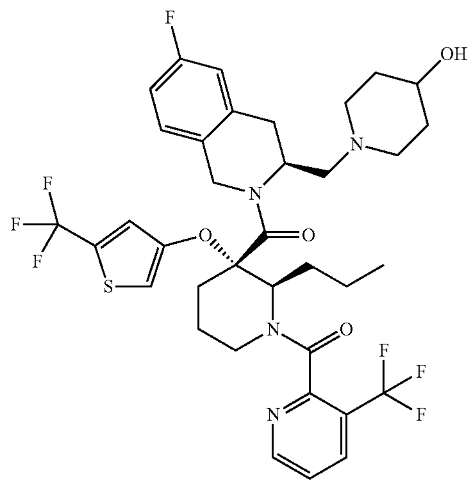 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CN1CCC(O)CC1] | 1-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}piperidin-4-ol | Calc'd 757.3, found 757 | B |
| A163 | 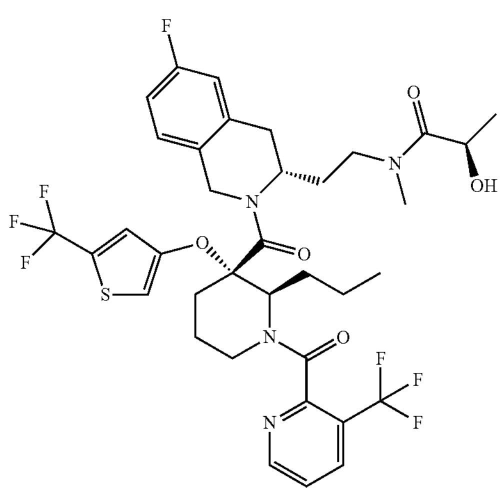 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@@H]1CCN(C)C(=O)[C@@H](C)O] | (2R)-N-{2-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]ethyl}-2-hydroxy-N-methylpropanamide | Calc'd 773.3, found 773 | A |

-continued

| Name | Structure | IUPAC Name | Exact Mass [M + H]+ | FP IC50 (um) |
|---|---|---|---|---|
| A164 | 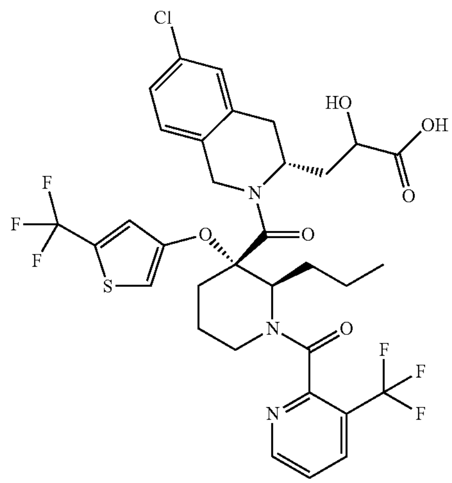 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CC(O)C(=O)O] | (2S)-3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-hydroxypropanoic acid | Calc'd 748.2, found 748 | A |
| A165 | 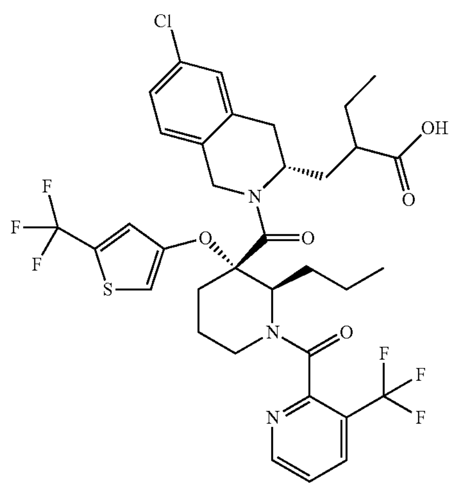 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1CC(CC)C(=O)O] | (2S)-2-{[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}butanoic acid | Calc'd 760.2, found 760 | A |
| A166 | 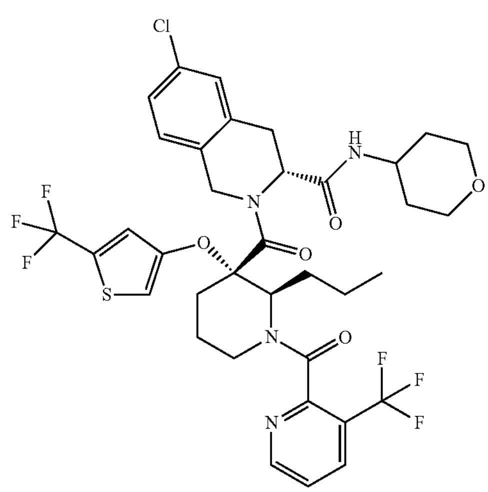 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(=O)NC1CCOCC1] | (3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-N-(tetrahydro-2H-pyran-4-yl)-1,2,3,4-tetrahydroisoquinoline-3-carboxamide | Calc'd 787.2, found 787 | A |

| Name | Structure | IUPAC Name | Exact Mass [M + H]+ | FP IC50 (um) |
|---|---|---|---|---|
| A167 | 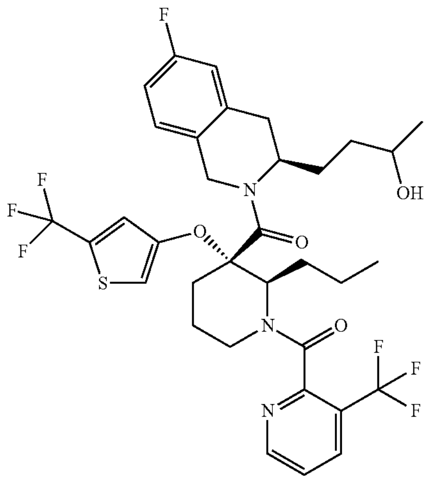 [SMILES: CCC[C@H]1N(C(=O)c2ncccc2C(F)(F)F)CCC[C@@]1(Oc1csc(C(F)(F)F)c1)C(=O)N1Cc2ccc(F)cc2C[C@H]1CCC(C)O] | 4-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butan-2-ol | Calc'd 716.2, found 716 | A |
| A168 | 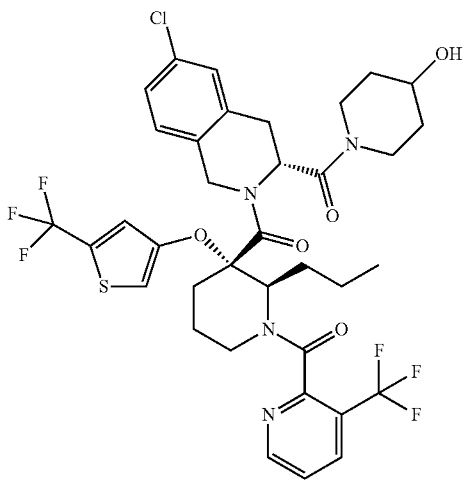 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(=O)N1CCC(O)CC1] | 1-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-4-ol | Calc'd 787.2, found 787 | A |
| A169 | 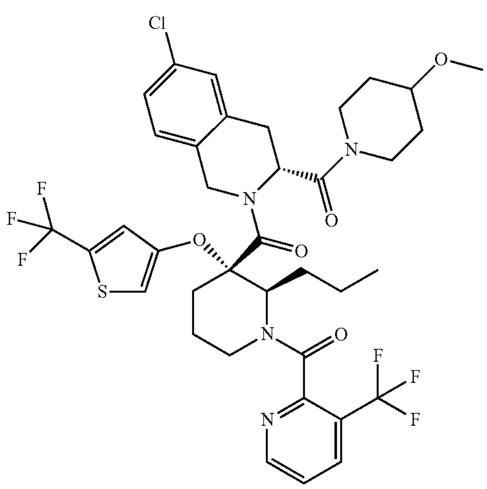 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(=O)N1CCC(OC)CC1] | (3R)-6-chloro-3-[(4-methoxypiperidin-1-yl)carbonyl]-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 801.2, found 801 | A |

-continued

| Name | Structure | IUPAC Name | Exact Mass [M + H]+ | FP IC50 (um) |
|---|---|---|---|---|
| A170 | 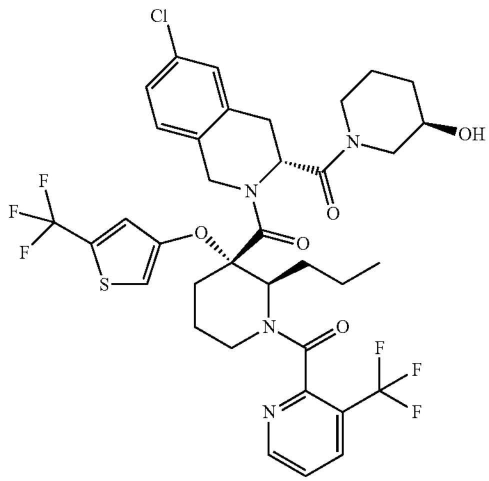 [SMILES: CCC[C@H]1N(C(=O)c2ncccc2C(F)(F)F)CCC[C@@]1(Oc1csc(C(F)(F)F)c1)C(=O)N1Cc2ccc(Cl)cc2C[C@@H]1C(=O)N1CCC[C@@H](O)C1] | (3R)-1-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-3-ol | Calc'd 787.2, found 787 | A |
| A171 | 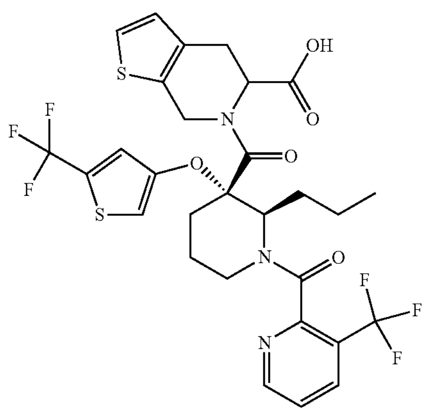 [SMILES: CCC[C@H]1N(C(=O)c2ncccc2C(F)(F)F)CCC[C@@]1(Oc1csc(C(F)(F)F)c1)C(=O)N1Cc2sccc2CC1C(=O)O] | 6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-5-carboxylic acid | Calc'd 676.1, found 676 | B |
| A172 | 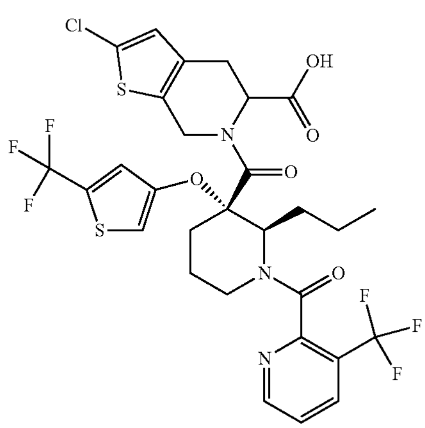 [SMILES: CCC[C@H]1N(C(=O)c2ncccc2C(F)(F)F)CCC[C@@]1(Oc1csc(C(F)(F)F)c1)C(=O)N1Cc2sc(Cl)cc2CC1C(=O)O] | 2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-5-carboxylic acid | Calc'd 710.1, found 710 | A |

-continued

| Name | Structure | IUPAC Name | Exact Mass [M + H]+ | FP IC50 (um) |
|---|---|---|---|---|
| A173 | 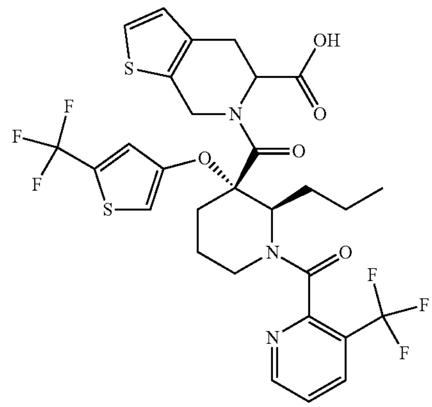 [SMILES: CCC[C@H]1N(C(=O)c2ncccc2C(F)(F)F)CCC[C@@]1(Oc1csc(C(F)(F)F)c1)C(=O)N1Cc2sccc2CC1C(=O)O] | 6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-5-carboxylic acid | Calc'd 676.1, found 676 | B |
| A174 | 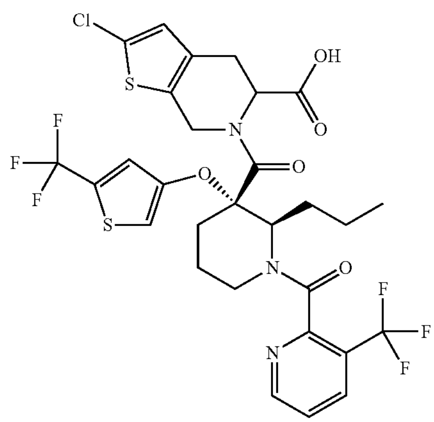 [SMILES: CCC[C@H]1N(C(=O)c2ncccc2C(F)(F)F)CCC[C@@]1(Oc1csc(C(F)(F)F)c1)C(=O)N1Cc2sc(Cl)cc2CC1C(=O)O] | 2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-5-carboxylic acid | Calc'd 710.1, found 710 | A |
| A175 | 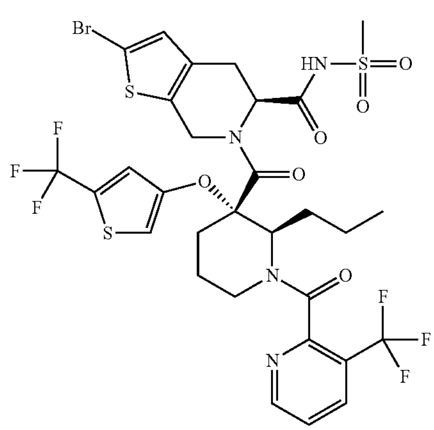 [SMILES: CCC[C@H]1N(C(=O)c2ncccc2C(F)(F)F)CCC[C@@]1(Oc1csc(C(F)(F)F)c1)C(=O)N1Cc2sc(Br)cc2C[C@H]1C(=O)NS(C)(=O)=O] | (5S)-2-bromo-N-(methylsulfonyl)-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-5-carboxamide | Calc'd 831.0, found 630.8 | A |

-continued

| Name | Structure | IUPAC Name | Exact Mass [M + H]+ | FP IC50 (um) |
|---|---|---|---|---|
| A176 | 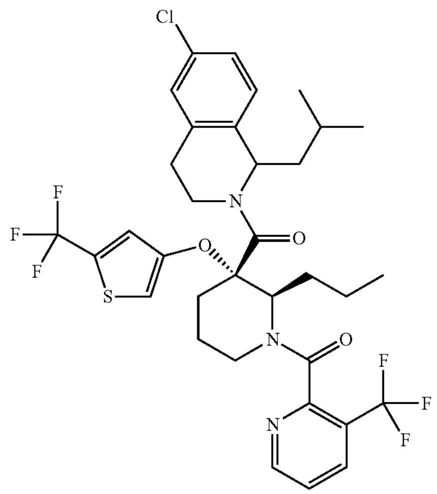 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C)C] | 6-chloro-1-(2-methylpropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline | Calc'd 716.2, found 716.2 | B |
| A177 | 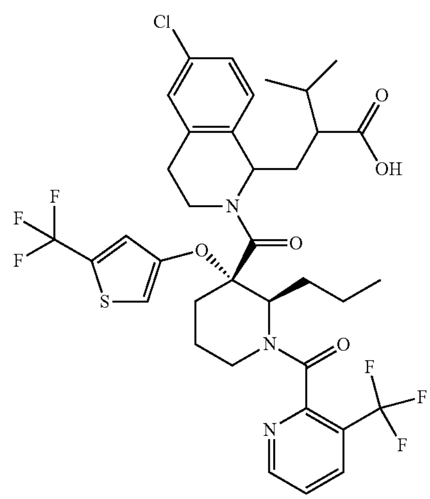 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C(=O)O)C(C)C] | 2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid | Calc'd 774.2, found 744.1 | B |
| A178 | 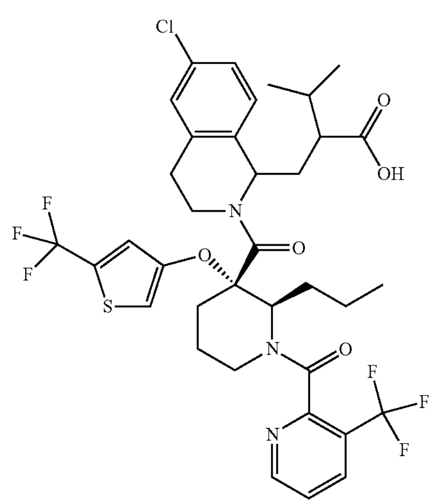 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C(=O)O)C(C)C] | 2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid | Calc'd 774.2, found 744.1 | A |

| Name | Structure | IUPAC Name | Exact Mass [M + H]+ | FP IC50 (um) |
|---|---|---|---|---|
| A179 | 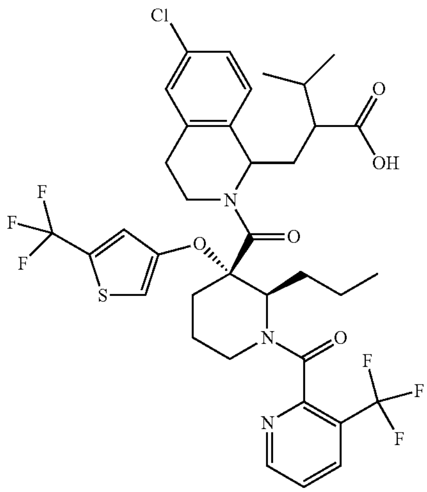 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C(=O)O)C(C)C] | 2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid | Calc'd 774.2, found 744.1 | A |
| A180 | 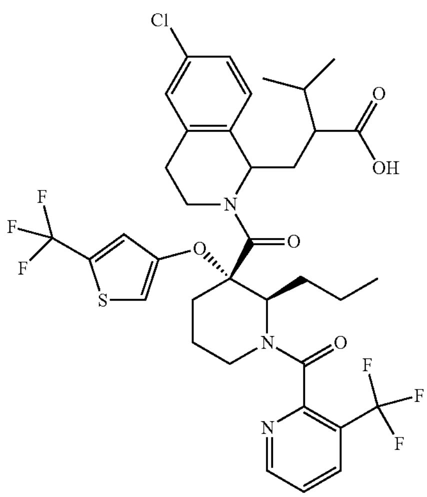 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1CC(C(=O)O)C(C)C] | 2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid | Calc'd 774.2, found 744.1 | B |
| A181 | 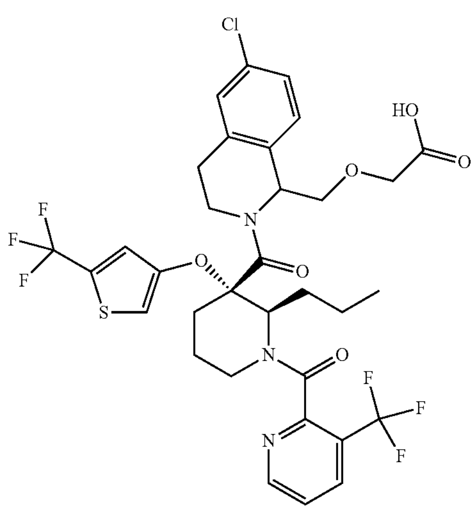 [SMILES: CCC[C@H]1N(C(=O)c2ncccc2C(F)(F)F)CCC[C@@]1(Oc1csc(C(F)(F)F)c1)C(=O)N1CCc2cc(Cl)ccc2C1COCC(=O)O] | [(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methoxy]acetic acid | Calc'd 748.2, found 747.8 | A |

A indicates IC$_{50}$ of 1-100 nM, B indicates IC$_{50}$ of 101 nM-20 uM.

Example 2

HDM2 Activity

The compounds were evaluated to determine activity at the HDM2 protein by known methods such as the fluorescence polarization screening assay that measures the inhibitory concentration that achieves 50% of maximal activity (FP $IC_{50}$) and the dissociation constant for inhibitor binding (FP Ki). [Zhang et al., J. Analytical Biochemistry 331: 138-146 (2004)].

Additionally, compounds can be tested for activity at the HDM2 protein using the Cell Viability Assay, which measures the number of viable cells in culture after treatment with the inventive compound for a certain period of time e.g. 72 hours based on quantitation of the ATP present (Cell Viability. $IC_{50}$). [CellTiter-Glo® Luminescent Cell Viability Assay from Promega].

Example 3

CYP Inhibition

In order to assess the potential for inhibition of CYP3A4, human liver microsomes were incubated with several concentrations of the compounds of the invention (0 to 30 mM), 1 mM reduced nicotinamide adenine dinucleotide phosphate (NADPH) and probe substrate testosterone (100 mM) at 37° C. for 13 min. The CYP3A4 activity was measured by the formation of the specific metabolite, 6b-hydroxy-testosterone. The concentrations of the metabolite formed after incubation were determined by LC-MS/MS using a standard curve. The concentrations at which 50% of the initial enzyme activity was inhibited (IC50) were determined from the graph of compound concentrations versus percent of inhibition.

Alternatively, human liver microsomes were incubated with several concentrations of compounds of the invention (0 to 20 mM), 1 mM reduced nicotinamide adenine dinucleotide phosphate (NADPH) and probe substrate midazolam (5 mM) at 37° C. for 10 min. The CYP3A4 activity Was measured by the formation of the specific metabolite, 1-hydroxy-midazolam. The concentrations of the metabolite formed after incubation were determined by LC-MS/MS using a standard curve. The concentrations at which 50% of the initial enzyme activity was inhibited (IC50) were determined from the graph of compound concentrations versus percent of inhibition.

To evaluate time-dependent inhibition, compounds at the stated concentrations were pre-incubated with human liver microsomes for 30 min at 37° C. in the presence of NADPH and in the absence of substrates. After the pre-incubation step, the CYP substrates were added at the previously stated concentrations and the reactions were allowed to proceed as indicated in the previous paragraph.

What is claimed is:
1. A compound of Formula I:

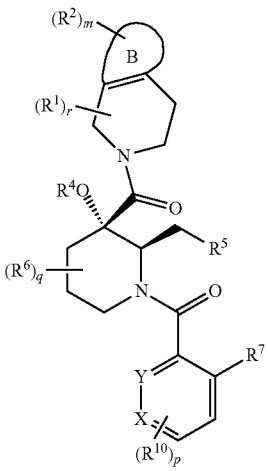

wherein:
X is $CR^3$ or N;
Y is $CR^3$ or N;
Ring B is a 5 or 6-membered heteroaryl ring or phenyl;
$R^1$ is independently selected from H, halo, CN, $(CR^a_2)_nR^8$, $-N(R^8)_2$, $(C_3-C_6)$cycloalkyl$COOR^8$, $(CR^a_2)_nCOOR^8$, $(CR^a_2)_nC(O)NR^aR^8$, $(CR^a_2)_nC(O)NR^aSO_2R^8$, $(CR^a_2)_nNR^aC(O)R^8$, $(CR^a_2)_nOR^8$, $(CR^a_2)_nC(O)R^8$ and $(CR^a_2)_nO(CR^a_2)_nCOOR^a$;
$R^2$ is independently selected from H, halo, CN, amide, aryl, heterocyclic, $(CR^a_2)_nCOOR^8$, $-N(R^a)_2$, $(CR^a_2)_nOR^a$, $(CR^a_2)_nSR^a$ and $-SO_2R^a$, wherein the aryl or heterocyclic is optionally substituted with one to three substituents selected from cyano, hydroxy, amide, halo and methoxy;
Provided that $R^1$ and $R^2$ are not both H;
$R^3$ is independently selected from the group consisting of: H, cyano, hydroxy, and alkoxy;
$R^4$ is heteroaryl which is optionally substituted with halo, halo-$(C_1-C_6)$alkyl, $(C_1-C_6)$alkyl, or $-(C_1-C_6)$alkoxy;
$R^5$ is H, $(C_1-C_6)$alkyl, $(C_1-C_6)$alkenyl, $(C_1-C_6)$alkynyl, $(CR^b_2)_tCOOH$, $(CR^b_2)_tN(R^9)_2$, $(CR^b_2)_tOR^9$ or $(CR^b_2)_tR^9$;
$R^6$ is independently $(C_1-C_6)$alkyl;
$R^7$ is haloalkyl, $-NR^aC(O)R^a$, or $C(O)N(R^a)_2$;
$R^8$ is independently selected from H, halo, OH, CN, $(C_1-C_6)$alkyl, $(C_3-C_8)$cycloalkyl, heterocylic, heterocyclenyl, heteroaryl, $(C_1-C_6)$alkylheterocyclic, $(C_1-C_6)$alkylheterocyclenyl and (C1-C6)alkylheteroaryl, wherein said alkyl, cycloalkyl, heterocyclic, heterocyclenyl and heteroaryl is optionally substituted with $(C_1-C_6)$alkyl, $(CR^a_2)_nOR^a$, $-N(R^a)_2$, $(CR^a_2)_nCOOR^a$, $(CR^a_2)_nC(O)NR^aR^a$, or $(CR^a_2)_nNR^aC(O)R^a$;
$R^9$ is independently H, $(C_1-C_6)$alkyl, $(C_3-C_8)$cycloalkyl, heteroaryl, heterocyclenyl or heterocyclic, wherein the alkyl, cycloalkyl, heteroaryl, heterocyclenyl and heterocyclic is optionally substituted with $(C_1-C_6)$alkyl, $(C_3-C_8)$cycloalkyl, $(CR^a{}_2)_n$COOH, or $(CR^a{}_2)_n$OR$^b$;

$R^{10}$ is independently $(C_1-C_6)$alkyl;

$R^a$ is independently H or $(C_1-C_6)$alkyl, wherein the alkyl is optionally substituted with $(C_0-C_6)$alkyl-OH or —$(C_0-C_6)$alkylOMe; and $R^b$ is independently H or $(C_1-C_6)$alkyl;

m is 1, 2, or 3;

n is independently 0, 1, 2, 3, 4 or 5;

p is 0, 1, or 2;

q is 0,1,2, or 3;

r is 1,2 or 3;

t is 0,1,2 or 3;

or a pharmaceutically acceptable salt thereof.

2. The compound of claim 1, wherein

X is $CR^3$ or N;

Y is $CR^3$ or N;

Ring B is a 5 or 6-membered heteroaryl ring or phenyl;

$R^1$ is independently selected from halo, CN, $(CR^a{}_2)_nR^8$, —$N(R^8)_2$, $(C_3-C_6)$cycloalkylCOOR$^8$, $(CR^a{}_2)_n$COOR$^8$, $(CR^a{}_2)_n$C(O)NR$^a$R$^8$, $(CR^a{}_2)_n$C(O)NR$^a$SO$_2$R$^8$, $(CR^a{}_2)_n$NR$^a$C(O)R$^8$, $(CR^a{}_2)_n$OR$^8$, $(CR^a{}_2)_n$C(O)R$^8$ and $(CR^a{}_2)_n$O(CR$^a{}_2)_n$COOR$^a$;

$R^2$ is independently selected from H, halo, CN, amide, aryl, heterocyclic, $(CR^a{}_2)_n$COOR$^8$, —$N(R^a)_2$, $(CR^a{}_2)_n$OR$^a$, $(CR^a{}_2)_n$SR$^a$ and —SO$_2$R$^a$, wherein the aryl or heterocyclic is optionally substituted with one to three substituents selected from cyano, hydroxy, amide, halo and methoxy;

$R^3$ is independently selected from the group consisting of: H, cyano, hydroxy, and alkoxy;

$R^4$ is heteroaryl which is optionally substituted with halo, halo-$(C_1-C_6)$alkyl, $(C_1-C_6)$alkyl, or —$(C_1-C_6)$alkoxy;

$R^5$ is H, $(C_1-C_6)$alkyl, $(C_1-C_6)$alkenyl, $(C_1-C_6)$alkynyl, $(CR^b{}_2)_t$COOH, $(CR^b{}_2)_t$N(R$^9$)$_2$, $(CR^b{}_2)_t$OR$^9$ or $(CR^b{}_2)_t$R$^9$;

$R^6$ is independently $(C_1-C_6)$alkyl;

$R^7$ is haloalkyl, —NR$^a$C(O)R$^a$, or C(O)N(R$^a$)$_2$;

$R^8$ is independently selected from H, halo, OH, CN, $(C_1-C_6)$alkyl, $(C_3-C_8)$cycloalkyl, heterocylic, heterocyclenyl, heteroaryl, $(C_1-C_6)$alkylheterocyclic, $(C_1-C_6)$alkylheterocyclenyl and $(C_1-C_6)$alkylheteroaryl, wherein said alkyl, cycloalkyl, heterocyclic, heterocyclenyl and heteroaryl is optionally substituted with $(C_1-C_6)$alkyl, $(CR^a{}_2)_n$OR$^a$, —N(R$^a$)$_2$, $(CR^a{}_2)_n$COOR$^a$, $(CR^a{}_2)_n$C(O)NR$^a$R$^a$, or $(CR^a{}_2)_n$NR$^a$C(O)R$^a$;

$R^9$ is independently H, $(C_1-C_6)$alkyl, $(C_3-C_8)$cycloalkyl, heteroaryl, heterocyclenyl or heterocyclic, wherein the alkyl, cycloalkyl, heteroaryl, heterocyclenyl and heterocyclic is optionally substituted with $(C_1-C_6)$alkyl, $(C_3-C_8)$cycloalkyl, $(CR^a{}_2)_n$COOH, or $(CR^a{}_2)_n$OR$^b$;

$R^{10}$ is independently $(C_1-C_6)$alkyl;

$R^a$ is independently H or $(C_1-C_6)$alkyl, wherein the alkyl is optionally substituted with $(C_0-C_6)$alkyl-OH or —$(C_0-C_6)$alkylOMe; and $R^b$ is independently H or $(C_1-C_6)$alkyl;

m is 1, 2, or 3;

n is independently 0, 1, 2, 3, 4 or 5;

p is 0,1, or 2;

q is 0,1,2, or 3;

r is 1,2 or 3;

t is 0,1,2 or 3.

3. The compound of claim 1, wherein $R^4$ is thienyl, optionally substituted with CF$_3$, CBr$_3$, CCl$_3$, CH$_3$, Br, Cl, F, or —OCH$_3$.

4. The compound of claim 1, wherein $R^4$ is

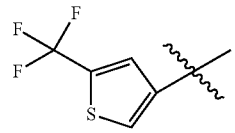

5. The compound of claim 1 under Formula II,

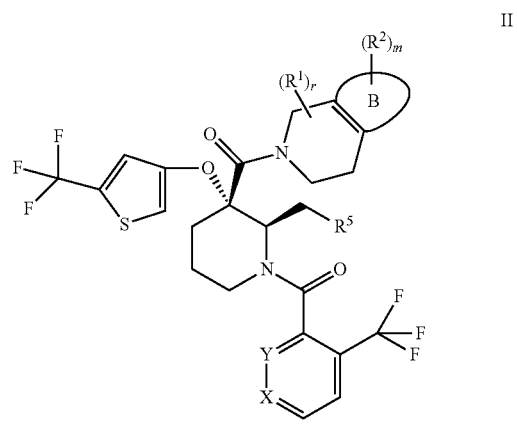

II wherein:

X is CH and Y is N, or X is N and Y is CH;

Ring B is a 5 or 6-membered heteroaryl ring or phenyl;

$R^1$ is independently selected from H, halo, CN, $(CR^a{}_2)_nR^8$, —$N(R^8)_2$, $C_3-C_6$cycloalkylCOOR$^8$, $(CR^a{}_2)_n$COOR$^8$, $(CR^a{}_2)_n$C(O)NR$^a$R$^8$, $(CR^a{}_2)_n$C(O)NR$^a$SO$_2$R$^8$, $(CR^a{}_2)_n$NR$^a$C(O)R$^8$, $(CR^a{}_2)_n$OR$^8$, $(CR^a{}_2)_n$C(O)R$^8$ and $(CR^a{}_2)_n$O(CR$^a{}_2)_n$COOR$^a$;

$R^2$ is independently selected from H, halo, CN, amide, aryl, heterocyclic, $(CR^a{}_2)_n$COOR$^8$, —$N(R^a)_2$, $(CR^a{}_2)_n$OR$^a$, $(CR^a{}_2)_n$SR$^a$ and —SO$_2$R$^a$, wherein the aryl or heterocyclic is optionally substituted with one to three substituents selected from cyano, hydroxy, amide, halo and methoxy;

Provided that $R^1$ and $R^2$ are not both H;

$R^5$ is H, $(C_1-C_6)$alkyl, $(C_1-C_6)$alkenyl, $(C_1-C_6)$alkynyl, $(CR^b{}_2)_t$COOH, $(CR^b{}_2)_t$N(R$^9$)$_2$, $(CR^b{}_2)_t$OR$^9$ or $(CR^b{}_2)_t$R$^9$;

$R^8$ is independently selected from H, halo, OH, CN, $(C_1-C_6)$alkyl, $(C_3-C_8)$cycloalkyl, heterocylic, heterocyclenyl, heteroaryl, $(C_1-C_6)$alkylheterocyclic, $(C_1-C_6)$alkylheterocyclenyl and (C1-C6)alkylheteroaryl, wherein said alkyl, cycloalkyl, heterocyclic, heterocyclenyl and heteroaryl is optionally substituted with $(C_1-C_6)$alkyl, $(CR^a{}_2)_n$OR$^a$, —N(R$^a$)$_2$, $(CR^a{}_2)_n$COOR$^a$, $(CR^a{}_2)_n$C(O)NR$^a$R$^a$, or $(CR^a{}_2)_n$NR$^a$C(O)R$^a$;

$R^9$ is independently H, $(C_1-C_6)$alkyl, $(C_3-C_8)$cycloalkyl, heteroaryl, heterocyclenyl or heterocyclic, wherein the alkyl, cycloalkyl, heteroaryl, heterocyclenyl and heterocyclic is optionally substituted with $(C_1-C_6)$alkyl, $(C_3-C_8)$cycloalkyl, $(CR^a{}_2)_n$COOH, or $(CR^a{}_2)_n$OR$^b$;

$R^a$ is independently H or $(C_1-C_6)$alkyl, wherein the alkyl is optionally substituted with $(C_0-C_6)$alkyl-OH or $(C_0-C_6)$alkylOMe; and $R^b$ is independently H or $(C_1-C_6)$alkyl;

m is 1 or 2;

n is independently 0, 1, 2, 3 or 4;

r is 1 or 2;

t is 0, 1 or 2.

6. The compound of claim 5 under Formula III:

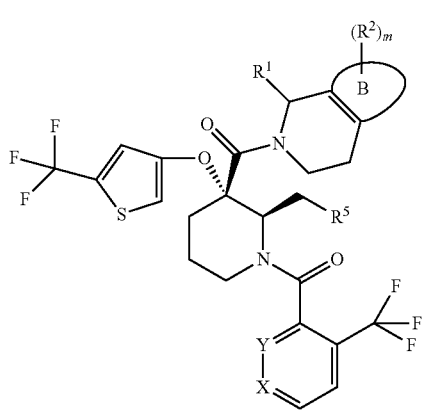

wherein
R¹ is selected from (C₃-C₆)cycloalkylCOOR$^a$, (CR$^a_2$)$_n$COOR$^a$, (CR$^a_2$)$_n$O(CR$^a_2$)$_n$COOR$^a$, and (CR$^a_2$)$_n$C(O)NR$^a$SO₂R⁸;
and all other substituents are as defined in claim 5.

7. The compound of claim 5 under Formula III:

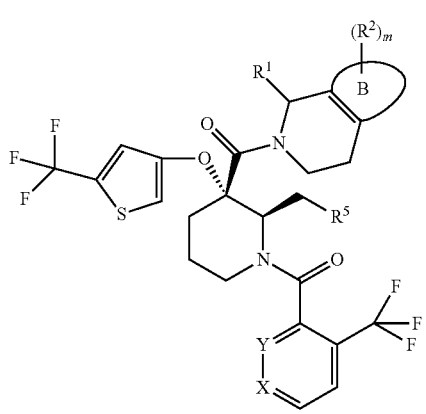

wherein
R¹ is -cyclopentyl-COOH, (CR$^a_2$)$_n$COOH, (CR$^a_2$)$_n$O(CR$^a_2$)$_n$COOH, (CR$^a_2$)$_n$C(O)NR$^a$SO₂R$^a$, methoxymethyl, morpholinylmethyl, or C(O)NH₂, wherein n is 0, 1, 2, 3 or 4, and all other substituents are as defined in claim 5.

8. The compound of claim 1, wherein R¹ is (CR$^a_2$)$_n$COOR$^a$.

9. The compound of claim 7, wherein R¹ is (CH₂)$_n$COOH, and n is 2 or 3.

10. The compound of claim 1, wherein R² is halo.

11. The compound of claim 10, wherein R² is Cl or Br.

12. The compound of claim 5 under Formula VA:

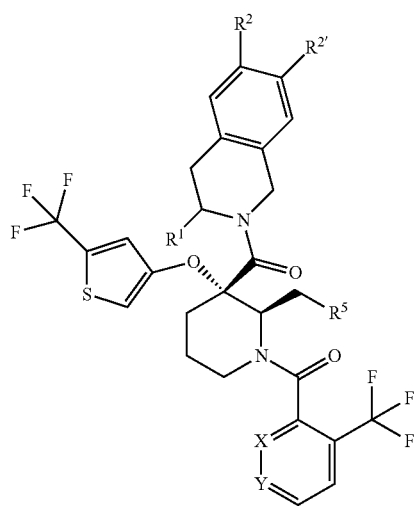

Wherein
R¹ is selected from (C₃-C₆)cycloalkylCOOR$^a$, (CR$^a_2$)$_n$COOR$^a$, (CR$^a_2$)$_n$O(CR$^a_2$)$_n$COOR$^a$, and (CR$^a_2$)$_n$C(O)NR$^a$SO₂R⁸;
R² and R²'are independently H, Br or Cl;
and all other substituents are as defined in claim 5.

13. The compound of claim 1, wherein R⁵ is methyl, CH(CH₃)COOH, CH₂CH₂COOH or heterocyclic, said heterocyclic optionally substituted with (C₁-C₃)alkyl, (C₃-C₅)cycloalkyl, (CR$^a_2$)$_n$COOH, or (CR$^a_2$)$_n$OR$^b$.

14. The compound of claim 1 selected from the group consisting of:
2-[(2R,3S)-3-[(7-chloro-3,4-dihydroisoquinolin-2(1H)-yl)carbonyl]-1-{[4-(trifluoromethyl)pyridin-3-yl]carbonyl}-3-{[5-(trifluoromethyl)thiophen-3-yl]oxy}piperidin-2-yl]-N,N-bis(2-methoxyethyl)ethanamine;
2-[(2R,3S)-3-[(6-chloro-3,4-dihydroisoquinolin-2(1H)-yl)carbonyl]-1-{[4-(trifluoromethyl)pyridin-3-yl]carbonyl}-3-{[5-(trifluoromethyl)thiophen-3-yl]oxy}piperidin-2-yl]-N,N-bis(2-methoxyethyl)ethanamine;
7-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline;
6-chloro-2-{[(2R,3S)-2-(2-morpholin-4-ylethyl)-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinoline;
2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-7-carbonitrile;
2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-7-carboxamide;

6-fluoro-2-{[(2R,3S)-2-(2-morpholin-4-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine;

ethyl 5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylate;

5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-2-carboxylic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine;

6-chloro-1-(morpholin-4-ylmethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxylic acid;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1-(pyrrolidin-1-ylmethyl)-1,2,3,4-tetrahydroisoquinoline;

6-chloro-1-(methoxymethyl)-2-{[(2R,3S)-2-(2-pyrrolidin-1-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-1-(methoxymethyl)-2-{[(2R,3S)-2-(2-morpholin-4-ylethyl)-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]acetic acid;

2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridine-7-carboxylic acid;

2-(1-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}piperidin-4-yl)ethanol;

6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1-(methoxymethyl)-1,2,3,4-tetrahydroisoquinoline;

N-{2-[(2R,3S)-3-{[6-chloro-1-(methoxymethyl)-3,4-dihydroisoquinolin-2(1H)-yl]carbonyl}-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)propanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)propanamide;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-2,2-dimethylpropanoic acid;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-methylpropanamide;

ethyl 2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoate;

2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)propanoic acid;

2,2-dimethyl-3-(6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-N-(1H-tetrazol-5-ylmethyl)propanamide 3-(2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[2,3-c]pyridin-7-yl)-2,2-dimethylpropanoic acid;

2-chloro-4-(3-morpholin-4-ylpropyl)-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(3-pyrrolidin-1-ylpropyl)-4,5,6,7-tetrahydrothieno[3,2-c]pyridine;

2-chloro-N-methyl-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridine-4-carboxamide;

2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4-(pyrrolidin-1-ylmethyl)-4,5,6,7-tetrahydrothieno[3,2-c]pyridine;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl)propanamide;

3-(2-chloro-5-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno[3,2-c]pyridin-4-yl)-N-(methylsulfonyl)propanamide;

{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methoxy}acetic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

5-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)pentanoic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carbonitrile;

6-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquino line;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquino line;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquino line;

6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquino line;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol;

(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propan-1-ol;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)prop anoic acid;

3-(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)propanoic acid;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide;

3-(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl)propanamide;

6-phenyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(methylsulfonyl)propanamide;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-6-thiophen-3-yl-1,2,3,4-tetrahydroisoquinoline;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-N-(2H-tetrazol-5-ylmethyl)propanamide;

3-(6-chloro-2-{[(2R,3S)-2-propyl-1-{[3-(trifluoromethyl)pyridin-2-yl]carbonyl}-3-{[5-(trifluoromethyl)

thiophen-3-yl]oxy}piperidin-3-yl]carbonyl}-1,2,3,4-tetrahydroisoquinolin-1-yl)-2,2-dimethyl-N-(methylsulfonyl)propanamide;
(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanenitrile;
(6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;
4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid;
4-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)butanoic acid;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carbonitrile;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;
6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carbonitrile;
3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]-N-cyanopropanamide;
3-[(1S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl9-N-cyanopropanamide;
4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one;
1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol;
N,N-dimethyl-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-6-amine;
4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperazin-2-one;
1-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)acetyl]piperidin-4-ol;
5,6-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
6,7-dichloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
6-(methylsulfanyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-6-carboxamide;
6-(methylsulfonyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;
2-(4-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperazin-1-yl)ethanol;
2-{4-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;
2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;
2-{4-[(6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)carbonyl]piperazin-1-yl}ethanol;
[(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid;
3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)cyclopentanecarboxylic acid;
[(2R,3S)-3-[(1-carbamoyl-6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]acetic acid;
1-{3-[(1R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid;
1-{3-[(1S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl]propanoyl}piperidine-4-carboxylic acid;
6-chloro-2-{[(2R,3S)-2-propyl-1-{[3-(trifluoromethyl)pyridin-2-yl]carbonyl}-3-{[5-(trifluoromethyl)

thiophen-3-yl]oxy}piperidin-3-yl]carbonyl}-1,2,3,4-tetrahydroisoquinoline-1-carboxylic acid;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol;

6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methanol;

6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-1-(methoxymethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)-2,2-dimethylpropanoic acid;

6-chloro-1-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxamide;

6-fluoro-2-[(2-propyl-3-[4-(trifluoromethoxy)phenoxy]-1-{[3-(trifluoromethyl)pyridin-2-yl]carbonyl}piperidin-3-yl)carbonyl]-1,2,3,4-tetrahydroisoquinoline;

3-[(1S)-6-chloro-2-{[(2R,3S)-2-propyl-3-[4-(trifluoromethoxy)phenoxy]-1-{[3-(trifluoromethyl)pyridin-2-yl]carbonyl}piperidin-3-yl]carbonyl}-1,2,3,4-tetrahydroisoquinolin-1-yl]propanoic acid;

N-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}tetrahydro-2H-pyran-4-amine;

6-chloro-2-{[(2R,3S)-2-prop-2-en-1-yl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-1-carboxylic acid;

6-chloro-2-{[(2R,3S)-2-[2-(4-ethylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,3S)-2-[2-(4-methylpiperazin-1-yl)ethyl]-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

6-chloro-2-{[(2R,3S)-2-{2-[4-(cyclopropylmethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]-N-(2-methoxyethyl)-N-methylethanamine;

6-chloro-2-{[(2R,3S)-2-{2-[4-(2-methoxyethyl)piperazin-1-yl]ethyl}-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-(1-{2-[(2R,3S)-3-[(6-chloro-3,4-dihydroisoquinolin-2(1H)-yl)carbonyl]-1-{[3-(trifluoromethyl)pyridin-2-yl]carbonyl}-3-{[5-(trifluoromethyl)thiophen-3-yl]oxy}piperidin-2-yl]ethyl}piperidin-4-yl)-2-methylpropanoic acid;

[(3S)-2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-3-yl]methanol;

2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-8-ol;

(2-{[(2R,3S)-2-propyl-1-{[4-(trifluoromethyl)pyridin-3-yl]carbonyl}-3-{[5-(trifluoromethyl)thiophen-3-yl]oxy}piperidin-3-yl]carbonyl}-1,2,3,4-tetrahydroisoquinolin-1-yl)acetic acid;

(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

(3R)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

(3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

5-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]pentanoic acid;

3-[(3S)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid;

(3R)-6-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxylic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N,N-dimethylpropanamide;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-methylpropanamide;

(2S)-3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-methylpropanoic acid;

7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-methoxy-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

(3S)-6-chloro-3-(3-fluoropropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

7-bromo-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]acetic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-hydroxypropanamide;

4-[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butanoic acid;

3-[(3R)-7-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-N-(methylsulfonyl)propanamide;

1-{[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-4-ol;

(3R)-6-fluoro-N-(2-hydroxyethyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-3-carboxamide;

(2R)-N-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-2-methoxy-N-methylpropanamide;

N-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-N-methylpropanamide;

(2S)-2-{[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-3-methylbutanoic acid;

2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline-4-carboxylic acid;

(3S)-6-chloro-3-(3-morpholin-4-ylpropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

(3S)-6-chloro-3-{3-[(2S)-2-(methoxymethyl)pyrrolidin-1-yl]propyl}-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

3-[(3R)-6,7-difluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]propanoic acid;

(2R)-N-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-2-hydroxy-N-methylpropanamide;

2,2-difluoro-N-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}-N-methylacetamide;

(3S)-6-fluoro-3-[(4-methylpiperazin-1-yl)carbonyl]-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

(2R)-3-[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-(methoxymethyl)propanoic acid;

1-{[(3S)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}piperidin-4-ol;

(2R)-N-{2-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]ethyl}-2-hydroxy-N-methylpropanamide;

(2S)-3-[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]-2-hydroxypropanoic acid;

(2S)-2-{[(3S)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]methyl}butanoic acid;

(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-N-(tetrahydro-2H-pyran-4-yl)-1,2,3,4-tetrahydroisoquinoline-3-carboxamide;

4-[(3R)-6-fluoro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]butan-2-ol;

1-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-4-ol;

(3R)-6-chloro-3-[(4-methoxypiperidin-1-yl)carbonyl]-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

(3R)-1-{[(3R)-6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-3-yl]carbonyl}piperidin-3-ol;

6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno [2,3-c]pyridine-5-carboxylic acid;

2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno [2,3-c]pyridine-5-carboxylic acid;

6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno [2,3-c]pyridine-5-carboxylic acid;

2-chloro-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno [2,3-c]pyridine-5-carboxylic acid;

(5S)-2-bromo-N-(methylsulfonyl)-6-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-4,5,6,7-tetrahydrothieno [2,3-c]pyridine-5-carboxamide;

6-chloro-1-(2-methylpropyl)-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinoline;

2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid;

2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid;

2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid;

2-[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methyl]-3-methylbutanoic acid; and

[(6-chloro-2-{[(2R,3S)-2-propyl-1-{[3-(trifluoromethyl)pyridin-2-yl]carbonyl}-3-{[5-(trifluoromethyl)thiophen-3-yl]oxy}piperidin-3-yl]carbonyl}-1,2,3,4-tetrahydroisoquinolin-1-yl)methoxy]acetic acid;

or a stereoisomer thereof;

or a pharmaceutically acceptable salt thereof;

or a pharmaceutically acceptable salt of the stereoisomer thereof.

15. A pharmaceutical composition comprising a compound of claim 1 or a pharmaceutically acceptable salt thereof, in combination with at least one pharmaceutically acceptable carrier.

16. A method of inhibiting one or more HDM2 proteins in a patient comprising the step of administering a therapeutically effective amount of compound according to claim 1 to the patient.

* * * * *